(12) United States Patent
Bachmann et al.

(10) Patent No.: US 11,419,856 B2
(45) Date of Patent: Aug. 23, 2022

(54) PHARMACEUTICAL COMBINATIONS FOR USE IN THE TREATMENT OF NEOPLASTIC DISEASES

(71) Applicant: Basilea Pharmaceutica International AG, Basel (CH)

(72) Inventors: Felix Bachmann, Basel (CH); Heidi Lane, Basel (CH); Paul McSheehy, Basel (CH)

(73) Assignee: Basilea Pharmaceutica International AG, Basel (CH)

( * ) Notice: Subject to any disclaimer, the term of this patent is extended or adjusted under 35 U.S.C. 154(b) by 28 days.

(21) Appl. No.: 16/763,099

(22) PCT Filed: Nov. 20, 2018

(86) PCT No.: PCT/EP2018/081881
§ 371 (c)(1),
(2) Date: May 11, 2020

(87) PCT Pub. No.: WO2019/097073
PCT Pub. Date: May 23, 2019

(65) Prior Publication Data
US 2020/0390749 A1    Dec. 17, 2020

(30) Foreign Application Priority Data

Nov. 20, 2017  (EP) ...................................... 17202642
Mar. 15, 2018  (EP) ...................................... 18162122
Sep. 20, 2018  (EP) ...................................... 18195699

(51) Int. Cl.
| | | |
|---|---|---|
| *A61K 31/4245* | (2006.01) | |
| *A61P 35/04* | (2006.01) | |
| *A61K 9/00* | (2006.01) | |
| *A61K 31/357* | (2006.01) | |

(52) U.S. Cl.
CPC ........ *A61K 31/4245* (2013.01); *A61K 9/0019* (2013.01); *A61K 9/0053* (2013.01); *A61K 31/357* (2013.01); *A61P 35/04* (2018.01)

(58) Field of Classification Search
CPC ................................................ A61K 31/4245
See application file for complete search history.

(56) References Cited

U.S. PATENT DOCUMENTS 7,423,157 B2 * 9/2008 Eberle .................. A61P 3/10
548/264.8
2014/0163095 A1 * 6/2014 Kremer ................ A61P 35/04
514/450

FOREIGN PATENT DOCUMENTS

| EP | 0572109 A1 | 12/1993 |
|---|---|---|
| JP | 2016-008215 A1 | 1/2016 |

(Continued)

OTHER PUBLICATIONS

Minami H et al.; "446 Poster A phase I study of eribulin mesylate (E7389) in patients with refractory cancers;" European Journal of Cancer Supplement; Oct. 1, 2008; p. 140; 6(12); Oxford, GB.

(Continued)

*Primary Examiner* — Rei Tsang Shiao

(57) ABSTRACT

The present invention provides pharmaceutical combinations comprising (a) a compound of formula (I) wherein R represents phenyl or pyridinyl; wherein phenyl is optionally substituted by one or two substituents independently selected from lower alkyl, lower alkoxy, hydroxyl, amino, lower alkylamino, lower dialkylamino, acetylamino, halogen and nitro; and wherein pyridinyl is optionally substituted by amino or halogen; R1 represents hydrogen or cyano-lower alkyl; and wherein the prefix lower denotes a radical having up to and including a maximum of 4 carbon atoms; or a pharmaceutically acceptable derivative thereof; and (b) a compound of Formula (II) (eribulin) or a pharmaceutically acceptable salt thereof and the use of the pharmaceutical combinations in the treatment of neoplastic diseases.

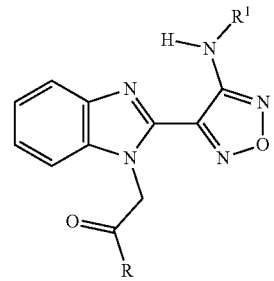

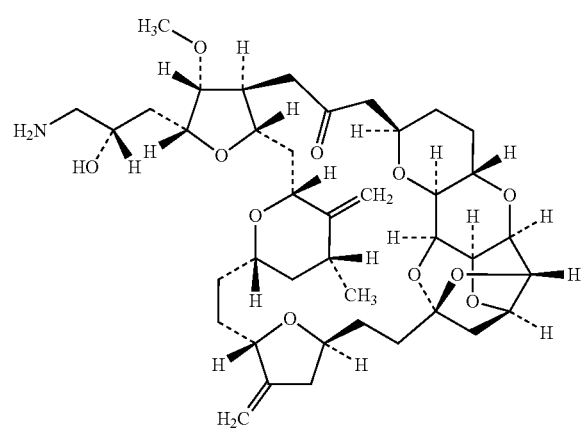

32 Claims, 16 Drawing Sheets

(56) References Cited

FOREIGN PATENT DOCUMENTS

| WO | 99/65894 A1 | 12/1999 |
|---|---|---|
| WO | 2004/034990 A2 | 4/2004 |
| WO | 2004/103994 A1 | 12/2004 |
| WO | 2007/061874 A2 | 5/2007 |
| WO | 2009/046308 A1 | 4/2009 |
| WO | 2010/113983 A1 | 10/2010 |
| WO | 2010/113984 A1 | 10/2010 |
| WO | 2011/012577 A1 | 2/2011 |
| WO | 2011/094339 A1 | 8/2011 |
| WO | 2012/098203 A1 | 7/2012 |
| WO | 2012/098207 A1 | 7/2012 |
| WO | 2012/098208 A1 | 7/2012 |
| WO | 2012/113802 A1 | 8/2012 |
| WO | 2012/129100 A1 | 9/2012 |
| WO | 2012/130887 A1 | 10/2012 |
| WO | WO 2012130887 * | 10/2012 |
| WO | 2014/087230 A1 | 6/2014 |
| WO | 2014/208774 A1 | 12/2014 |
| WO | 2015/066729 A1 | 5/2015 |
| WO | 2015/085193 A1 | 6/2015 |
| WO | 2015/134399 A1 | 9/2015 |
| WO | 2015/173341 A1 | 11/2015 |
| WO | 2015/183961 A1 | 12/2015 |
| WO | 2015/184145 A1 | 12/2015 |
| WO | 2016/031796 A1 | 3/2016 |
| WO | 2016/141209 A1 | 9/2016 |
| WO | 2017/068182 A1 | 4/2017 |
| WO | 2018/197475 A1 | 11/2018 |
| WO | 2018/210868 A1 | 11/2018 |
| WO | 2020/058405 A1 | 3/2020 |

OTHER PUBLICATIONS

Phase II Study of E/389, Halichondrin B analogue, in patients with advanced non-small cell lung cancer, NSCLC, who progressed during or after platinum-based doublet chemotherapy; www.clinicaltrials.gov; Mar. 27, 2012.
EPAR summary for the public; European Medicines Agency; May 2016; London, GB.
Oba T et al., "Preclinical analyses of synergistic effect of eribulin and paclitaxel for triple-negative breast cancer," American Association for Cancer Research; Apr. 2017; 77(13 Suppl); Abstr 1051; Washington, US.
Oba T et al.; Preclinical analyses of synergistic effect of eribulin and paclitaxel for triple-negative breast cancer; Poster, American Association for Cancer Research; Apr. 2017; 77(13 Suppl); Abstr 1051; Washington, US.
Ozawa Y et al.; "Suppression of metastasis and improvement of drug distribution by eribulin mesylate;" European Journal of Cancer; Nov. 19, 2014; 50; 6 Suppl; 17.
Ozawa Y et al.; "Suppression of metastasis and improvement of drug distribution by eribulin mesylate;" Poster, European Journal of Cancer; Nov. 19, 2014; 50; 6 Suppl; 17.
Garcia P et al; "Simultaneous combination of microtubule depolymerizing and stabilizing agents acts at low doses," Anti-Cancer Drugs; 1995; pp. 533-544; 6; Marseille, France.
Lu Y et al; "An Overview of Tubulin Inhibitors That Interact with the Colchicine Binding Site," Pharm Res; 2012; pp. 2943-2971; 29(11); Memphis, US.
Ehteda A et al; "Combination of Albendazole and 2-Methoxyestradiol significantly improves the survival of HCT-116 tumor-bearing nude mice," BMC Cancer; 2013; 13; 86.
Study NCT02824575—Rebastinib Plus Antitubulin Therapy With Paclitaxel or Eribulin in Metastatic Breast Cancer; www.clinicaltrials.gov; Aug. 11, 2016.
Study NCT02824575—Rebastinib Plus Antitubulin Therapy With Paclitaxel or Eribulin in Metastatic Breast Cancer; www.clinicaltrials.gov; Mar. 22, 2018.
Study NCT02824575—Rebastinib Plus Antitubulin Therapy With Paclitaxel or Eribulin in Metastatic Breast Cancer; www.clinicaltrials.gov; Jul. 12, 2018.
Study NCT02037529—Eribulin Mesylate or Paclitaxel as First- or Second-Line Therapy in Treating Patients With Recurrent Stage IIIC-IV Breast Cancer; www.clinicaltrials.gov; Jul. 17, 2017.
Study NCT02037529—A Randomized Phase III Trial of Eribulin Compared to Standard Weekly Paclitaxel as First- or Second-Line Therapy for Locally Recurrent or Metastatic Breast Cancer; www.clinicaltrials.gov; Mar. 13, 2018.
Study NCT02037529—A Randomized Phase III Trial of Eribulin Compared to Standard Weekly Paclitaxel as First- or Second-Line Therapy for Locally Recurrent or Metastatic Breast Cancer; www.clinicaltrials.gov; May 15, 2018.
Study NCT02037529—Eribulin Mesylate or Paclitaxel as First- or Second-Line Therapy in Treating Patients With Recurrent Stage IIIC-IV Breast Cancer; www.clinicaltrials.gov; May 15, 2018.
Study NCT02037529—Eribulin Mesylate or Paclitaxel as First- or Second-Line Therapy in Treating Patients With Recurrent Stage IIIC-IV Breast Cancer; www.clinicaltrials.gov; May 17, 2018.
Study NCT02037529—Eribulin Mesylate or Paclitaxel as First- or Second-Line Therapy in Treating Patients With Recurrent Stage IIIC-IV Breast Cancer; www.clinicaltrials.gov; Jun. 4, 2018.
Study NCT02037529—Eribulin Mesylate or Paclitaxel as First- or Second-Line Therapy in Treating Patients With Recurrent Stage IIIC-IV Breast Cancer; www.clinicaltrials.gov; Jun. 7, 2018.
Eisai and Halozyme sign collaboration agreement to investigate Eribulin and PEGPH20 in advanced breast cancer; Eisai press release; Jul. 31, 2014.
Swami, U et al.; Eribulin—A review of preclinical and clinical studies; Crit Rev Oncol Hematol; Feb. 2012; pp. 163-184 81(2); Bronx, US.
Yu M et al.; "Discovery of E7389, a fully synthetic Macrocyclic Ketone analog of Halichondrin B," Anticancer Agents from Natural Products; 2005; pp. 317-345.
Kimura T et al.; E7389, a novel antimicrotubule agent with potent p53-independant induction of p27, Bcl2 phosphorylation and cytotoxicity in non-small cell lung cancer (NSCLC); Proc Am Soc Clin Oncol; 2003; 22; Abstr 2804.
Kuznetsov G et al.; Induction of Morphological and Biochemical Apoptosis following Prolonged Mitotic Blockage by Halichondrin B Macrocyclic Ketone Analog E7389; Cancer Reseach; 2004; 64; pp. 5760-5766.
Towle M et al.; In vivo efficacy of E7389, a synthetic analog of the marine sponge antitubulin agent halichondrin B, against human tumor xenografts under monotheraphy and combination therapy conditions; Proc Am Assoc Cancer Res; 2003; 44; Abstr 5570; Andover, MA.
Dudka D et al.; Complete microtubule-kinetochore occupancy favours the segregation of merotelic attachments; Nature Communications; 2018; 9(1); 2042; Geneva, Switzerland.
Meraldi P; How cancer cells respond and become resistant to microtubule-interfering drugs; Feb. 1, 2018; Basel, Switzerland.
Forster-Gross N et al.; BAL101553, a novel microtubule-targeting tumor checkpoint controller, in combination with eribulin leads to increased cures in a TNBC xenograft model; EORTC; Nov. 13, 2018; Abstr LBA-11.
Bachmann F et al.; BAL101553 (prodrug of BAL27862): A unique microtubule destabilizer active against drug refractory breast cancers alone and in combination with trastuzumab; Cancer Research; Apr. 5, 2014; 74(19); Abstr 831.
Bachmann F et al.; BAL101553 (prodrug of BAL27862): A unique microtubule destabilizer active against drug refractory breast cancers alone and in combination with trastuzumab; AACR; 2014; Abstr 831. Poster.
Broggini-Tenzer A et al.; The novel microtubule-destabilizing drug BAL101553 (prodrug of BAL27862) sensitizes a treatment refractory tumor model to radiation therapy; European Journal of Cancer; 2014; 50(6); Abstr 202.
Bachmann F et al.; BAL101553 (prodrug of BAL27862): the spindle assembly checkpoint is required for anticancer activity; Cancer Research; Apr. 18, 2015; 75(15); Abstr 3789; Philadelphia, USA.
Burger K et al.; BAL101553 (prodrug of BAL27862): The 'Spindle Assembly Checkpoint' is required for anti-cancer activity; AACR; 2015; Abstr 3789.

(56) References Cited

OTHER PUBLICATIONS

Burger K et al.; BAL101553 (prodrug of BAL27862): The 'Spindle Assembly Checkpoint' is required for anti-cancer activity; EACR-AACR-SIC; Jun. 20, 2015; Abstr 715.

Mladek A et al.; The novel tubulin-binding 'tumor checkpoint controller' BAL101553 has anti-cancer activity alone and in combination treatments across a panel of GBM patient-derived xenografts; Cancer Research; Apr. 16, 2016; Abstr 4781.

Mladek A et al.; The novel tubulin-binding tumor checkpoint controller' BAL101553 has anti-cancer activity alone and in combination treatments across a panel of GBM patient-derived xenografts; Abstr 4781; Poster. 2016.

Lopez J et al.; Phase 1/2a trial of intravenous BAL101553, a novel tumor checkpoint controller (TCC), in advanced solid tumors; Journal of Clinical Oncology; p. 2525; 34(15); May 20, 2016.

Lopez J et al.; Phase 1/2a trial of intravenous BAL101553, a novel tumor checkpoint controller (TCC), in advanced solid tumors; ASCO; Jun. 3, 2016; Abstr2525; Poster.

Garces A et al.; A phase I study to assess the safety, pharmacokinetics (PK), pharmacodynamics (PD) and antitumor activities of daily oral BAL101553, a novel tumor checkpoint controller (TCC) in adult patients with progressive or recurrent glioblastoma (GBM) or high-grade glioma; Journal of Clinical Oncology; 2017; 35(15); Abstr TPS2601.

Garces A et al.; A phase I study to assess the safety, pharmacokinetics (PK), pharmacodynamics (PD) and antitumor activities of daily oral BAL101553, a novel tumor checkpoint controller (TCC) in adult patients with progressive or recurrent glioblastoma (GBM) or high-grade glioma; ASCO; Jun. 2, 2017; Abstr TPS2601; Poster.

Sharma A et al.; LB-151 / 23—The novel tubulin-binding, tumor checkpoint controller BAL101553 has differential affects on tumor vascularization with IV and oral dosing and provides superior anti-tumor activity in combination with bevacizumab; 2017; 77(13) Supp 1.

Sharma A et al.; LB-151 / 23—The novel tubulin-binding, tumor checkpoint controller BAL101553 has differential affects on tumor vascularization with IV and oral dosing and provides superior anti-tumor activity in combination with bevacizumab; ACCR; 2017; Abstr LB-151; Poster.

Sharma A et al.; The novel microtubule-destabilizing drug BAL101553 acts as radiosensitizing agent in treatment refractory tumor models; Strahlenther Onkol; pp. 865-876; 2017; 193.

Sharma A et al.; The novel microtubule targeting agent BAL101553 in combination with radiotherapy in treatment-refractory tumor models; Radiotherapy and Oncology; pp. 433-438; 124(3); 2017.

Bachmann F et al.; BAL101553, a novel microtubule-targeting tumor checkpoint controller, synergizes with gemcitabine providing cures in a PDX-pancreatic model; EORTC; Nov. 13, 2018; Abstr LBA-16.

Basilea presents preclinical data on its anticancer drug candidate BAL101553 at EORTC-NCI-AACR symposium; Press release; Nov. 14, 2018; Basel, Switzerland.

Asano M et al.; Broad-spectrum Preclinical Antitumor Activity of Eribulin (Halaven®): Combination with Anticancer Agents of Differing Mechanisms; Anticancer Research; pp. 3375-3385; 38; 2018.

Terashima M et al.; Synergistic antitumor effects of S-1 with eribulin in vitro and in vivo for triple-negative breast Dancer cell lines; SpringerPlus; 3; 417; 2014.

E7389, Halichondrin B analog (NSC 707389); CTEP Rapid Communication, Solicitation for letters of intent. 2005.

El Shemerly M et al.; AACR; Presentation; Apr. 5, 2014; San Diego, US.

Uenaka T et al.; Identification of drugs with eribulin combinatorial activity that kill both eribulin-sensitive and eribulin-insensitive tumor cells; AACR; Abstr 1698; Apr. 5, 2014; San Diego, US.

Laughney A et al.; Single-cell pharmacokinetic imaging reveals a therapeutic strategy to overcome drug resistance to the microtubule inhibitor eribulin; Science Translational Medicine; 6; 261; 2014.

Dabydeen D et al.; Comparison of the Activities of the Truncated Halichondrin B Analog NSC 707389 (E7389) with Those of the Parent Compound and a Proposed Binding Site on Tubulin; Molecular Pharmacology; pp. 1866-1875; 70 (6); 2006.

Towle M et al.; In Vitro and In Vivo Anticancer Activities of Synthetic Macrocyclic Ketone Analogues of Halichondrin B1; Cancer Research; pp. 1013-1021; 61; 2001.

Dubbelman A et al.; Mass Balance Study of [14C]Eribulin in Patients with Advanced Solid Tumors; Drug Metabolism and Disposition; pp. 313-321; 40(2); 2012.

Funahashi Y et al.; Eribulin mesylate reduces tumor microenvironment abnormality by vascular remodeling in preclinical human breast cancer models; Cancer Science; pp. 1334-1342; 105; 2014.

Smith J et al.; Eribulin Binds at Microtubule Ends to a Single Site on Tubulin to Suppress Dynamic Instability; Biochemistry; pp. 1331-1337; 49; 2010.

Wozniak K et al.; Comparison of Neuropathy-Inducing Effects of Eribulin Mesylate, Paclitaxel, and Ixabepilone in Mice; Cancer Research; pp. 3952-3962; 71; 2011.

Cortes J et al.; Eribulin monotherapy versus treatment of physician's choice in patients with metastatic breast cancer (EMBRACE): a phase 3 open-label randomised study; Lancet; p. 914-923; 377; 2011.

Mukohara T et al.; Eribulin mesylate in patients with refractory cancers: a Phase I study; Invest New Drugs; pp. 1926-1933; 30; 2012.

Schöffski P et al.; Activity of eribulin mesylate in patients with soft-tissue sarcoma: a phase 2 study in four ndependent histological subtypes; Lancet Oncol; p. 1045-1052; 12; 2011.

Jimeno A; Eribulin: RediscoveringTubulin as an Anticancer Target; Clin Cancer Res; pp. 3903-3905; 15(12); 2009.

Cortes J et al.; Eribulin mesylate, a novel microtubule inhibitor in the treatment of breast cancer; Cancer Treatment Reviews; 2011.

Preston J et al.; Eribulin: A Novel Cytotoxic Chemotherapy Agent; The Annals of Pharmacotherapy; pp. 802-811; 46; 2012.

Dybdal-Hargreaves N et al; Eribulin Mesylate: Mechanism of Action of a Unique Microtubule-Targeting Agent; Clin Cancer Res; pp. 2445-2452; 21; 2015.

EISAI Co Ltd; Financial Results Presentation; Mar. 31, 2011.

EISAI Co Ltd; Anticancer agent Halaven® demonstrates statically significant extension in progression free survival compared to Vinorelbine in Phase III clinical study of patients with breast cancer in China; News Release; 2016.

Cortes J et al.; Non-Taxane Microtubule Inhibitors in Metastatic Breast Cancer; Clinical Advances in Hematology & Oncology; pp. 9-14; 9(5); Supp 10; 2011.

Tan A et al.; Phase I Study of Eribulin Mesylate Administrated once every 21 days in patients with advanced solid tumours; Clin Cancer Res; pp. 4213-4219; 15; 2009.

Coel S et al.; A Phase I Study of Eribulin Mesylate (E7389), a Mechanistically Novel Inhibitor of Microtubule Dynamics, in Patients with Advanced Solid Malignancies; Clin Cancer Res; pp. 4207-4212; 15; 2009.

"Eribulin Mechanism of action, For the treatment of breast cancer," New Drugs, Jul. 2011. (Machine-generated English translation).

The International Search Report and Written Opinion, dated Dec. 12, 2018, in the corresponding PCT Appl. No. PCT/EP2018/081881.

The extended European search report, dated Apr. 3, 2018, in the related European Appl. No. 17202642.9.

\* cited by examiner

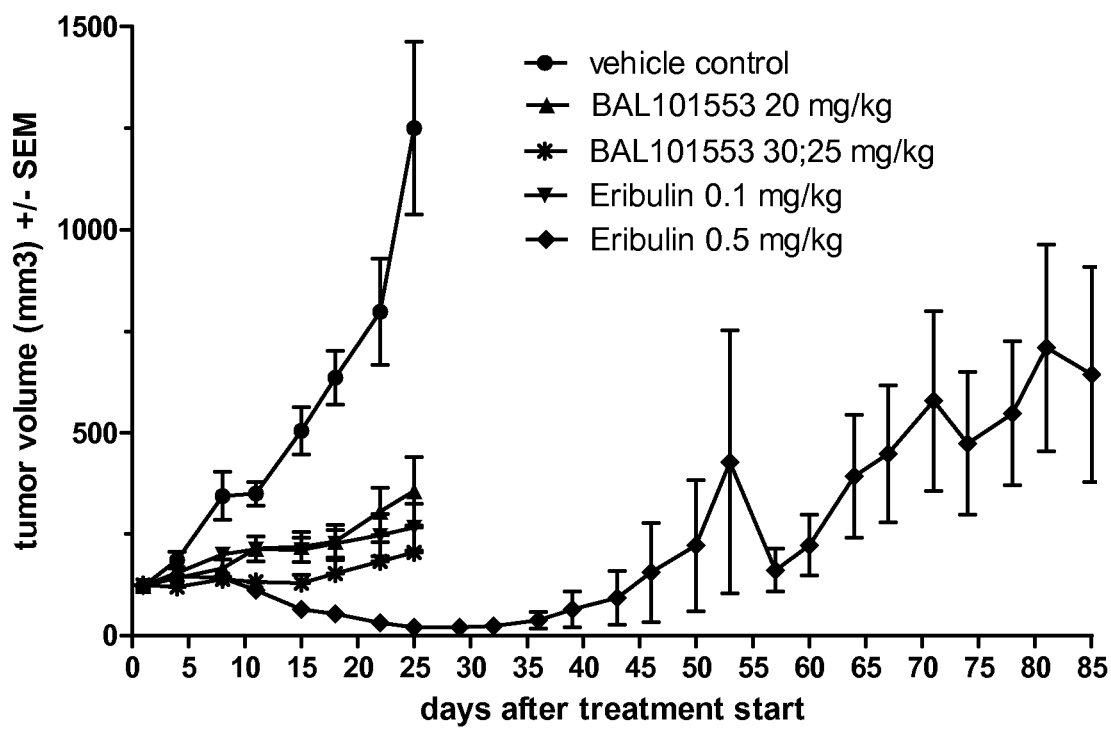
Figure 1A-i
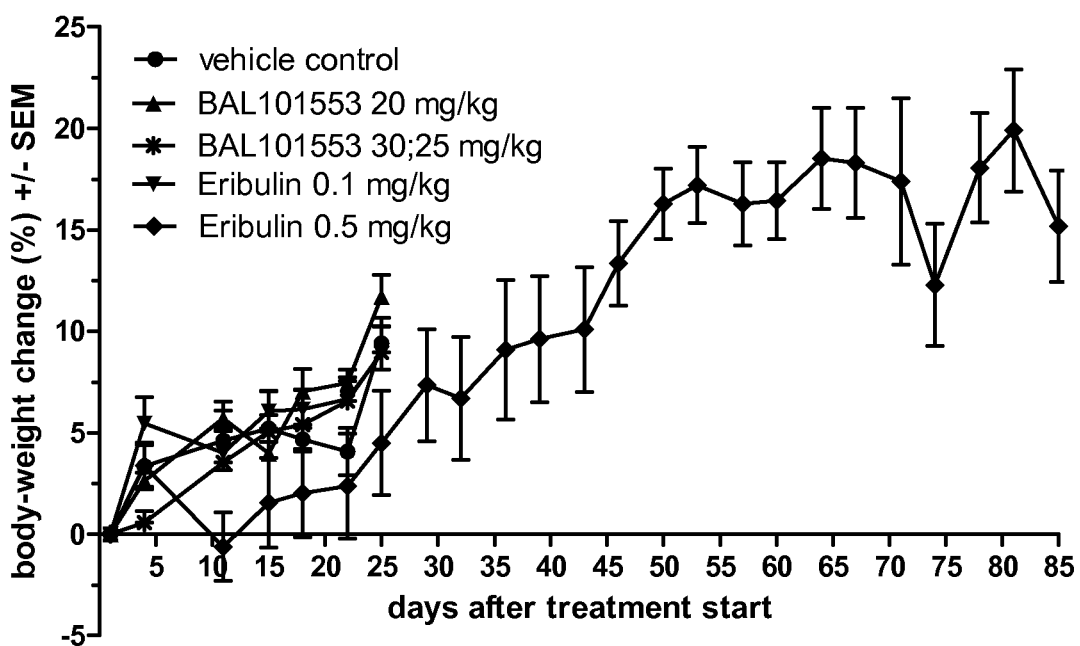
Figure 1A-ii

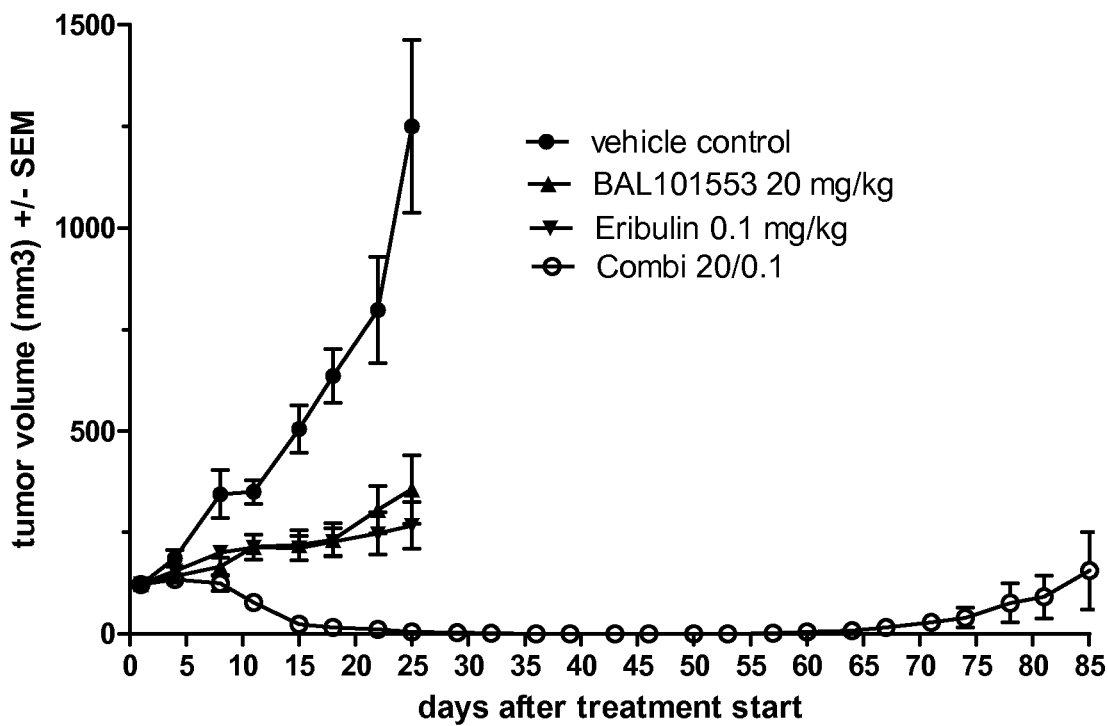
Figure 1B-i
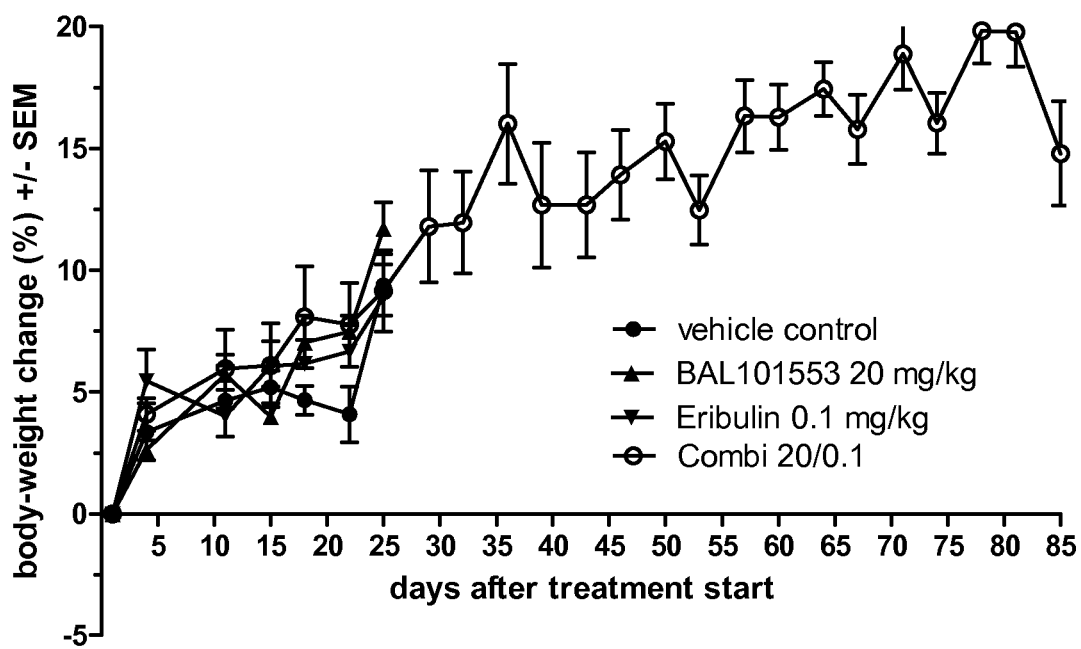
Figure 1B-ii

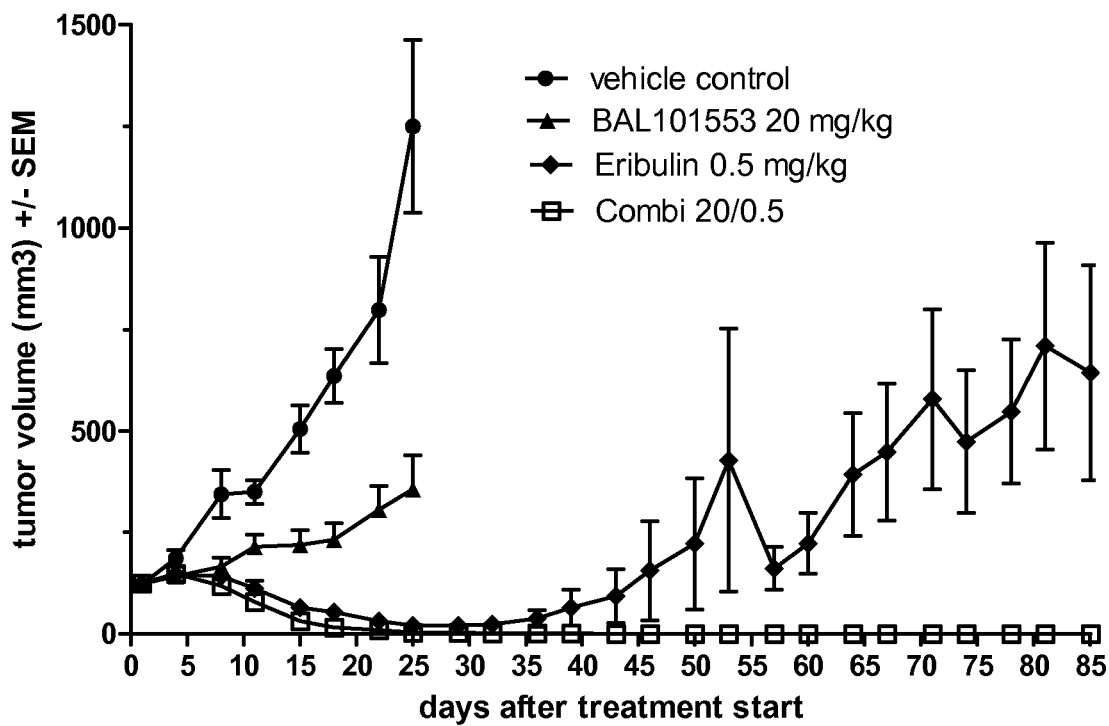
Figure 1C-i
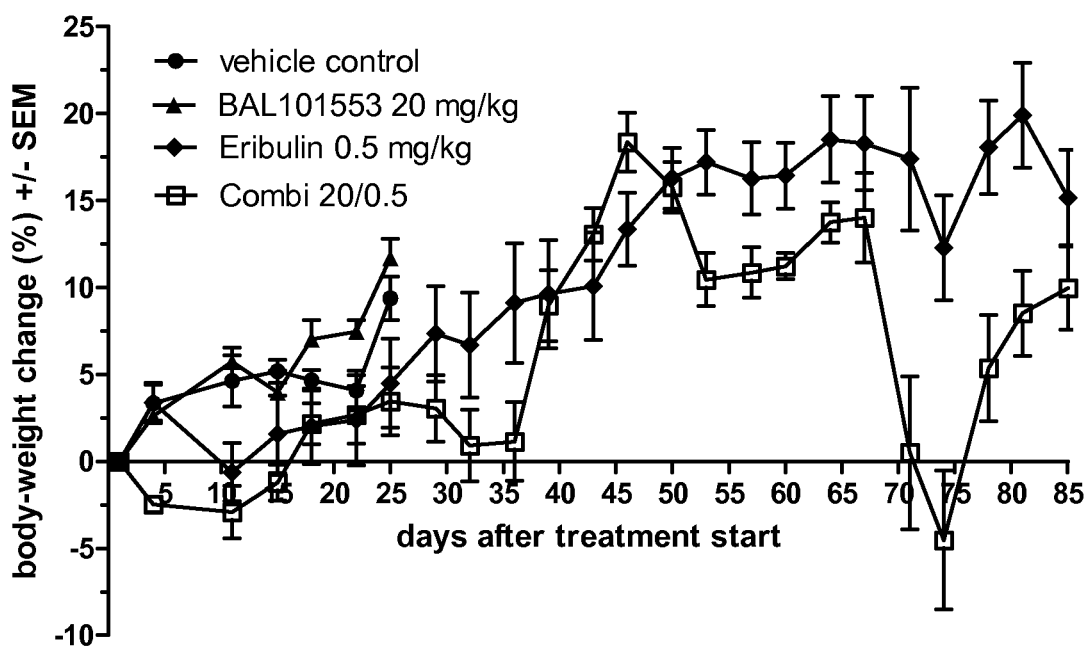
Figure 1C-ii

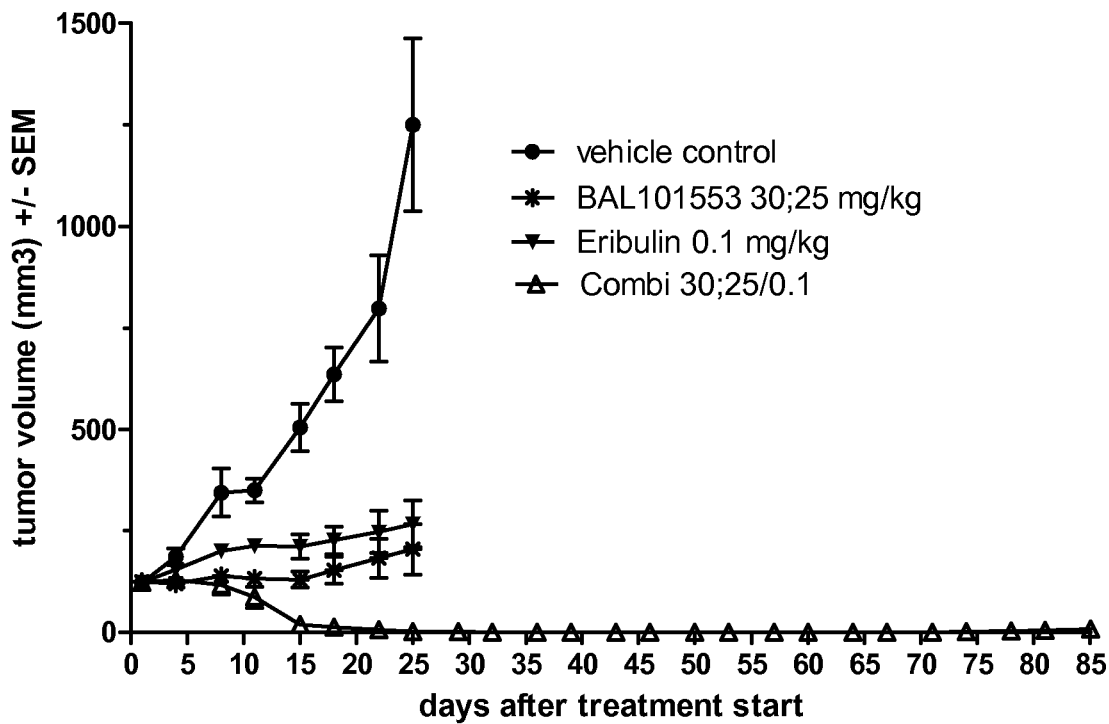
Figure 1D-i
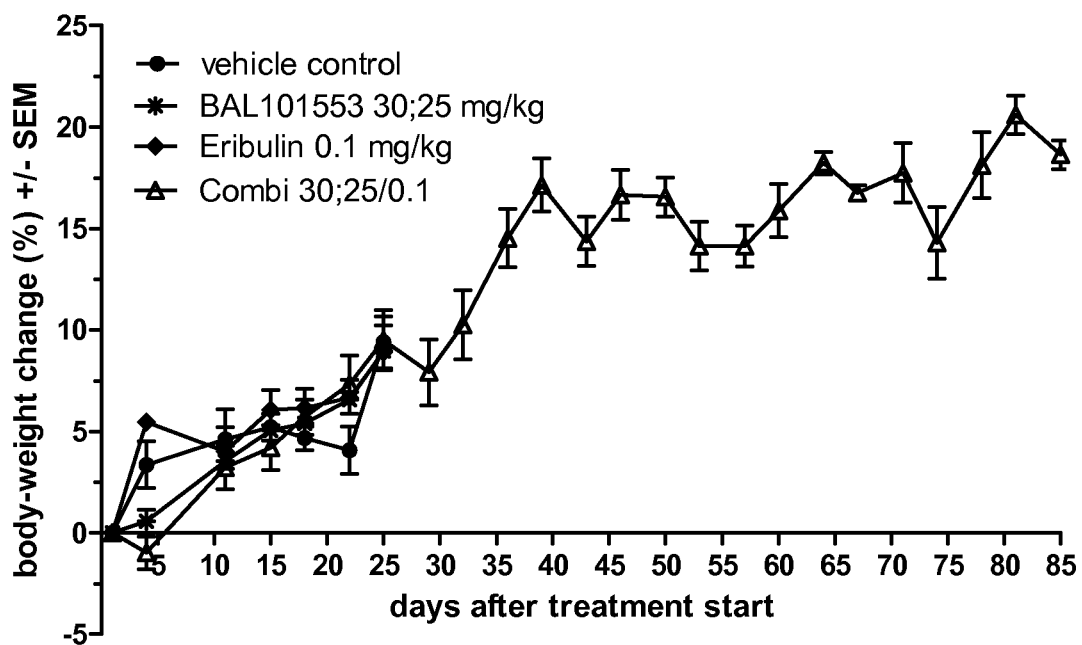
Figure 1D-ii

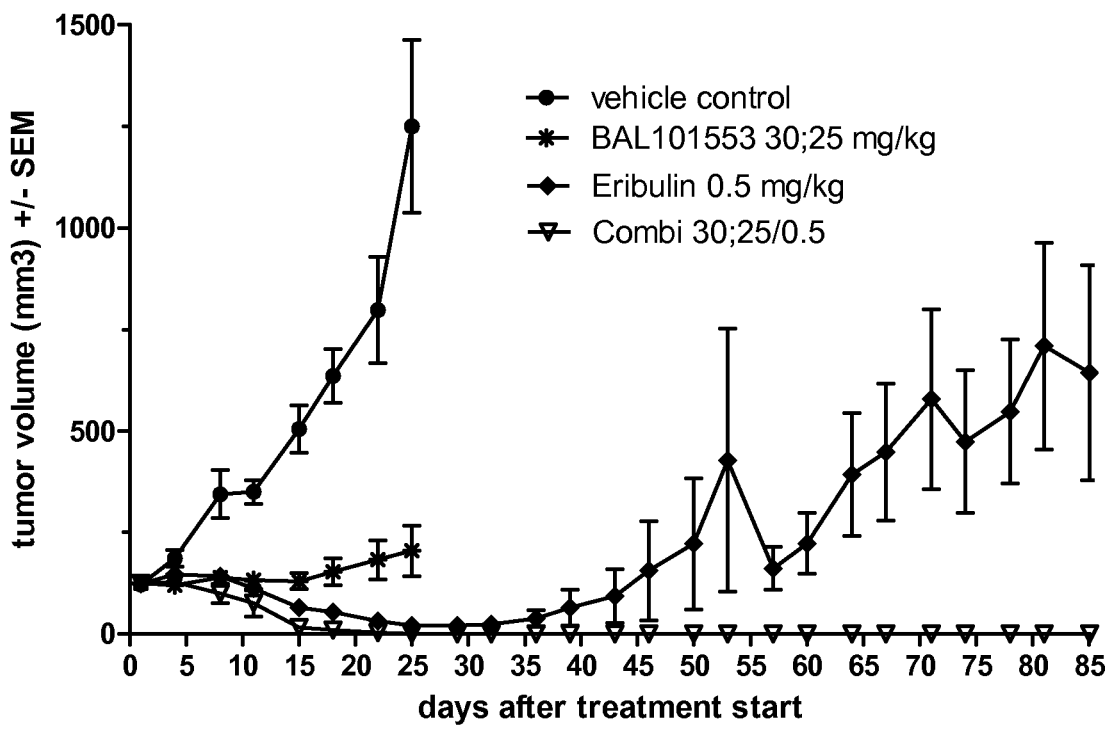
Figure 1E-i
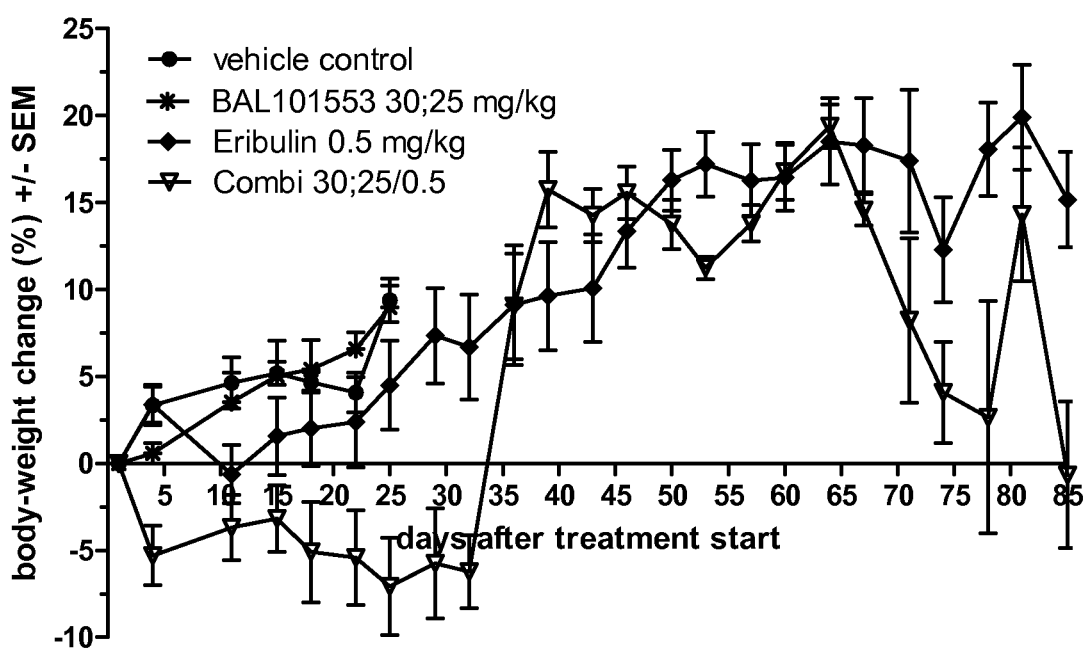
Figure 1E-ii

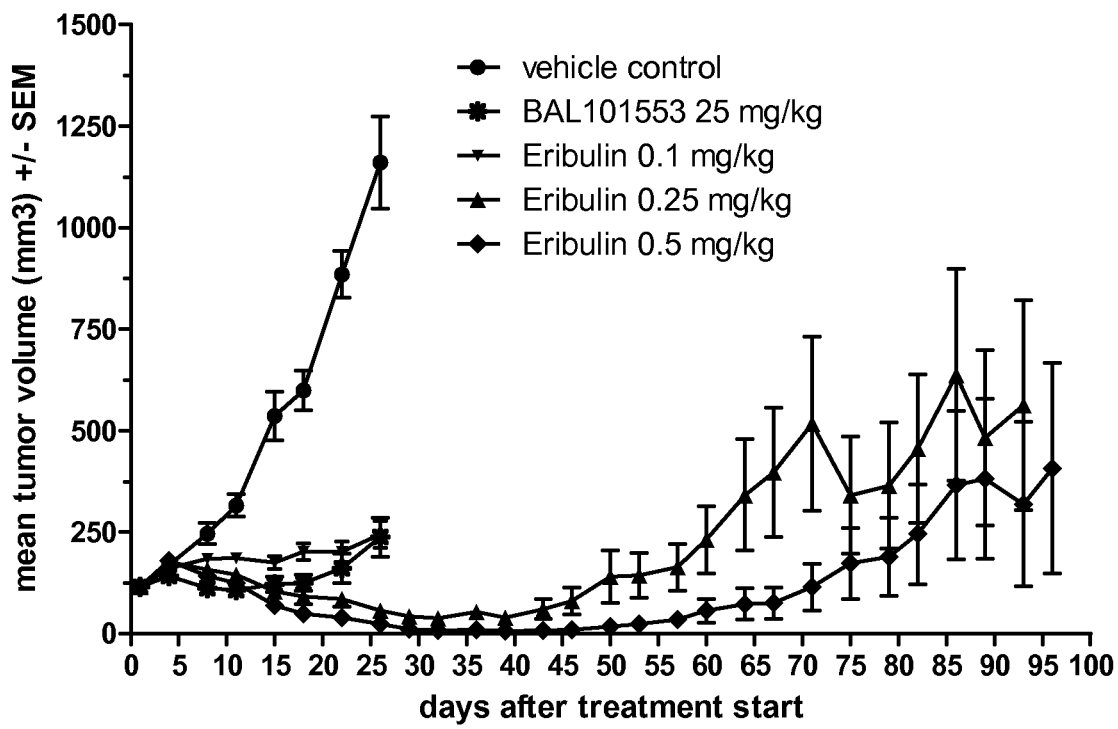
Figure 2A-i
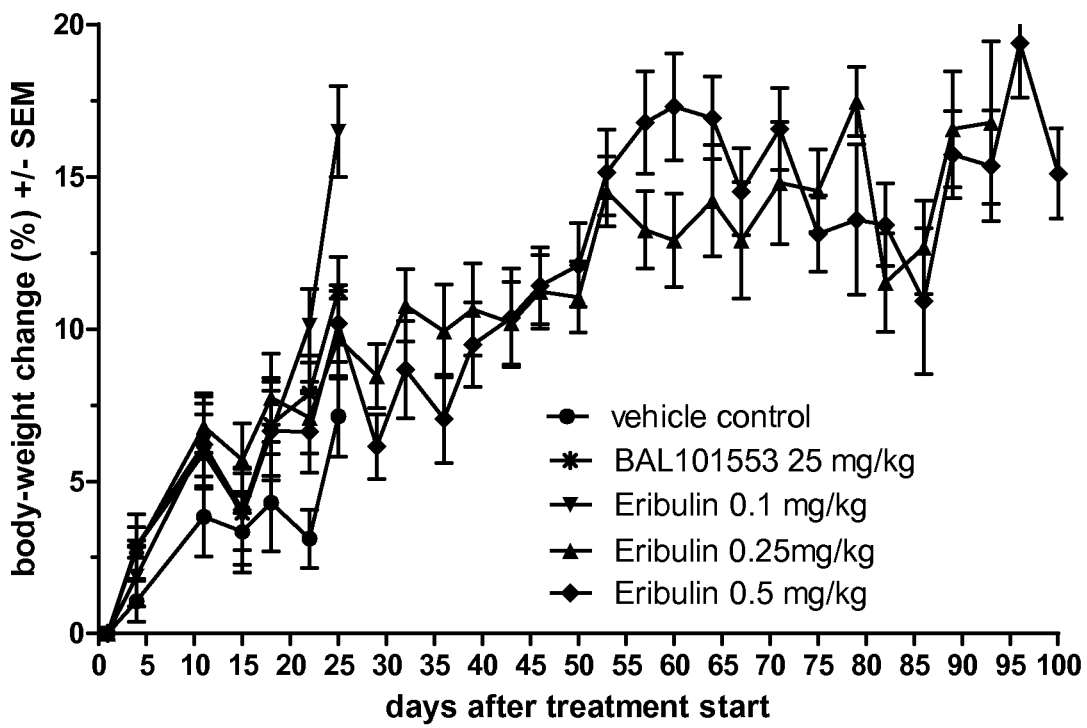
Figure 2A-ii

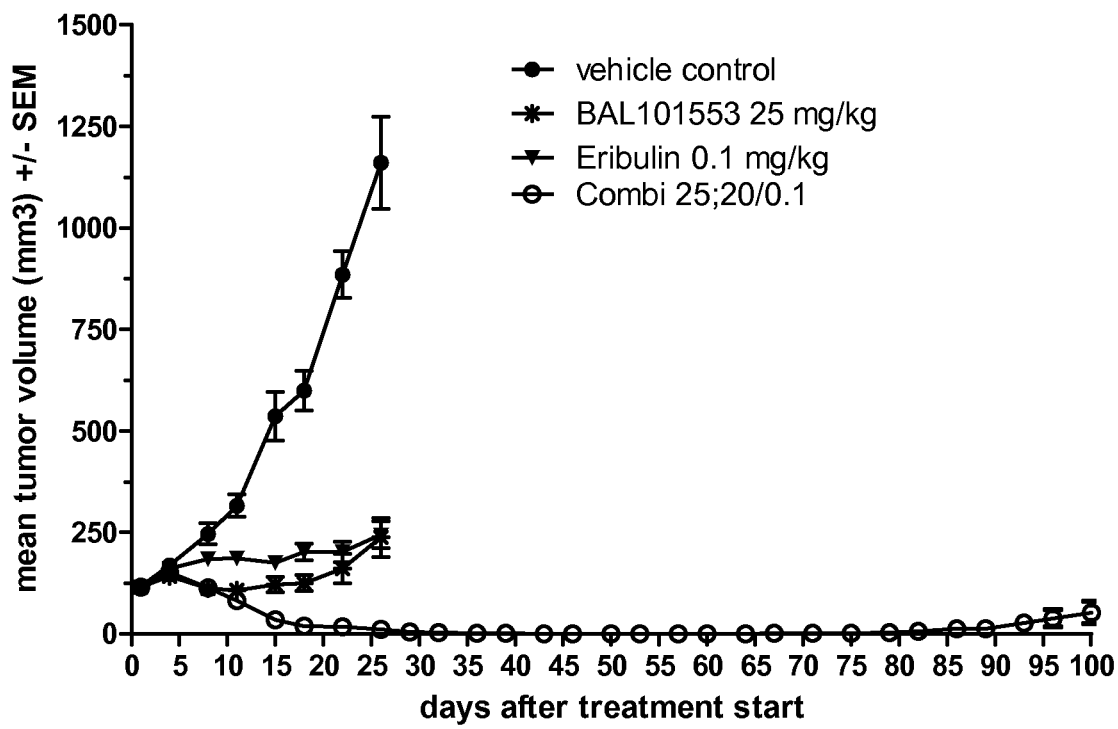
Figure 2B-i
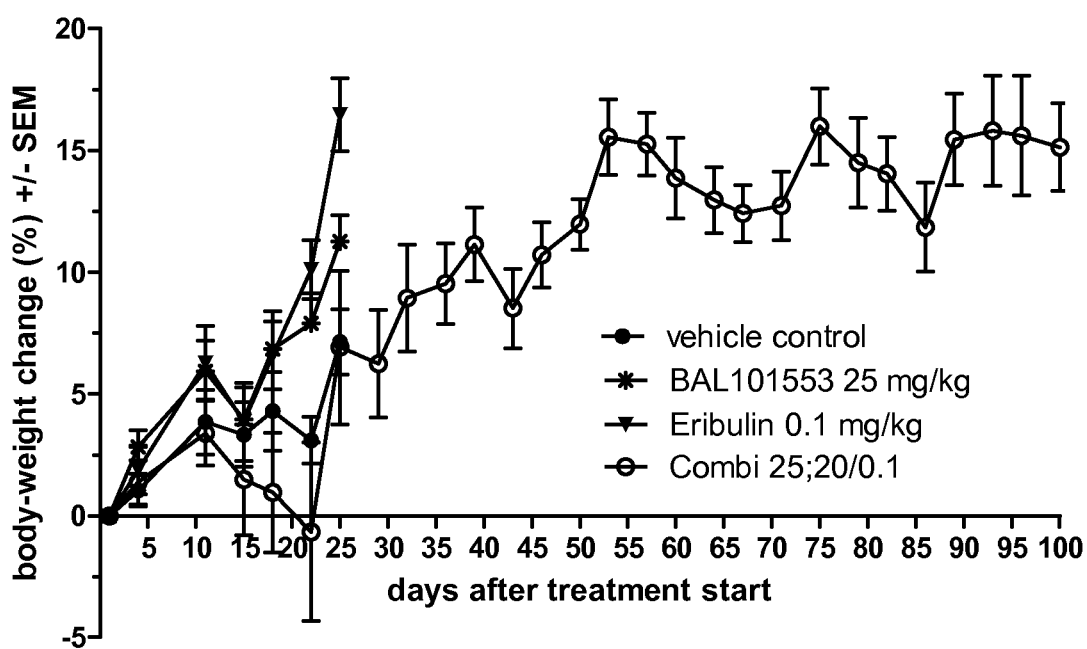
Figure 2B-ii

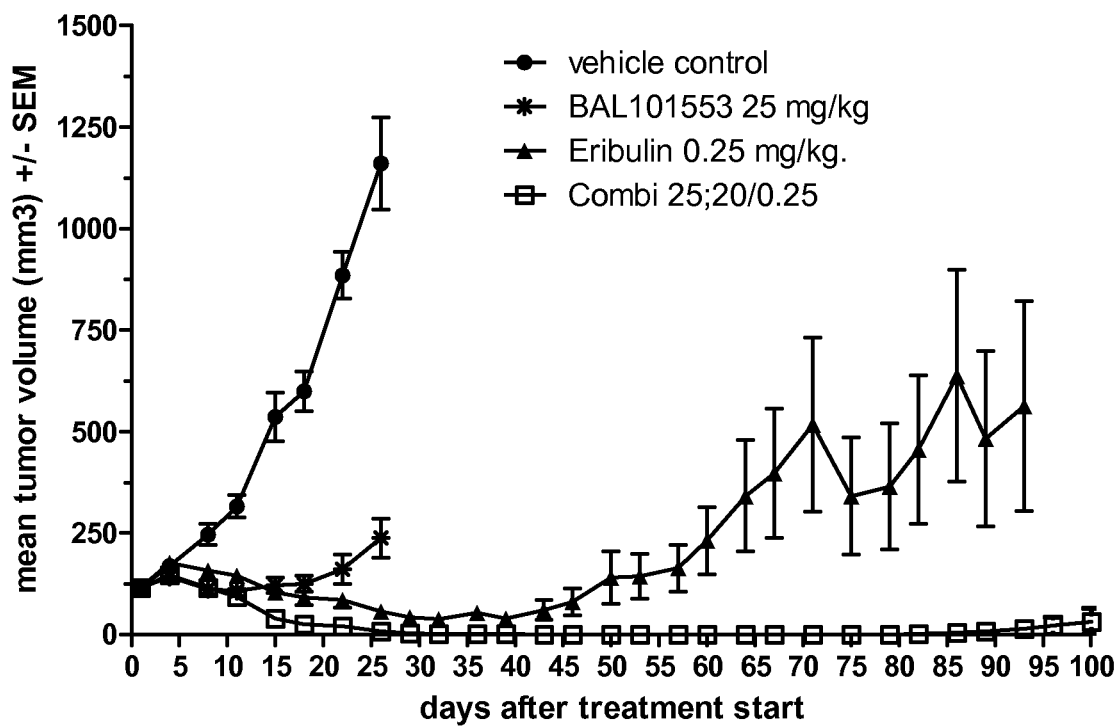
Figure 2C-i
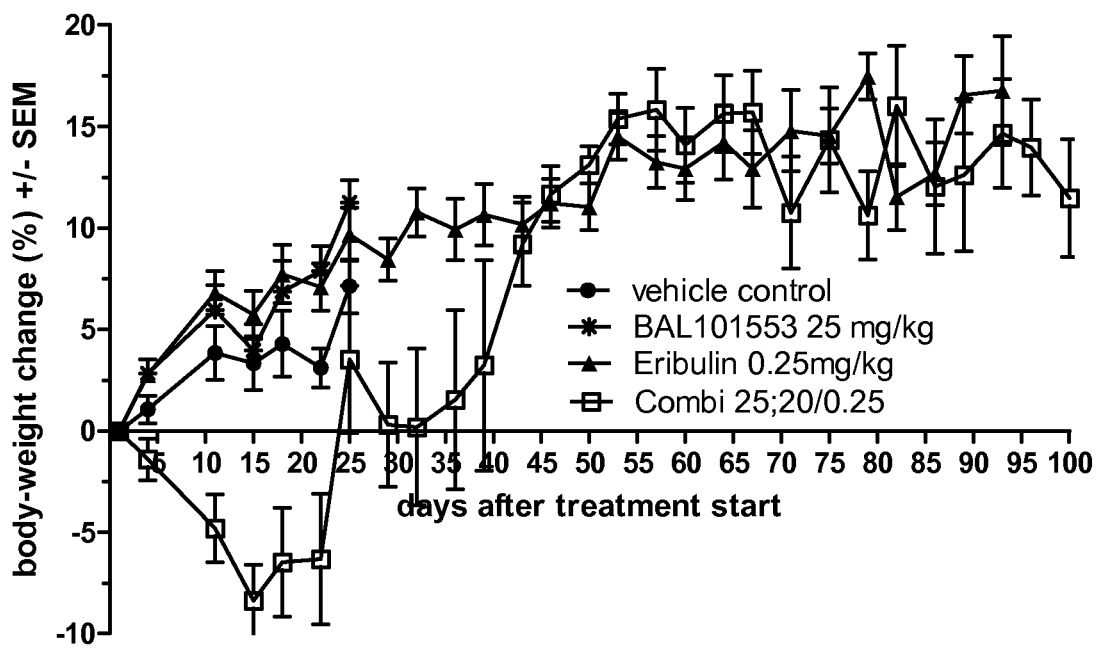
Figure 2C-ii

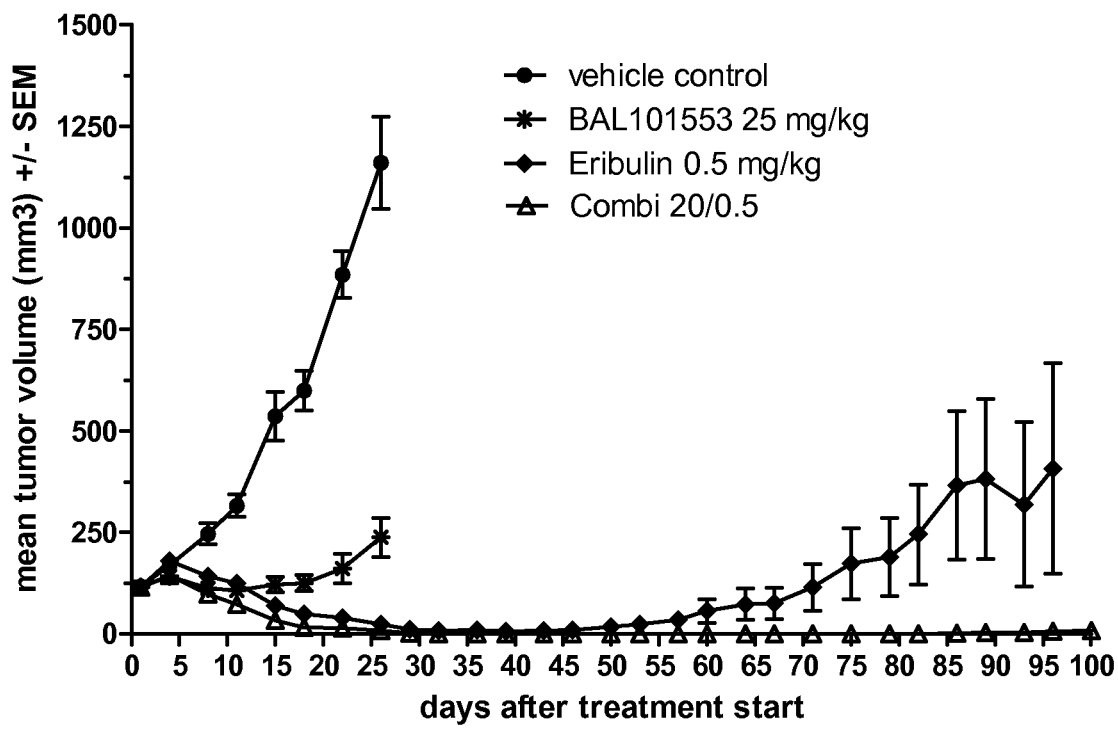
Figure 2D-ii
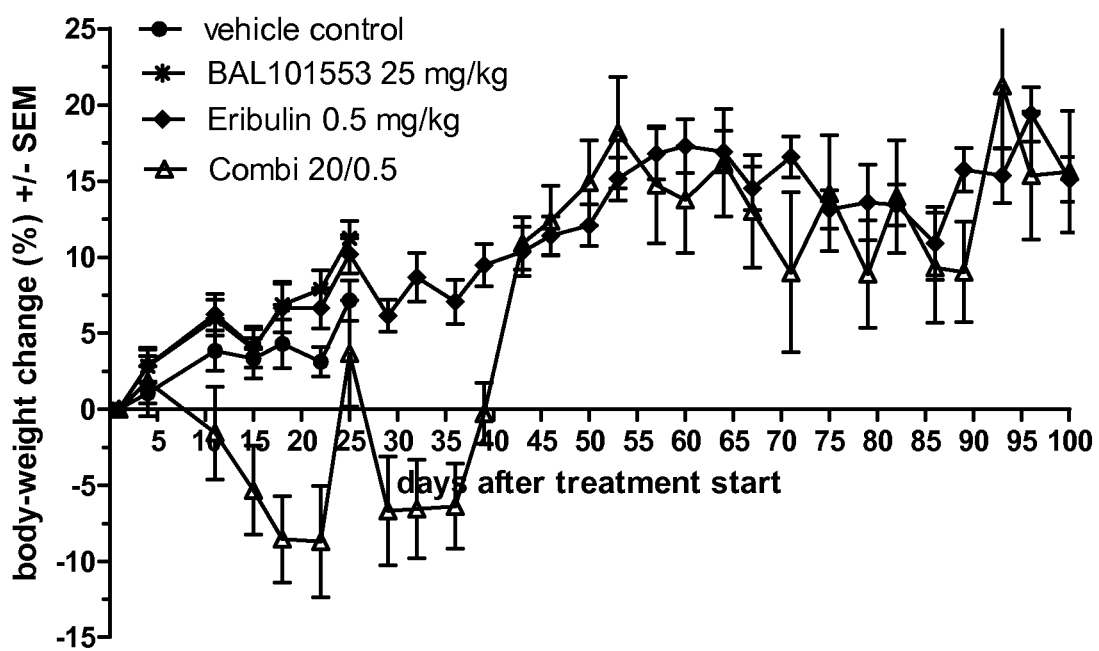
Figure 2D-ii

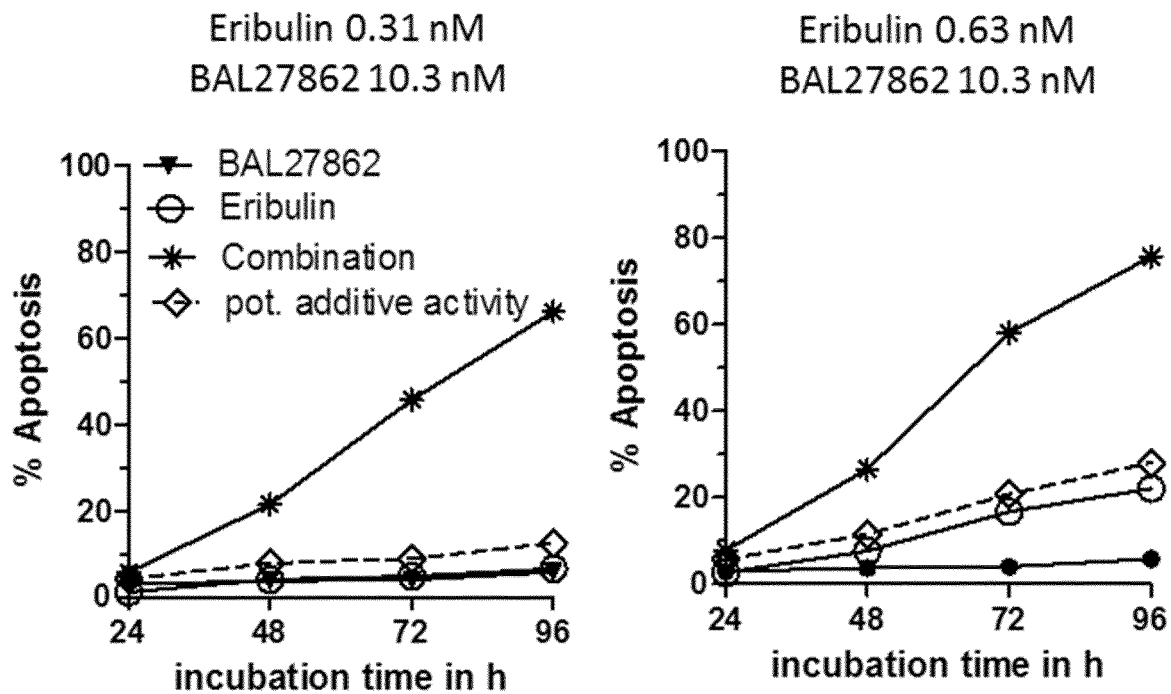
Figure 3-i
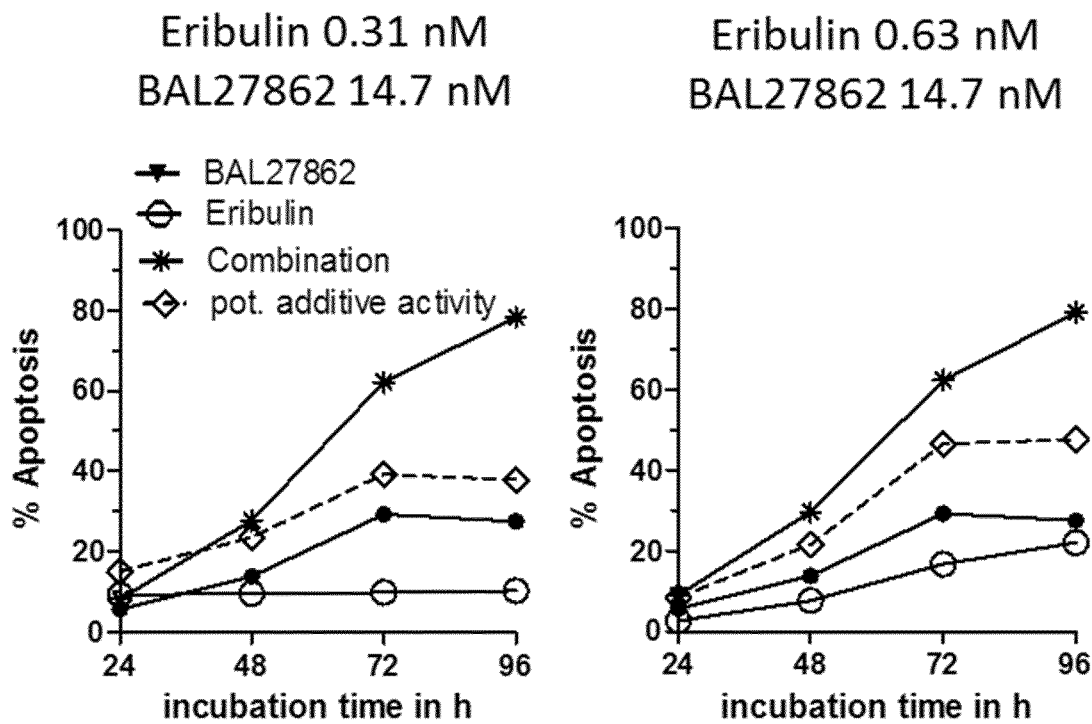
Figure 3-ii

Figure 7

| Grp | Drug | mg/kg | Route | Schedule | Dosing Vol. per 20 g (mL) | Doses per Day (Days 1-34) |
|---|---|---|---|---|---|---|
| 1# | vehicle | --- | po | qd x 5 then qd x 23 (start on Day 12) | 0.2 | |
| 2 | eribulin | 0.1 | iv | qod 5 then qod x 12 (start on Day 12) | 0.2 | |
| 3 | eribulin | 0.5 | iv | qod 5 then qod x 12 (start on Day 12) | 0.2 | |
| 4 | BAL101553 | 20 | po | qd x 5 then qd x 23 (start on Day 12) | 0.2 | |
| 5 | BAL101553 | 30 | po | qd x 5 | 0.2 | |
| 5 | BAL101553 | 25 | po | qd x 23 (start on Day 12) | 0.2 | |
| 6 | BAL101553 | 20 | po | qd x 5 then qod x 12 (start on Day 12) | 0.2 | |
| 6 | eribulin | 0.1 | iv | qod 5 then qod x 12 (start on Day 12) | 0.2 | |
| 7 | BAL101553 | 20 | po | qd x 5 then qd x 23 (start on Day 12) | 0.2 | |
| 7 | eribulin | 0.5 | iv | qod 5 then qod x 12 (start on Day 12) | 0.2 | |
| 8 | BAL101553 | 30 | po | qd x 5 | 0.2 | |
| 8 | BAL101553 | 25 | po | qd x 23 (start on Day 12) | 0.2 | |
| 8 | eribulin | 0.1 | iv | qod 5 then qod x 12 (start on Day 12) | 0.2 | |
| 9 | BAL101553 | 30 | po | qd x 5 | 0.2 | |
| 9 | BAL101553 | 25 | po | qd x 20 (start on Day 12) | 0.2 | |
| 9 | eribulin | 0.5 | iv | qod 5 then qod x 10 (start on Day 12) | 0.2 | |

\# - Control Group, * - Dosing volume adjusted to animal weight

Figure 8

PHARMACEUTICAL COMBINATIONS FOR USE IN THE TREATMENT OF NEOPLASTIC DISEASES

This application is a National Stage Application of PCT/EP2018/081881 filed Nov. 20, 2018, which claims priority from European Patent Application Nos. 17202642.9 filed on Nov. 20, 2017, 18162122.8 filed on Mar. 15, 2018 and 18195699.6 filed on Sep. 20, 2018. The priority of said PCT and European Patent Applications are claimed. Each of the prior mentioned applications is hereby incorporated by reference herein in its entirety.

The present invention relates to pharmaceutical combinations comprising two active pharmaceutical compounds as described herein and methods of using the combinations of the invention in the treatment of neoplastic diseases, in particular cancer.

Microtubules are one of the components of the cell cytoskeleton and are composed of heterodimers of alpha and beta tubulin. Agents that target microtubules are among the most effective cytotoxic chemotherapeutic agents and have a broad spectrum of activity. Microtubule destabilising agents (e.g. the vinca-alkaloids such as vincristine, vinblastine and vinorelbine) are used for example in the treatment of several types of hematologic malignancies, such as lymphoblastic leukaemia and lymphoma, as well as solid tumours, such as lung cancer. Microtubule stabilising agents (e.g. the taxanes such as paclitaxel, docetaxel) are used for example in the treatment of solid tumours, including breast, lung and prostate cancer.

WO2004/103994 describes a recently discovered class of microtubule destabilising agents. One compound falling within this class, known as BAL27862 (referred to herein as the compound of formula I-A), and shown in WO2004/103994 under Example 58, has the structure and chemical name given below:

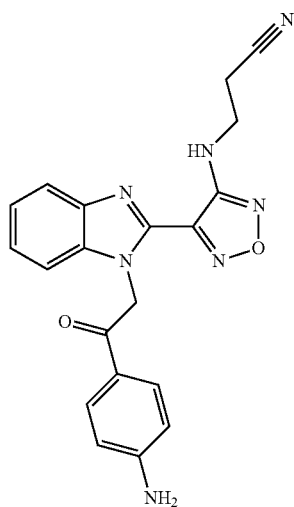

(I-A)

3-(4-{1-[2-(4-Amino-phenyl)-2-oxo-ethyl]-1H-benzoimidazol-2-yl}-furazan-3-ylamino)-propionitrile.

WO2011/012577 discloses pro-drugs of the compounds disclosed in WO2004/103994. One compound known as BAL101553 (referred to herein as the compound of formula I-B) and shown in WO2011/012577 under Example 1 has the chemical name and structure given below:

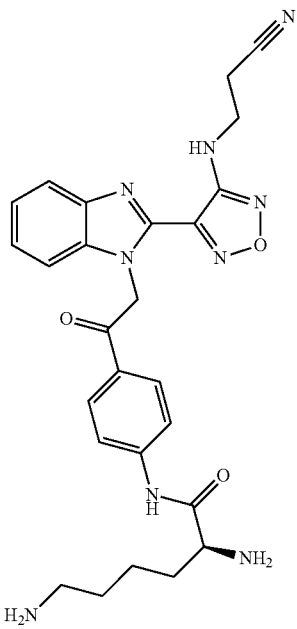

(I-B)

(S)-2,6-Diamino-hexanoic acid [4-(2-{2-[4-(2-cyano-ethylamino)-furazan-3-yl]-benzoimidazol-1-yl}-acetyl)-phenyl]-amide.

The compound of formula I-B is a highly water-soluble pro-drug of the compound of formula I-A which forms the compound of formula I-A following administration. The compound of formula I-B is particularly advantageously used in the form of a pharmaceutically acceptable acid addition salt, such as a hydrochloride salt, in particular in the form of its dihydrochloride salt.

These compounds have been shown to arrest tumour cell proliferation and induce apoptosis. The compound of formula I-A and the pro-drug of formula I-B have demonstrated antitumor activity across a broad panel of experimental tumour models.

Halichondrin B is a structurally complex macrocyclic compound that was originally isolated from the marine sponge *Halichondria okadai* and subsequently was found in *Axinella* sp., *Phakellia carteri*, and *Lissodendoryx* sp. A total synthesis of halichondrin B was published in 1992 (Aicher et al., J. Am. Chem. Soc. 114:3162-3164, 1992). Halichondrin B has been shown to inhibit tubulin polymerization, microtubule assembly, betaS-tubulin crosslinking, GTP and vinblastine binding to tubulin, and tubulin-dependent GTP hydrolysis in vitro. Halichondrin B analogues having anti-cancer activities are described in U.S. Pat. No. 6,214,865.

Eribulin is a synthetic analogue of halichondrin B. Eribulin is also known as ER-086526 and has been assigned CAS number 253128-41-5 and US NCI designation number NSC-707389. The mesylate salt of eribulin is approved for the treatment of breast cancer and soft tissue sarcoma (unresectable/metastatic liposarcoma).

As defined in the European Medicines Agency Assessment report for Halaven® eribulin, Procedure No. EMEA/H/C/002084, dated 20 Jan. 2011, Section 2.2.2, the chemical name for eribulin mesylate is (2R, 3R, 3aS, 7R, 8aS, 9S, 10aR, 11S, 12R, 13aR, 13bS, 15S, 18S, 21S, 24S, 26R, 28R, 29aS)-2-[(2S)-3-Amino-2-hydroxypropyl]-3-methoxy-26-methyl-20,27-dimethylidenehexacosahydro-11,15:18,21:24,28-triepoxy-7,9-ethano-12,15-methano-9H,15H-furo[3,2-i]furo[2',3':5,6]pyrano[4,3-b][1,4]dioxacyclopentacosin-5(4H)-one methanesulfonate (salt). Eribulin mesylate can be depicted as follows:

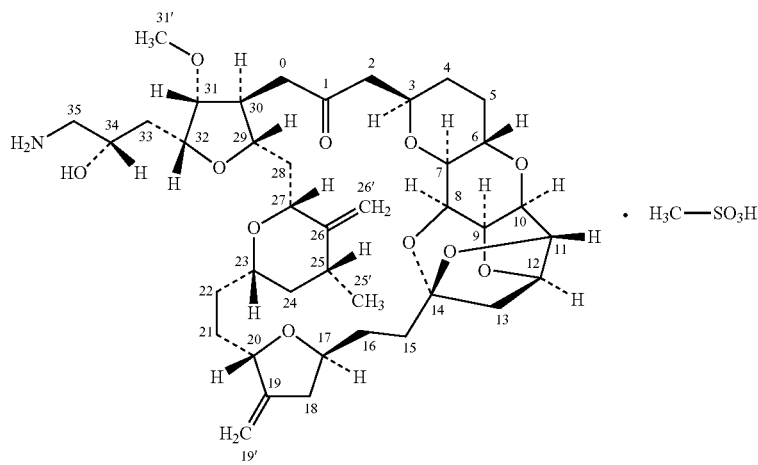

There is an ongoing need for new effective treatment options for cancer patients. As demonstrated in the Examples below it has now surprisingly been found that combinations of the two compounds described above, namely the compound of formula I-A/I-B and eribulin provide positive outcomes in cancer models, including cures.

SUMMARY OF THE INVENTION

In a first aspect the present invention provides a pharmaceutical combination comprising (a) a compound of formula I

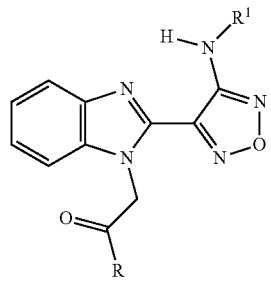

wherein

R represents phenyl or pyridinyl;

wherein phenyl is optionally substituted by one or two substituents independently selected from lower alkyl, lower alkoxy, hydroxyl, amino, lower alkylamino, lower dialkylamino, acetylamino, halogen and nitro;

and wherein pyridinyl is optionally substituted by amino or halogen;

R1 represents hydrogen or cyano-lower alkyl;

and wherein the prefix lower denotes a radical having up to and including a maximum of 4 carbon atoms;

or a pharmaceutically acceptable derivative thereof;

and (b) a compound of formula II (eribulin)

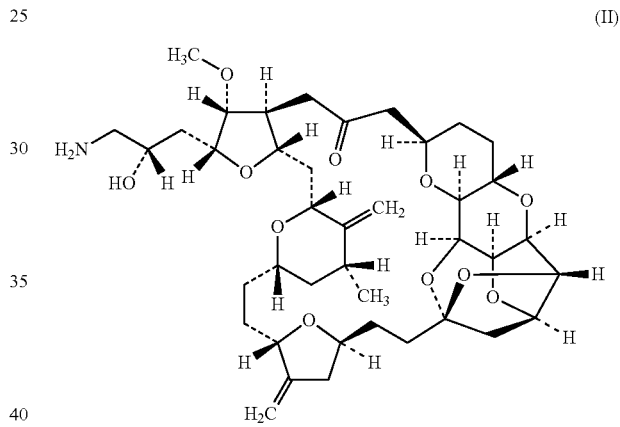

or a pharmaceutically acceptable salt thereof, e.g. eribulin mesylate.

In some embodiments component (a) is a compound of formula I-A or a pharmaceutically acceptable derivative thereof. In further embodiments component (a) is a compound of formula I-A or a pharmaceutically acceptable derivative thereof and component (b) is eribulin mesylate. In further embodiments component (a) is a compound of formula I-A or a pharmaceutically acceptable salt thereof or a compound of formula I-B or a pharmaceutically acceptable salt thereof. In further embodiments component (a) is a compound of formula I-A or a pharmaceutically acceptable salt thereof or a compound of formula I-B or a pharmaceutically acceptable salt thereof and component (b) is eribulin mesylate. In further embodiments component (a) is the dihydrochloride salt of the compound of formula I-B. In further embodiments component (a) is the dihydrochloride salt of the compound of formula I-B and component (b) is eribulin mesylate.

In a further aspect the invention provides a method for treating a neoplastic disease in a subject in need thereof comprising administering to the subject a therapeutically effective amount of the pharmaceutical combination of the invention. In some embodiments component (a) is a compound of formula I-A or a pharmaceutically acceptable derivative thereof. In further embodiments component (a) is a compound of formula I-A or a pharmaceutically acceptable derivative thereof and component (b) is eribulin mesylate. In further embodiments component (a) is a compound of formula I-A or a pharmaceutically acceptable salt thereof or a compound of formula I-B or a pharmaceutically acceptable salt thereof. In further embodiments component (a) is a compound of formula I-A or a pharmaceutically acceptable salt thereof or a compound of formula I-B or a pharmaceutically acceptable salt thereof and component (b) is eribulin mesylate. In further embodiments component (a) is the dihydrochloride salt of the compound of formula I-B. In further embodiments component (a) is the dihydrochloride salt of the compound of formula I-B and component (b) is eribulin mesylate.

In a further aspect the invention provides a method for treating a neoplastic disease in a subject in need thereof comprising administering to the subject a therapeutically effective amount of the compound of formula I or a pharmaceutically acceptable derivative thereof, wherein said subject is undergoing or will undergo treatment with the compound of formula II or pharmaceutically acceptable salt thereof. In some embodiments the compound of formula I or pharmaceutically acceptable derivative thereof is a compound of formula I-A or a pharmaceutically acceptable derivative thereof. In further embodiments the compound of formula I or pharmaceutically acceptable derivative thereof is a compound of formula I-A or a pharmaceutically acceptable derivative thereof and the compound of formula II or pharmaceutically acceptable salt thereof is eribulin mesylate. In further embodiments the compound of formula I or pharmaceutically acceptable derivative thereof is a compound of formula I-A or a pharmaceutically acceptable salt thereof or a compound of formula I-B or a pharmaceutically acceptable salt thereof. In further embodiments the compound of formula I or pharmaceutically acceptable derivative thereof is a compound of formula I-A or a pharmaceutically acceptable salt thereof or a compound of formula I-B or a pharmaceutically acceptable salt thereof and the compound of formula II or pharmaceutically acceptable salt thereof is eribulin mesylate. In further embodiments the compound of formula I or pharmaceutically acceptable derivative thereof is the dihydrochloride salt of the compound of formula I-B. In further embodiments the compound of formula I or pharmaceutically acceptable derivative thereof is the dihydrochloride salt of the compound of formula I-B and the compound of formula II or pharmaceutically acceptable salt thereof is eribulin mesylate.

In a further aspect the invention provides a method for treating a neoplastic disease in a subject in need thereof comprising administering to the subject a therapeutically effective amount of the compound of formula II or a pharmaceutically acceptable salt thereof, wherein said subject is undergoing or will undergo treatment with the compound of formula I or pharmaceutically acceptable derivative thereof. In some embodiments the compound of formula I or pharmaceutically acceptable derivative thereof is a compound of formula I-A or a pharmaceutically acceptable derivative thereof. In further embodiments the compound of formula I or pharmaceutically acceptable derivative thereof is a compound of formula I-A or a pharmaceutically acceptable derivative thereof and the compound of formula II or pharmaceutically acceptable salt thereof is eribulin mesylate. In further embodiments the compound of formula I or pharmaceutically acceptable derivative thereof is a compound of formula I-A or a pharmaceutically acceptable salt thereof or a compound of formula I-B or a pharmaceutically acceptable salt thereof. In further embodiments the compound of formula I or pharmaceutically acceptable derivative thereof is a compound of formula I-A or a pharmaceutically acceptable salt thereof or a compound of formula I-B or a pharmaceutically acceptable salt thereof and the compound of formula II or pharmaceutically acceptable salt thereof is eribulin mesylate. In further embodiments the compound of formula I or pharmaceutically acceptable derivative thereof is the dihydrochloride salt of the compound of formula I-B. In further embodiments the compound of formula I or pharmaceutically acceptable derivative thereof is the dihydrochloride salt of the compound of formula I-B and the compound of formula II or pharmaceutically acceptable salt thereof is eribulin mesylate.

In a further aspect the invention provides the pharmaceutical combination of the invention for use in the treatment of a neoplastic disease. In some embodiments component (a) is a compound of formula I-A or a pharmaceutically acceptable derivative thereof. In further embodiments component (a) is a compound of formula I-A or a pharmaceutically acceptable derivative thereof and component (b) is eribulin mesylate. In further embodiments component (a) is a compound of formula I-A or a pharmaceutically acceptable salt thereof or a compound of formula I-B or a pharmaceutically acceptable salt thereof. In further embodiments component (a) is a compound of formula I-A or a pharmaceutically acceptable salt thereof or a compound of formula I-B or a pharmaceutically acceptable salt thereof and component (b) is eribulin mesylate. In further embodiments component (a) is the dihydrochloride salt of the compound of formula I-B. In further embodiments component (a) is the dihydrochloride salt of the compound of formula I-B and component (b) is eribulin mesylate.

In a further aspect the invention provides a compound of formula I or a pharmaceutically acceptable derivative thereof for use in combination with a compound of formula II or pharmaceutically acceptable salt thereof for the treatment of a neoplastic disease. In some embodiments the compound of formula I or pharmaceutically acceptable derivative thereof is a compound of formula I-A or a pharmaceutically acceptable derivative thereof. In further embodiments the compound of formula I or pharmaceutically acceptable derivative thereof is a compound of formula I-A or a pharmaceutically acceptable derivative thereof and the compound of formula II or pharmaceutically acceptable salt thereof is eribulin mesylate. In further embodiments the compound of formula I or pharmaceutically acceptable derivative thereof is a compound of formula I-A or a pharmaceutically acceptable salt thereof or a compound of formula I-B or a pharmaceutically acceptable salt thereof. In further embodiments the compound of formula I or pharmaceutically acceptable derivative thereof is a compound of formula I-A or a pharmaceutically acceptable salt thereof or a compound of formula I-B or a pharmaceutically acceptable salt thereof and the compound of formula II or pharmaceutically acceptable salt thereof is eribulin mesylate. In further embodiments the compound of formula I or pharmaceutically acceptable derivative thereof is the dihydrochloride salt of the compound of formula I-B. In further embodiments the compound of formula I or pharmaceutically acceptable derivative thereof is the dihydrochloride salt of the compound of formula I-B and the compound of formula II or pharmaceutically acceptable salt thereof is eribulin mesylate.

In a further aspect the invention provides a compound of formula II or a pharmaceutically acceptable salt thereof for use in combination with a compound of formula I or pharmaceutically acceptable derivative thereof for the treatment of a neoplastic disease. In some embodiments the compound of formula I or pharmaceutically acceptable derivative thereof is a compound of formula I-A or a pharmaceutically acceptable derivative thereof. In further embodiments the compound of formula I or pharmaceutically acceptable derivative thereof is a compound of formula I-A or a pharmaceutically acceptable derivative thereof and the compound of formula II or pharmaceutically acceptable salt thereof is eribulin mesylate. In further embodiments the compound of formula I or pharmaceutically acceptable derivative thereof is a compound of formula I-A or a pharmaceutically acceptable salt thereof or a compound of formula I-B or a pharmaceutically acceptable salt thereof. In further embodiments the compound of formula I or pharmaceutically acceptable derivative thereof is a compound of formula I-A or a pharmaceutically acceptable salt thereof or a compound of formula I-B or a pharmaceutically acceptable salt thereof and the compound of formula II or pharmaceutically acceptable salt thereof is eribulin mesylate. In further embodiments the compound of formula I or pharmaceutically acceptable derivative thereof is the dihydrochloride salt of the compound of formula I-B. In further embodiments the compound of formula I or pharmaceutically acceptable derivative thereof is the dihydrochloride salt of the compound of formula I-B and the compound of formula II or pharmaceutically acceptable salt thereof is eribulin mesylate.

In a further aspect the invention provides use of the pharmaceutical combination of the invention in the preparation of single-agent medicaments or as a combined medicament for the treatment of a neoplastic disease. In some embodiments component (a) is a compound of formula I-A or a pharmaceutically acceptable derivative thereof. In further embodiments component (a) is a compound of formula I-A or a pharmaceutically acceptable derivative thereof and component (b) is eribulin mesylate. In further embodiments component (a) is a compound of formula I-A or a pharmaceutically acceptable salt thereof or a compound of formula I-B or a pharmaceutically acceptable salt thereof. In further embodiments component (a) is a compound of formula I-A or a pharmaceutically acceptable salt thereof or a compound of formula I-B or a pharmaceutically acceptable salt thereof and component (b) is eribulin mesylate. In further embodiments component (a) is the dihydrochloride salt of the compound of formula I-B. In further embodiments component (a) is the dihydrochloride salt of the compound of formula I-B and component (b) is eribulin mesylate.

In a further aspect the invention provides use of a compound of formula I or a pharmaceutically acceptable derivative thereof in the preparation of a single-agent medicament for use in combination with a compound of formula II or pharmaceutically acceptable salt thereof or in the preparation of a combined medicament with the compound of formula II or pharmaceutically acceptable salt thereof, for the treatment of a neoplastic disease. In some embodiments the compound of formula I or pharmaceutically acceptable derivative thereof is a compound of formula I-A or a pharmaceutically acceptable derivative thereof. In further embodiments the compound of formula I or pharmaceutically acceptable derivative thereof is a compound of formula I-A or a pharmaceutically acceptable derivative thereof and the compound of formula II or pharmaceutically acceptable salt thereof is eribulin mesylate. In further embodiments the compound of formula I or pharmaceutically acceptable derivative thereof is a compound of formula I-A or a pharmaceutically acceptable salt thereof or a compound of formula I-B or a pharmaceutically acceptable salt thereof. In further embodiments the compound of formula I or pharmaceutically acceptable derivative thereof is a compound of formula I-A or a pharmaceutically acceptable salt thereof or a compound of formula I-B or a pharmaceutically acceptable salt thereof and the compound of formula II or pharmaceutically acceptable salt thereof is eribulin mesylate. In further embodiments the compound of formula I or pharmaceutically acceptable derivative thereof is the dihydrochloride salt of the compound of formula I-B. In further embodiments the compound of formula I or pharmaceutically acceptable derivative thereof is the dihydrochloride salt of the compound of formula I-B and the compound of formula II or pharmaceutically acceptable salt thereof is eribulin mesylate.

In a further aspect the invention provides use of a compound of formula II or a pharmaceutically acceptable salt thereof in the preparation of a single-agent medicament for use in combination with a compound of formula I or pharmaceutically acceptable derivative thereof or in the preparation of a combined medicament with the compound of formula I or pharmaceutically acceptable derivative thereof, for the treatment of a neoplastic disease. In some embodiments the compound of formula I or pharmaceutically acceptable derivative thereof is a compound of formula I-A or a pharmaceutically acceptable derivative thereof. In further embodiments the compound of formula I or pharmaceutically acceptable derivative thereof is a compound of formula I-A or a pharmaceutically acceptable derivative thereof and the compound of formula II or pharmaceutically acceptable salt thereof is eribulin mesylate. In further embodiments the compound of formula I or pharmaceutically acceptable derivative thereof is a compound of formula I-A or a pharmaceutically acceptable salt thereof or a compound of formula I-B or a pharmaceutically acceptable salt thereof. In further embodiments the compound of formula I or pharmaceutically acceptable derivative thereof is a compound of formula I-A or a pharmaceutically acceptable salt thereof or a compound of formula I-B or a pharmaceutically acceptable salt thereof and the compound of formula II or pharmaceutically acceptable salt thereof is eribulin mesylate. In further embodiments the compound of formula I or pharmaceutically acceptable derivative thereof is the dihydrochloride salt of the compound of formula I-B. In further embodiments the compound of formula I or pharmaceutically acceptable derivative thereof is the dihydrochloride salt of the compound of formula I-B and the compound of formula II or pharmaceutically acceptable salt thereof is eribulin mesylate.

Of particular interest is the compound of formula I-A (BAL27862) and pharmaceutically acceptable derivatives thereof. Examples of derivatives of the compound of formula I and in particular of the compound of formula I-A are described herein. Of particular interest is the compound of formula I-B (BAL101553, as indicated above) and pharmaceutically acceptable salts thereof. More particularly a dihydrochloride salt of the compound of formula I-B.

The compound of formula I or pharmaceutically acceptable derivative thereof and the compound of formula II or pharmaceutically acceptable salt thereof may be in the same pharmaceutical composition, e.g. as a single dosage unit, but will usually be provided in separate pharmaceutical compositions, e.g. as separate dosage units. Separate pharmaceutical compositions have a number of advantages, for example, to allow different dosing schedules, different dosages and/or different routes of administration for each compound. When provided as separate formulations the combination may be for separate, simultaneous or sequential administration.

Neoplastic diseases for treatment by combinations of the invention are described below, and are in particular contemplated for treatment of cancer, and in particular for human subjects.

Additional aspects and embodiments of the invention are described in more detail below.

BRIEF DESCRIPTION OF FIGURES

FIG. 1 shows the results of an experiment comparing the efficacy and tolerability of the combination of BAL101553 with eribulin versus the respective monotherapies in mice bearing the human triple negative breast cancer (TNBC) tumour MDA-MB231 xenograft. BAL101553 was administered orally daily and eribulin intravenously every second day. In the combined regimen eribulin was administered 30 minutes before BAL101553 when administered on the same day. Control animals received vehicle control according to the applied single agent application schedules respectively. FIG. 1A shows the results of each of the single agent treatments. FIG. 1B shows the results of the combination treatment in which BAL101553 was administered at a dose of 20 mg/kg and eribulin at a dose of 0.1 mg/kg. FIG. 1C shows the results of the combination treatment in which BAL101553 was administered at a dose of 20 mg/kg and eribulin at a dose of 0.5 mg/kg. FIG. 1D shows the results of the combination treatment in which BAL101553 was administered at a dose of 30 mg/kg or 25 mg/kg and eribulin at a dose of 0.1 mg/kg. FIG. 1E shows the results of the combination treatment in which BAL101553 was administered at a dose of 30 mg/kg or 25 mg/kg and eribulin at a dose of 0.5 mg/kg. In each Figure the upper panel shows mean tumor volumes and the lower panel shows mean body weight changes. Data points represent mean values+/−SEM (n=8 animals).

FIG. 2 shows the results of a second experiment comparing the efficacy and tolerability of the combination of BAL101553 with eribulin versus the respective monotherapies in mice bearing the human TNBC tumour MDA-MB231 xenograft. BAL101553 was administered orally daily and eribulin intravenously every second day. In the combined regimen groups eribulin was administered 30 minutes before BAL101553 when administered on the same day. Control animals received vehicle control according to the applied single agent application schedules respectively. FIG. 2A shows the results of each of the single agent treatments. FIG. 2B shows the results of the combination treatment in which BAL101553 was administered at a dose of 25 mg/kg or 20 mg/kg and eribulin at a dose of 0.1 mg/kg. FIG. 2C shows the results of the combination treatment in which BAL101553 was administered at a dose of 25 mg/kg or 20 mg/kg and eribulin at a dose of 0.25 mg/kg. FIG. 2D shows the results of the combination treatment in which BAL101553 was administered at a dose of 20 mg/kg and eribulin at a dose of 0.5 mg/kg. In each Figure the upper panel shows mean tumor volumes and lower panel shows mean body weight changes. Data points represent mean values +/−SEM (n=10 animals).

FIG. 3 shows the effect of BAL27862 combined with Eribulin on the time-dependent induction of apoptosis in Jurkat-GFP cells. Exponentially growing Jurkat-GFP cells were cultivated in 96-well U-bottom plates and incubated with the indicated concentrations of BAL27862, eribulin or both compounds using standard cell culture conditions. Cells were removed and subjected to fluorescence-activated cell sorting (FACS) analysis after 24 hours, 48 hours, 72 hours and 96 hours in order to determine the percentage of cells that were apoptotic. The dotted line indicates the predictive (pot) additive activity.

FIG. 7 shows a schematic representation of the dosage regime of BAL101553 and eribulin administered to the in vivo subcutaneous mouse xenograft model MDA-MB-231 derived from human triple negative breast cancer (TNBC) as described in Example 1A.

FIG. 8 shows a schematic representation of the dosage regime of BAL101553 and eribulin administered to the in vivo subcutaneous mouse xenograft model MDA-MB-231 derived from human TNBC as described in Example 1B.

DETAILED DESCRIPTION OF THE INVENTION

Definitions

Figure 4:
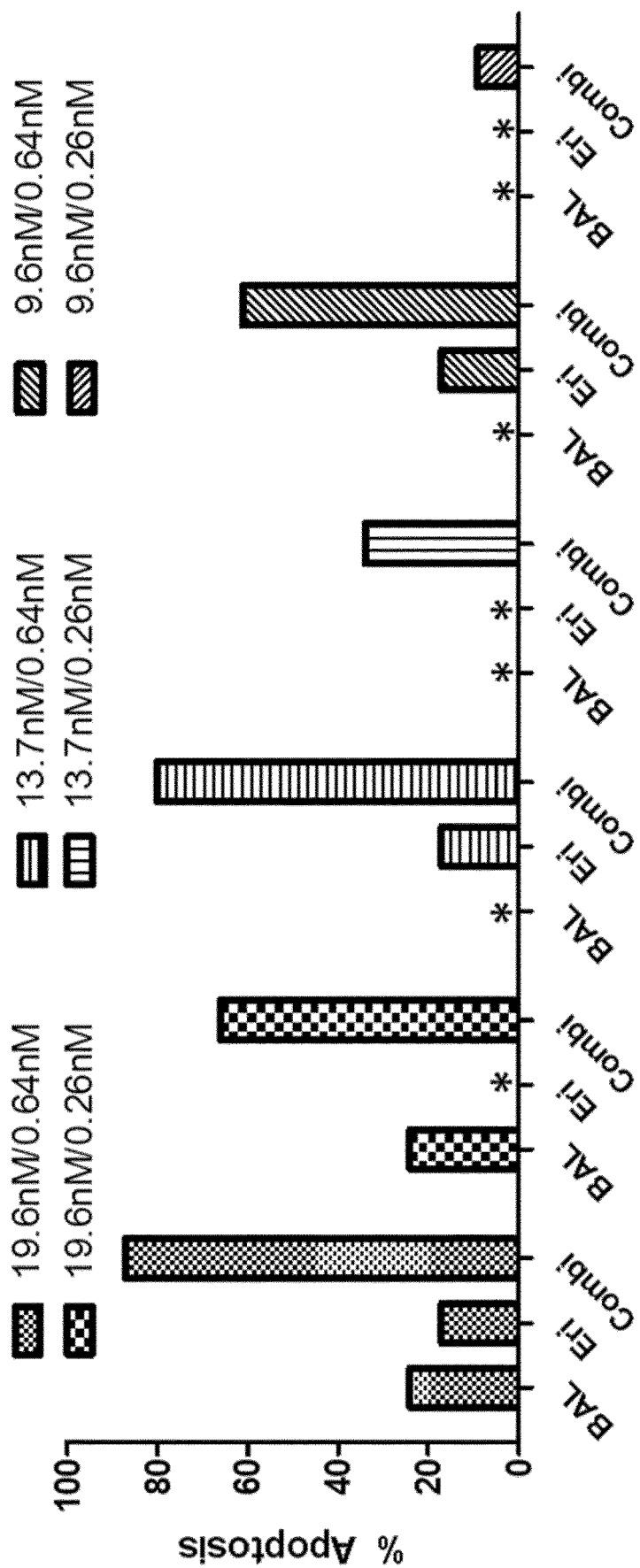
FIG. 4 shows effect of BAL27862 combined with eribulin on the induction of apoptosis in H460-GFP cells at the various concentrations shown. H460-GFP cells were incubated for 72 hours with the indicated concentrations of BAL27862, eribulin or both agents, harvested and measured by FACS for the induction of apoptosis and analyzed by using BD CellQuest™ Pro Software. "BAL" indicates treatment with BAL27862 alone, "Eri" indicates treatment with eribulin alone and "Combi" indicates a combined treatment of BAL27862 and eribulin. The concentrations of BAL27862 and eribulin used in the single agent treatments were the same as in the combined treatment for each experiment and are indicated in the Figure, with the concentration of BAL27862 indicated first followed by the concentration of eribulin. The asterix * indicates that no induction of apoptosis was observed.

Certain terms used herein are described below. Compounds of the present invention are described using standard nomenclature. Unless defined otherwise, all technical and scientific terms used herein have the same meaning as is commonly understood by one of skill in the art to which this invention belongs.

The term derivative or derivatives in the phrase "pharmaceutically acceptable derivative" or "pharmaceutically acceptable derivatives" of compounds of formula I relates to pharmaceutically acceptable salts, pro-drugs and pharmaceutically acceptable salts of pro-drugs thereof.

The term "combination," "therapeutic combination," or "pharmaceutical combination" as used herein refer to either a fixed combination in one dosage unit form, or non-fixed combination, or a kit, e.g. a kit of parts, for the combined administration where two or more therapeutic agents may be administered independently, at the same time or separately within time intervals, especially where these time intervals allow that the combination partners show a cooperative, e.g. synergistic, effect. Usually components (a) and (b) will be provided as separate dosage forms for independent administration.

The term "combination therapy" refers to the administration of two or more therapeutic agents to treat a therapeutic condition or disorder described in the present disclosure. Such administration encompasses co-administration of these therapeutic agents in a substantially simultaneous manner as well as use of each type of therapeutic agent in a sequential and/or separate manner (e.g. according to different administration routes), either at approximately the same time or at different times, e.g. according to different dosage regimens. When the therapeutic agents are administered sequentially and/or separately the dosing schedules will be such that there is a therapeutic interaction between the therapeutic agents within the patient's body and/or that a therapeutic effect resulting from the first therapeutic agent is present when the second therapeutic agent is administered. For example, when the agents are administered according to cyclic treatment schedules, the cyclic treatment schedules may overlap, or when one therapeutic agent is administered according to a continuous dosing schedule and the second according to a cyclic schedule, then at least one dose from the agent administered according to the continuous schedule will occur during the treatment cycle of the other therapeutic agent. Usually there will be at least one interval of no more than seven days between doses of the two therapeutic agents.

The term "pharmaceutical composition" is defined herein to refer to a solid or liquid formulation containing at least one therapeutic agent to be administered to a subject, e g a mammal in particular a human, optionally with one or more pharmaceutically acceptable excipients, in order treat a particular disease or condition affecting the subject.

The term "pharmaceutically acceptable" as used herein refers to items such as compounds, materials, compositions and/or dosage forms, which are, within the scope of sound medical judgment, suitable for contact with the tissues of a warm-blooded animal, e.g. a mammal in particular a human, without excessive toxicity or other complications commensurate with a reasonable benefit/risk ratio.

The terms "fixed combination," "fixed dose," and "single formulation" as used herein refers to a single carrier or vehicle or dosage form formulated to deliver an amount, which is jointly therapeutically effective for the treatment of neoplastic diseases, of both therapeutic agents to a patient. The single vehicle is designed to deliver an amount of each of the agents, along with any pharmaceutically acceptable carriers or excipients.

The term "non-fixed combination,", "kit", and "separate formulations" means that the active ingredients, i.e., the compound of formula I or pharmaceutically acceptable derivative and compound of formula II (eribulin, e.g. eribulin mesylate), are both administered to a patient as separate entities either simultaneously, concurrently or sequentially, wherein such administration provides therapeutically effective levels of the two compounds in the body of the subject in need thereof.

The term "treatment" as used herein in the context of treating a neoplastic disease in a patient pertains generally to treatment and therapy in which some desired therapeutic effect is achieved, for example one or more of the following: the inhibition of the progress of the neoplastic disease, a reduction in the rate of progress, a halt in the rate of progress, a prevention of the progression of the neoplastic disease, alleviation of symptoms of the neoplastic disease, amelioration of neoplastic disease, and cure of the neoplastic disease. For example, treatment can be the diminishment of one or several symptoms of a disorder or complete eradication of a disorder, such as cancer. Within the meaning of the present disclosure, the term "treat" also denotes to arrest, delay the onset (i.e., the period prior to clinical manifestation of a disease) and/or reduce the risk of developing or worsening a disease.

The term "prevent", "preventing" or "prevention" as used herein comprises the prevention of at least one symptom associated with or caused by the state, disease or disorder being prevented.

The term "pharmaceutically effective amount," "therapeutically effective amount," or "clinically effective amount" of a combination of therapeutic agents is an amount sufficient to provide an observable or clinically significant improvement over the baseline clinically observable signs and symptoms of the disorders treated with the combination.

The term "subject" or "patient" as used herein is intended to include animals, which are capable of suffering from or afflicted with a neoplastic disease such as a cancer or any disorder involving, directly or indirectly, a neoplastic disease such as a cancer. Examples of subjects include mammals, e.g. humans, apes, monkeys, dogs, cows, horses, pigs, sheep, goats, cats, mice, rabbits, rats, and transgenic non-human animals. Preferably, the subject is a human, e.g. a human suffering from, at risk of suffering from neoplastic diseases such as cancers.

The term "therapeutically-effective amount," as used herein, pertains to that amount of a therapeutic agent, or a material, composition or dosage form comprising a therapeutic agent, which is effective for producing some desired therapeutic effect, commensurate with a reasonable benefit/risk ratio, when administered in accordance with a desired treatment regimen. The skilled person will understand that the therapeutically effective amount of an agent for use in combination therapy may be lower than the amount required to provide a therapeutic effect when using the agent as a monotherapy.

The term "about" means a variation of no more than 10% of the relevant figure, preferably no more than 5%.

For convenience, reference to the compound of formula I refers to the compound e.g. in free form and pharmaceutically acceptable salts thereof. Reference to derivatives of the compound of formula I refers to the derivatives e.g. in free form and pharmaceutically acceptable salts of said derivatives. Likewise, reference to the compound of formula II (eribulin) refers to the compound e.g. in free form and pharmaceutically acceptable salts thereof and in particular the mesylate salt.

All possible solvates and complexes (including hydrates) of the compound of formula I and derivatives thereof as well as any polymorphs of the compound of formula I and derivatives thereof, including amorphous solids, as well as pharmaceutically acceptable salts of any of the foregoing are included within the scope of the invention. Likewise all possible solvates and complexes (including hydrates) of the compound of formula II as well as any polymorphs of the compound of formula I and derivatives thereof, including amorphous solids, as well as pharmaceutically acceptable salts of any of the foregoing are included within the scope of the invention.

Compound of Formula I and Derivatives Thereof

In some embodiments R is phenyl or phenyl substituted by one or two substituents independently selected from, methyl, ethyl, propyl, iso-propyl, methoxy, ethoxy, hydroxyl, amino, methylamino, ethylamino, dimethylamino, diethylamino, acetylamino, halogen (e.g. F, Cl or Br) and nitro.

In some embodiments R is pyridinyl or pyridinyl substituted by a single substituent selected from amino, F, Cl or Br.

In some embodiments R is phenyl or pyridinyl substituted by amino.

In some embodiments $R^1$ is H or cyanoethyl.

Preferred compounds of formula I include those wherein R and $R^1$ are defined as follows:

| R | $R^1$ |
|---|---|
| 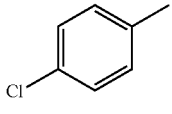 | H |
| 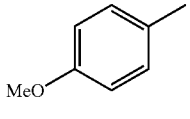 | H |
| 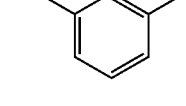 | H |
| 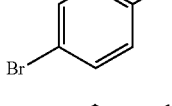 | H |
| 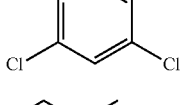 | H |
| 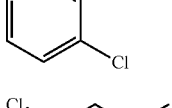 | H |
| 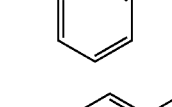 | H |
| 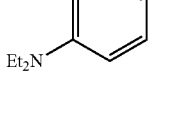 | H |

-continued

| R | $R^1$ |
|---|---|
| 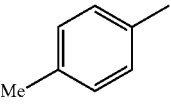 | H |
| 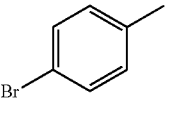 | $CH_2CH_2CN$ |
| 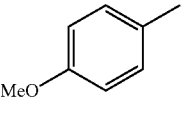 | $CH_2CH_2CN$ |
| 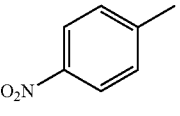 | H |
| 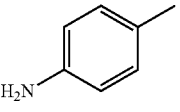 | H |
| 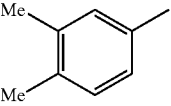 | H |
| 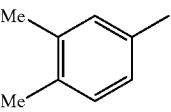 | $CH_2CH_2CN$ |
| 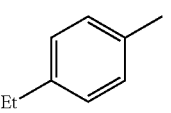 | H |
| 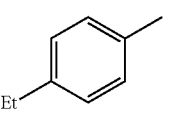 | $CH_2CH_2CN$ |
| 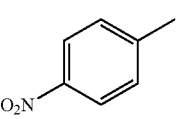 | $CH_2CH_2CN$ |
| 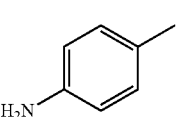 | $CH_2CH_2CN$ |
| 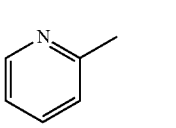 | H |
| AcNH— (phenyl) | H |

| R | R¹ |
|---|---|
| 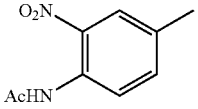 | H |
| 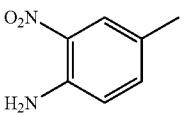 | H |
| 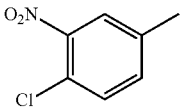 | H |
| 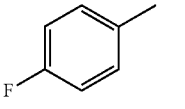 | H |
| 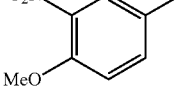 | H |
| 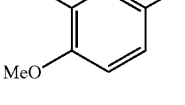 | $CH_2CH_2CN$ |
| 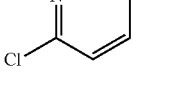 | H |
| 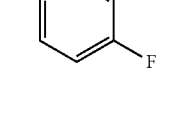 | H |
| 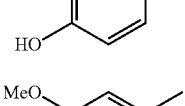 | H |
| 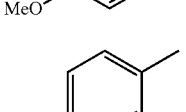 | H |
|  | H |
| 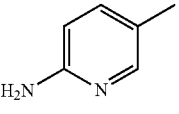 | $CH_2CH_2CN$ |
| 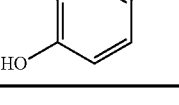 | H | or pharmaceutically acceptable derivative thereof.

Especially preferred are compounds wherein R and R¹ are defined as follows:

| R | R¹ |
|---|---|
| 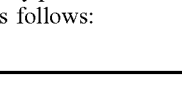 | H |
| 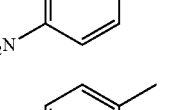 | $CH_2CH_2CN$ |
| 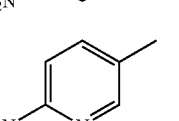 | H |
| 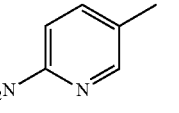 | $CH_2CH_2CN$ | or pharmaceutically acceptable derivative thereof.

An especially preferred compound is the compound of formula I-A or pharmaceutically acceptable derivative thereof:

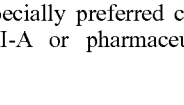

(I-A)

In some embodiments the compound of the formula I is the compound of formula I-A, or a pharmaceutically acceptable salt thereof.

In some embodiments the compound of the formula I is a prodrug of the compound of formula I-A, or a pharmaceutically acceptable salt of the prodrug.

Salts of the compound of formula I may be acid addition salts. Salts are formed, e.g. with organic or inorganic acids, from compounds of formula I or pharmaceutically acceptable derivatives thereof with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

The compound of formula I may be administered in the form of a pharmaceutically acceptable derivative. Suitably the compound of formula I, in particular the compound of formula I-A, is administered in the form of a pro-drug, including pharmaceutically acceptable salts thereof, which is broken down in the subject (e.g. human) to give a compound of the formula I. Examples of pro-drugs include in vivo hydrolysable esters and amides of a compound of the formula I. Particular pro-drugs considered are ester and amides of naturally occurring amino acids and ester or amides of small peptides, in particular small peptides consisting of up to five, preferably two or three amino acids as well as esters and amides of pegylated hydroxy acids, preferably hydroxy acetic acid and lactic acid. Pro-drug esters may be formed from the acid function of the amino acid or the C terminal of the peptide and suitable hydroxy group(s) in the compound of formula I. Pro-drug amides may be formed from the acid function of the amino acid or the C terminal of the peptide and suitable amino group(s) in the compound of formula I. In particular, the pro-drug amides are formed from the amino group(s) present within the R group of formula I, e.g. the pro-drug is an amide formed from an amino group present within the R group of the compound of formula I as defined above and the carboxy group of glycine, alanine or lysine.

The compound of formula I may be in the form of a pro-drug selected from the compounds of the following formulae and pharmaceutically acceptable salts thereof:

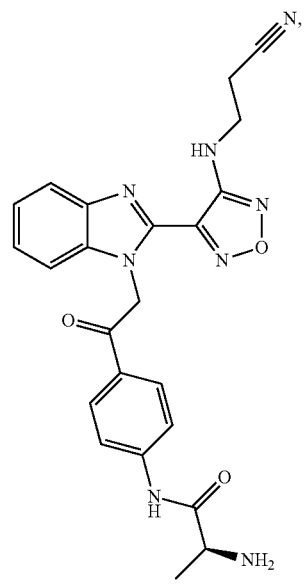

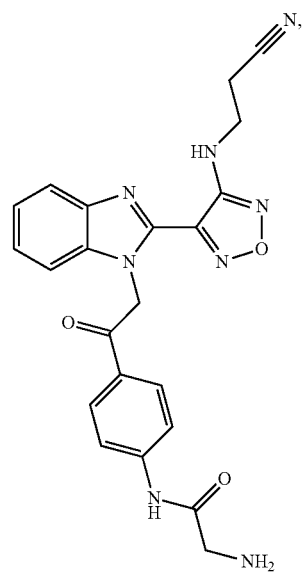

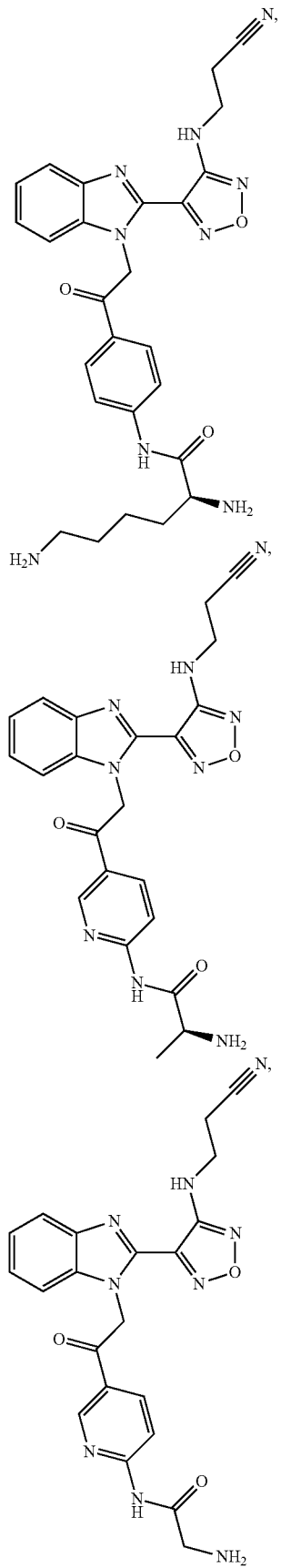
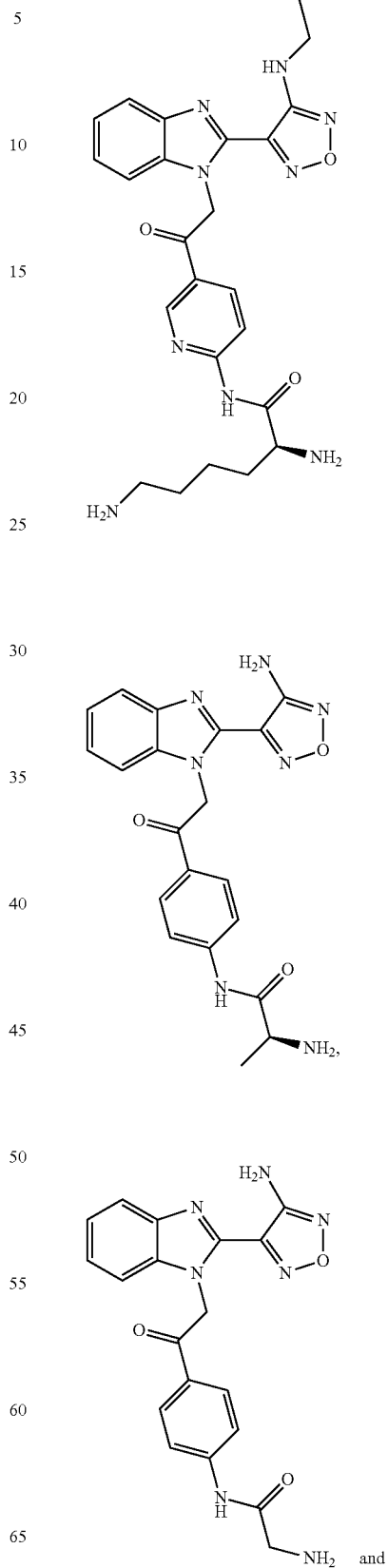

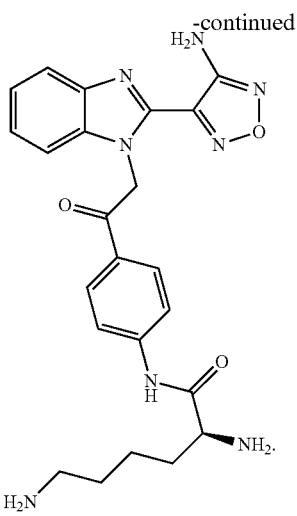

When the compound of formula I is provided as a pro-drug it is preferably the compound of formula I-B or a pharmaceutically acceptable salt thereof, e.g. a hydrochloride salt such as a dihydrochloride salt.

Reference to a compound of formula I or pharmaceutically acceptable derivative thereof preferably refers to a compound of formula I-A or pharmaceutically acceptable salt thereof, or a compound of formula I-B or pharmaceutically acceptable salt thereof.

The compounds of formula I may be prepared as described in WO2004/103994, which is hereby incorporated by reference. The derivatives of the compound of formula I, in particular the pro-drugs of the compound of formula I, may be prepared as described for example in WO2011/012577, in particular on pages 29 to 39, which is hereby incorporated by reference.

Compound of Formula II (Eribulin)

The terms "compound of formula II" and "eribulin" are used herein interchangeably. Methods for the synthesis of eribulin are described, for example, in U.S. Pat. Nos. 6,214,865; 7,982,060; 8,350,067; and 8,093,410, each of which is incorporated herein by reference. Eribulin mesylate is available commercially and is marketed as HALAVEN®.

Salts of the compound of formula II can be selected from, for example, mesylic acid salt (e.g. eribulin mesylate), hydrochloric acid salt, sulfuric acid salt, citrate, hydrobromic acid salt, hydroiodine acid salt, nitric acid salt, bisulfate, phosphoric acid salt, super phosphoric acid salt, isonicotinic acid salt, acetic acid salt, lactic acid salt, salicic acid salt, tartaric acid salt, pantotenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt, ethanesulfonic acid salt, benzenesulfonic acid salt, p-toluenesulfonic acid salt, pamoic acid salt (pamoate), and so on. Moreover, it is acceptable to use a salt of aluminium, calcium, lithium, magnesium, sodium, zinc and diethanolamine. There are no particular limitations as to the salt used, whether inorganic acid salt or organic acid salt. The preferred (and commercially available) salt of the compound of formula II is the mesylate salt, i.e. eribulin mesylate.

Diseases

The pharmaceutical combinations of the invention may be used to treat neoplastic diseases by administration of the combinations of the invention, e.g. to destabilize of microtubules. In addition, the pharmaceutical combinations of the invention may be used to treat a cancer at any clinical stage or pathological grade (e.g. tumour stage I, tumour stage II, tumour stage III, tumour stage IV) or treatment settings (e.g. preventative, adjuvant, neoadjuvant, therapeutic including palliative treatment). The pharmaceutical combinations of the invention may be for use in slowing, delaying or stopping cancer progression or cancer growth or increasing the overall survival time or the cancer-progression-free survival time or the time to progression of a cancer or improving or maintaining the patient's quality of life or functional status. The pharmaceutical combinations of the invention may also be used in post-therapy recovery from cancer.

For example, the pharmaceutical combinations of the invention of the invention may be used for (i) reducing the number of cancer cells; (ii) reducing tumour volume; (iii) increasing tumour regression rate; (iv) reducing or slowing cancer cell infiltration into peripheral organs; (v) reducing or slowing tumour metastasis; (vi) reducing or inhibiting tumour growth; (vii) preventing or delaying occurrence and/or recurrence of the cancer and/or extends disease- or tumour-free survival time; (viii) increasing overall survival time; (ix) reducing the frequency of treatment; and/or (x) relieving one or more of symptoms associated with the cancer.

As mentioned above, the pharmaceutical combinations of the invention may be used for the therapeutic treatment of neoplastic diseases. Examples of neoplastic diseases include, but are not limited to, epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, miscellaneous myeloproliferative disorders, lymphoproliferative disorders and myelodysplastic syndromes.

In one embodiment the neoplastic disease is cancer. Examples of cancers in terms of the organs and parts of the body affected include, but are not limited to, the brain, breast (including triple negative breast cancer), cervix, ovaries, colon, rectum, (including colon and rectum i.e. colorectal cancer), lung, (including small cell lung cancer, non-small cell lung cancer, large cell lung cancer and mesothelioma), endocrine system, bone, adrenal gland, thymus, liver, stomach, intestine, (including gastric cancer), pancreas, bone marrow, haematological malignancies, (such as lymphoma, leukaemia, myeloma or lymphoid malignancies), bladder, urinary tract, kidneys, skin, thyroid, head, neck, prostate and testis.

For example, the cancer may be selected from the group consisting of brain cancer (e.g. neuroblastoma, glioblastoma), breast cancer (including triple negative breast cancer), prostate cancer, cervical cancer, ovarian cancer, gastric cancer, colorectal cancer, pancreatic cancer, liver cancer, neuroendocrine cancer, lung cancer, kidney cancer, haematological malignancies, melanoma and sarcomas (including soft tissue sarcomas, e.g. liposarcoma).

The cancer may be for example a primary tumour, or metastases, derived for example from a solid or liquid tumour. In one embodiment the neoplastic disease (e.g. cancer) to be treated is a tumour, preferably a solid tumour.

In a further embodiment the neoplastic disease is a brain neoplasm, e.g. a brain tumour, which include but are not limited to glial- and non-glial-tumours, astrocytomas (incl. glioblastoma multiforme and unspecified gliomas), oligodendrogliomas, ependydomas, menigiomas, haemangioblastomas, acoustic neuromas, craniopharyngiomas, primary central nervous system lymphoma, germ cell tumours, pituitary tumours, pineal region tumours, primitive neuroectodermal tumours (PNET's), medullablastomas, haemangiopericytomas, spinal cord tumours including meningiomas, chordomas and genetically-driven brain neoplasms including neurofibromatosis, peripheral nerve sheath tumours and tuberous sclerosis.

In a further embodiment the cancer is brain cancer (e.g. neuroblastoma, glioblastoma).

In a further embodiment the cancer is breast cancer (including triple negative breast cancer, hormone receptor positive breast cancer and HER2 positive breast cancer).

In a further embodiment the cancer is prostate cancer.

In a further embodiment the cancer is cervical cancer.

In a further embodiment the cancer is ovarian cancer.

In a further embodiment the cancer is gastric cancer.

In a further embodiment the cancer is colorectal cancer.

In a further embodiment the cancer is pancreatic cancer.

In a further embodiment the cancer is liver cancer.

In a further embodiment the cancer is neuroendocrine cancer.

In a further embodiment the cancer is lung cancer.

In a further embodiment the cancer is kidney cancer.

In a further embodiment the cancer is haematological malignancies.

In a further embodiment the cancer is melanoma.

In a further embodiment the cancer is a sarcoma.

In a further embodiment the cancer is a breast cancer selected from ER+, PR+, HER2+. ductal carcinoma in situ (DCIS), lobular carcinoma in situ (LCIS) and in particular metastatic breast cancer such as triple negative breast cancer.

Administration

Administration of the pharmaceutical combinations of the invention includes administration of the combination in a single formulation or unit dosage form, as well as administration of the individual agents of the combination in separate formulations or separate dosage forms.

The present invention particularly pertains to a combination of the invention for treating cancer. In an embodiment, the combination of the invention is used for the treatment of cancer comprising administering to the subject a combination therapy, comprising a therapeutically effective amount of a compound of formula I (e.g. the compound of formula I-A or pharmaceutically acceptable salt thereof) or pharmaceutically acceptable derivative thereof (e.g. the compound of formula I-B or pharmaceutically acceptable salt thereof), and a therapeutically effective amount of the compound of formula II or a pharmaceutically acceptable salt thereof (e.g. eribulin mesylate). These compounds are administered at therapeutically effective dosages, which when combined may provide a beneficial effect e.g. as described herein. The skilled person will understand that therapeutically effective dosages for use in combination therapy may be lower than the dosages required to provide a therapeutic effect when using either agent as a monotherapy.

The administration of a pharmaceutical combination of the invention may result not only in a beneficial effect, e.g. a synergistic effect, e.g. with regard to alleviating, delaying progression of or inhibiting the symptoms, but may also result in further beneficial effects, e.g. fewer side-effects, more durable therapeutic effect, an improved quality of life or a decreased morbidity, compared with a monotherapy applying only one of the pharmaceutically therapeutic agents used in the combination of the invention. It may also be the case that lower doses of the therapeutic agents of the combination of the invention can be used, for example, such that the dosages may not only often be smaller, but also may be applied less frequently, or can be used in order to diminish the incidence of side-effects observed with one of the combination partners alone.

In an embodiment, the combination provided herein may display a synergistic effect. The term "synergistic effect" as used herein, refers to action of two agents such as, for example, the compound of formula I (e.g. the compound of formula I-A or pharmaceutically acceptable salt thereof) or pharmaceutically acceptable derivative thereof (e.g. the compound of formula I-B or pharmaceutically acceptable salt thereof) and a compound of formula II or pharmaceutically acceptable salt thereof (e.g. eribulin mesylate), to produce a therapeutic effect, e.g. slowing the progression of a neoplastic disease such as cancer or symptoms thereof, which is greater than the addition of the same therapeutic effect of each drug administered on its own.

Generally, in determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in certain experiments can be predictive of the effect in other species, and animal models may be used to further quantify a synergistic effect. The results of such studies can also be used to predict effective dose ratio ranges and the absolute doses and plasma concentrations, e.g. as illustrated in the Examples below. In one embodiment, synergy may be confirmed following the procedure described in Example 2B. For example, synergy is present when the amount of apoptosis of Jurkat-GFP or NCI-H460-GFP cells from the combination is greater than the sum of the apoptosis from each agent alone when each agent is used at a concentration which is lower than the respective EC50 concentration. For example, each agent may be used at a concentration which is half of the respective EC50 concentration. The EC50 concentration is the concentration at which the agent induces 50 percent apoptosis as determined by a dose-response curve.

In a further embodiment, the present invention provides a synergistic combination for administration to humans comprising the pharmaceutical combination of the invention, where the dose range of each component corresponds to the synergistic ranges, e.g. as indicated in a suitable tumour model or clinical study.

The combinations of the present invention can be used in long-term therapy or as an adjuvant therapy in the context of other treatment strategies, as described above. Other possible treatments are therapy to maintain the patient's status after tumour regression, or even preventive therapy, for example in patients at risk.

The compound of formula I or pharmaceutically acceptable derivative thereof and the compound of formula II or pharmaceutically acceptable salt thereof may be administered according to the same treatment schedule or may be administered according to independent treatment schedules. The treatment schedules may be cyclic or continuous.

A cyclic treatment schedule is defined by a repeated dosing schedule wherein the repeated element (a cycle) has a specific duration and wherein doses are administered on specific days within the cycle. A cycle may incorporate a period, usually at the end of the cycle, in which there is no administration (a "rest period"), e.g. to allow a period for recovery. A treatment cycle may be, e.g. 7 days, 14 days, 21 days, 28 days or longer. For example, the Federal Drug Administration and European Medicines Agency have recommended that eribulin is administered on days 1 and 8 of a 21-day treatment cycle. Accordingly, in this example of a cyclic treatment schedule the eribulin is administered once per week for two weeks followed by a rest period of 1 week (i.e. no eribulin is administered on days 9 to 21 of the cycle). If the cycle is repeated further eribulin would be administered according to the cycle on the day following day 21 of the cycle.

A continuous treatment schedule is a regular dosing schedule which does not incorporate rest periods (i.e. periods that are longer than the regular interval between the doses). For example doses may be administered once per day, twice per day, once every two days, once every three days etc.

The treatment schedule, whether cyclic or continuous may be continued for as long as required (an "open-end treatment") e.g. as long as the patient is receiving benefit judged by a physician overseeing the treatment.

When the compound of formula I or pharmaceutically acceptable derivative thereof and the compound of formula II or pharmaceutically acceptable salt thereof are administered according to independent treatment schedules, the treatment schedules may both be cyclic, or one may be cyclic and the other may be continuous. When both treatment schedules are cyclic, the cycles of the two treatment schedules may be of the same duration or may be of different duration, and they may start on the same day or may start on different days.

In another embodiment the compound of formula I or pharmaceutically acceptable derivative thereof is administered according to a continuous treatment schedule, and the compound of formula II or pharmaceutically acceptable salt thereof is administered according to a cyclic treatment schedule wherein each cycle has a duration of 21 days. The treatment schedules may start on the same day or may start on different days.

In another embodiment the compound of formula I or pharmaceutically acceptable derivative thereof is administered according to a continuous treatment schedule, and the compound of formula II or pharmaceutically acceptable salt thereof is administered according to a cyclic treatment schedule wherein each cycle has a duration of 28 days. The treatment schedules may start on the same day or may start on different days.

In another embodiment the compound of formula I or pharmaceutically acceptable derivative thereof and the compound of formula II or pharmaceutically acceptable salt thereof are both administered according to a cyclic treatment schedule wherein each cycle has a duration of 21 days, and which treatment schedules may start on the same day or may start on different days.

In another embodiment the compound of formula I or pharmaceutically acceptable derivative thereof is administered according to a cyclic treatment wherein each cycle has a duration of 28 days, and the compound of formula II or pharmaceutically acceptable salt thereof is administered according to a cyclic treatment schedule wherein each cycle has a duration of 21 days. The treatment schedules may start on the same day or may start on different days.

In another embodiment the compound of formula I or pharmaceutically acceptable derivative thereof and the compound of formula II or pharmaceutically acceptable salt thereof are both administered according to a cyclic treatment schedule wherein each cycle has a duration of 28 days, and which treatment schedules may start on the same day or may start on different days.

Additional embodiments are provided in Table A below.

TABLE A

| Embodiment | Compound of formula IA or pharmaceutically acceptable salt thereof or compound of formula IB or pharmaceutically acceptable salt thereof | Compound of formula II or pharmaceutically acceptable salt thereof |
|---|---|---|
| 1A | Oral administration: continuous treatment schedule, dosing every day | IV administration: cyclic treatment schedule, 21-day treatment cycle, dosing initiated on days 1 and 8 |
| 2A | Oral administration: continuous treatment schedule, dosing every day | IV administration: cyclic treatment schedule, 28-day treatment cycle, dosing initiated on days 1 and 15 |
| 3A* | IV administration: cyclic treatment schedule, 21-day treatment cycle, dosing initiated on days 1 and 8 | IV administration: cyclic treatment schedule, 21-day treatment cycle, dosing initiated on days 1 and 8 |
| 4A* | IV administration: cyclic treatment schedule, 28-day treatment cycle, dosing initiated on days 1, 8 and 15 | IV administration: cyclic treatment schedule, 21-day treatment cycle, dosing initiated on days 1 and 8 |
| 5A* | IV administration: cyclic treatment schedule, 21-day treatment cycle, dosing initiated on days 1 and 8 | IV administration: cyclic treatment schedule, 28-day treatment cycle, dosing initiated on days 1 and 15 |
| 6A* | IV administration: cyclic treatment schedule, 28-day treatment cycle, dosing initiated on days 1, 8 and 15 | IV administration: cyclic treatment schedule, 28-day treatment cycle, dosing initiated on days 1 and 15 |

*Where cyclic treatment schedules are used for both combination partners, cycles may or may not start on the same day Examples of mole dosage ratios (i.e. number of moles: number of moles) of the compound of formula I or pharmaceutically acceptable derivative thereof to the compound of formula II or pharmaceutically acceptable salt thereof include e.g. 1:1 to 800:1, e.g. 2:1 to 800:1, e.g. 5:1 to 800:1, e.g. 5:1 to 500:1, e.g. 20:1 to 300:1, e.g. 30:1 to 250:1, e.g. 50:1 to 250:1, e.g. 30:1 to 150:1. For example the mole:mole ratio of the compound of formula I or pharmaceutically acceptable derivative thereof to the compound of formula II or pharmaceutically acceptable salt thereof may be e.g. at least 1:1, e.g. at least 2:1, e.g. at least 5:1, e.g. at least 10:1, e.g. at least 20:1, e.g. at least 30:1, e.g. at least 40:1, e.g. at least 50:1. For example the mole:mole ratio of the compound of formula I or pharmaceutically acceptable derivative thereof to the compound of formula II or pharmaceutically acceptable salt thereof may be e.g. up to 800:1, e.g. up to 500:1, e.g. up to 400:1, e.g. up to 300:1, e.g. up to 250:1 e.g. up to 200:1, e.g. up to 150:1.

If a cyclic treatment schedule is used for both combination partners and the cycles are of the same duration then the mole ratio is the ratio of the total mole amount of the doses of the compound of formula I or pharmaceutically acceptable derivative thereof to the total mole amount of the doses of the compound of formula II or pharmaceutically acceptable salt thereof administered to the subject over the respective cycles.

If a cyclic treatment schedule is used for both combination partners and the cycles are of different duration then the mole ratio is the ratio of the total mole amount of the doses of the compound of formula I or pharmaceutically acceptable derivative thereof to the total mole amount of the doses of the compound of formula II or pharmaceutically acceptable salt thereof administered to the subject over a theoretical period of time corresponding to a common multiple of the duration of the respective treatment cycles. For example if one combination partner is administered according to a three-week cycle and the other combination partner is administered according to a four-week cycle, then the total number of administrations over a 12-week period (i.e. three cycles of the four week cycle and four cycles of the three week cycle) will be used to determine the mole ratio.

If a continuous treatment schedule is used for one combination partner and a cyclic treatment schedule is used for the other combination partner then the mole ratio is the ratio of the total mole amount of the doses of the combination partner administered to the subject according to a continuous treatment over a period of the same duration of one cycle of the other combination partner to the total mole amount of the doses of the other combination partner administered to the subject over the treatment cycle. For example if the treatment cycle of one of the combination partners has a duration of 21 days, then for the determination of the mole ratio the total mole amount of the doses of the other combination partner over a period of 21 days is used, e.g. if administered once every two days, then the sum of the mole amount of 11 doses will be used for the determination of the mole ratio. In the event that the arrangement of the dosing schedules leads to the possibility of different numbers of doses of the continuous treatment over the duration of the cycle of the cyclic treatment, then the larger number of doses of the continuous treatment is used for the determination of the mole ratio.

If a continuous treatment schedule is used for both combination partners, then the respective total mole amount of the doses over a period of seven days is used to determine the mole ratios. For example if one combination partner is administered once every two days and the other is administered once every seven days, then for the determination of the above ratios, the sum of the mole amount of four doses of the first combination partner versus one dose of the second combination partner is used to determine the mole ratio.

Examples of weight:weight dosage ratios of the compound of formula I-B (in the form of the dihydrochloride salt) to the compound of formula II (in the form of eribulin mesylate) may be e.g. 1:1 to 600:1, e.g. 2:1 to 600:1, e.g. 4:1 to 600:1, e.g. 4:1 to 350:1, e.g. 10:1 to 250:1, e.g. 20:1 to 200:1, e.g. 30:1 to 200:1, e.g. 20:1 to 120:1. For example, the weight:weight dosage ratio of the compound of formula I-B (in the form of the dihydrochloride salt) to the compound of formula II (in the form of eribulin mesylate) may be e.g. at least 1:1, e.g. at least 2:1, e.g. at least 4:1, e.g. at least 10:1, e.g. at least 15:1, e.g. at least 20:1, e.g. at least 25:1, e.g. at least 30:1. For example, the weight:weight dosage ratio of the compound of formula I-B (in the form of the dihydrochloride salt) to the compound of formula II (in the form of eribulin mesylate) may be e.g. up to 600:1, e.g. up to 350:1, e.g. up to 300:1, e.g. up to 250:1, e.g. up to 200:1, e.g. up to 150:1, e.g. up to 120:1. When the compound of formula I-B is provided in a form other than the dihydrochloride salt, e.g. as a different pharmaceutically acceptable salt, and/or when eribulin is provided in a form other than the mesylate salt, e.g. as a different pharmaceutically acceptable salt, then the corresponding weight:weight ratios giving the same mole:mole ratio apply, based on the respective molecular weights. The molecular weight of the dihydrochloride salt of the compound of formula I-B is 588.5 Da and the molecular weight of eribulin mesylate is 826.0 Da.

The weight:weight dosage ratios are determined according to the same methodology as given for mole dosage ratios described above, i.e. the ratio of the total weight amount of the doses of the compound of formula I or pharmaceutically acceptable derivative thereof to the total weight amount of the doses of the compound of formula II or pharmaceutically acceptable salt thereof over the respective treatment cycles, when cyclic treatment schedules are used for both combination partners. Likewise, if a continuous treatment schedule is used for one combination partner and a cyclic treatment schedule is used for the other combination partner then the total weight amount of the doses of the continuous treatment over a period of the same duration of the treatment cycle of the other combination partner is used to determine the weight:weight ratio.

Examples of weight:weight dosage ratios of the compound of formula I-A (in free form) to the compound of formula II (in the form of eribulin mesylate) may be e.g. 0.5:1 to 400:1, e.g. 1:1 to 400:1, e.g. 2:1 to 400:1, e.g. 2:1 to 250:1, e.g. 5:1 to 150:1, e.g. 10:1 to 120:1, e.g. 20:1 to 120:1, e.g. 10:1 to 80:1. For example the weight:weight dosage ratios of the compound of formula I-A (in free form) to the compound of formula II (in the form of eribulin mesylate) may be e.g. at least 0.5:1 e.g. at least 1:1, e.g. at least 2:1, e.g. at least 5:1, e.g. at least 10:1, e.g. at least 15:1, e.g. at least 20:1. For example the weight:weight dosage ratios of the compound of formula I-A (in free form) to the compound of formula II (in the form of eribulin mesylate) may be e.g. up to 400:1, e.g. up to 250:1, e.g. 200:1, e.g. up to 150:1, up to 120:1, e.g. up to 100:1, e.g. up to 80:1. Likewise, when the compound of formula I-A is provided in a form other than the free form, e.g. as a pharmaceutically acceptable salt or as a prodrug or salt thereof, and/or when eribulin is provided in a form other than the mesylate salt, e.g. as a different pharmaceutically acceptable salt, then corresponding weight:weight ratios giving the same mole:

mole ratio apply based on the respective molecular weights. The molecular weight of the free form of the compound of formula I-A is 387.4 Da and the molecular weight of eribulin mesylate is 826.0 Da. Similarly, the weight:weight dosage ratios are determined according to the same methodology as given for mole ratios above.

Additional embodiments of the invention are shown in Table B and Table C below.

TABLE B

| Embodiment | Combination partner I (CPI) | Combination partner II (CPII) | Mole ratio of CPI:CPII |
| --- | --- | --- | --- |
| 1B | I-A or pharmaceutically acceptable salt thereof or I-B or pharmaceutically acceptable salt thereof | Eribulin or pharmaceutically acceptable salt thereof | 1:1 to 800:1 |
| 2B | I-A or pharmaceutically acceptable salt thereof or I-B or pharmaceutically acceptable salt thereof | Eribulin or pharmaceutically acceptable salt thereof | 5:1 to 500:1 |
| 3B | I-A or pharmaceutically acceptable salt thereof or I-B or pharmaceutically acceptable salt thereof | Eribulin or pharmaceutically acceptable salt thereof | 20:1 to 300:1 |
| 4B | I-A or pharmaceutically acceptable salt thereof or I-B or pharmaceutically acceptable salt thereof | Eribulin or pharmaceutically acceptable salt thereof | 30:1 to 250:1 |
| 5B | I-A or pharmaceutically acceptable salt thereof or I-B or pharmaceutically acceptable salt thereof | Eribulin or pharmaceutically acceptable salt thereof | 50:1 to 250:1 |
| 6B | I-A or pharmaceutically acceptable salt thereof or I-B or pharmaceutically acceptable salt thereof | Eribulin or pharmaceutically acceptable salt thereof | 30:1 to 150:1 |
| 7B | I-B or pharmaceutically acceptable salt thereof | Eribulin or pharmaceutically acceptable salt thereof | 1:1 to 800:1 |
| 8B | I-B or pharmaceutically acceptable salt thereof | Eribulin or pharmaceutically acceptable salt thereof | 5:1 to 500:1 |
| 9B | I-B or pharmaceutically acceptable salt thereof | Eribulin or pharmaceutically acceptable salt thereof | 20:1 to 300:1 |
| 10B | I-B or pharmaceutically acceptable salt thereof | Eribulin or pharmaceutically acceptable salt thereof | 30:1 to 250:1 |
| 11B | I-B or pharmaceutically acceptable salt thereof | Eribulin or pharmaceutically acceptable salt thereof | 50:1 to 250:1 |
| 12B | I-B or pharmaceutically acceptable salt thereof | Eribulin or pharmaceutically acceptable salt thereof | 30:1 to 150:1 |
| 13B | I-B as dihydrochloride salt | Eribulin mesylate | 1:1 to 800:1 |

TABLE B-continued

| Embodiment | Combination partner I (CPI) | Combination partner II (CPII) | Mole ratio of CPI:CPII |
|---|---|---|---|
| 14B | I-B as dihydrochloride salt | Eribulin mesylate | 5:1 to 500:1 |
| 15B | I-B as dihydrochloride salt | Eribulin mesylate | 20:1 to 300:1 |
| 16B | I-B as dihydrochloride salt | Eribulin mesylate | 30:1 to 250:1 |
| 17B | I-B as dihydrochloride salt | Eribulin mesylate | 50:1 to 250:1 |
| 18B | I-B as dihydrochloride salt | Eribulin mesylate | 30:1 to 150:1 |

TABLE C

| Embodiment | Combination partner I (CPI) | Combination partner II (CPII) | Weight:weight ratio of CPI:CPII |
|---|---|---|---|
| 1C* | I-A or pharmaceutically acceptable salt thereof or I-B or pharmaceutically acceptable salt thereof | Eribulin or pharmaceutically acceptable salt thereof | 1:1 to 600:1 |
| 2C* | I-A or pharmaceutically acceptable salt thereof or I-B or pharmaceutically acceptable salt thereof | Eribulin or pharmaceutically acceptable salt thereof | 4:1 to 350:1 |
| 3C* | I-A or pharmaceutically acceptable salt thereof or I-B or pharmaceutically acceptable salt thereof | Eribulin or pharmaceutically acceptable salt thereof | 10:1 to 250:1 |
| 4C* | I-A or pharmaceutically acceptable salt thereof or I-B or pharmaceutically acceptable salt thereof | Eribulin or pharmaceutically acceptable salt thereof | 20:1 to 200:1 |
| 5C* | I-A or pharmaceutically acceptable salt thereof or I-B or pharmaceutically acceptable salt thereof | Eribulin or pharmaceutically acceptable salt thereof | 30:1 to 200:1 |
| 6C* | I-A or pharmaceutically acceptable salt thereof or I-B or pharmaceutically acceptable salt thereof | Eribulin or pharmaceutically acceptable salt thereof | 20:1 to 120:1 |
| 7C* | I-B or pharmaceutically acceptable salt thereof | Eribulin or pharmaceutically acceptable salt thereof | 1:1 to 600:1 |
| 8C* | I-B or pharmaceutically acceptable salt thereof | Eribulin or pharmaceutically acceptable salt thereof | 4:1 to 350:1 |
| 9C* | I-B or pharmaceutically acceptable salt thereof | Eribulin or pharmaceutically acceptable salt thereof | 10:1 to 250:1 |

TABLE C-continued

| Embodiment | Combination partner I (CPI) | Combination partner II (CPII) | Weight:weight ratio of CPI:CPII |
|---|---|---|---|
| 10C* | I-B or pharmaceutically acceptable salt thereof | Eribulin or pharmaceutically acceptable salt thereof | 20:1 to 200:1 |
| 11C* | I-B or pharmaceutically acceptable salt thereof | Eribulin or pharmaceutically acceptable salt thereof | 30:1 to 200:1 |
| 12C* | I-B or pharmaceutically acceptable salt thereof | Eribulin or pharmaceutically acceptable salt thereof | 20:1 to 120:1 |
| 13C | I-B as dihydrochloride salt | Eribulin mesylate | 1:1 to 600:1 |
| 14C | I-B as dihydrochloride salt | Eribulin mesylate | 4:1 to 350:1 |
| 15C | I-B as dihydrochloride salt | Eribulin mesylate | 10:1 to 250:1 |
| 16C | I-B as dihydrochloride salt | Eribulin mesylate | 20:1 to 200:1 |
| 17C | I-B as dihydrochloride salt | Eribulin mesylate | 30:1 to 200:1 |
| 18C | I-B as dihydrochloride salt | Eribulin mesylate | 20:1 to 120:1 |

*The weight:weight ratio for each embodiment is the mole equivalent weight:weight ratio of the indicated weight:weight ratios, which are based on CPI as the dihydrochloride salt of the compound of formula I-B and CII as eribulin mesylate.

All ratios described in Table B and C above are determined according to the same methodology as given for mole dosage ratios described above, i.e. the ratio of the total weight amount of the doses of the compound of formula I or pharmaceutically acceptable derivative thereof to the total weight amount of the doses of the compound of formula II or pharmaceutically acceptable salt thereof over the respective treatment cycles. Likewise, if a continuous treatment schedule is used for one combination partner and a cyclic treatment schedule is used for the other combination partner then the total weight amount of the doses of the continuous treatment over a period of the same duration of the treatment cycle of the other combination partner is used to determine the weight:weight ratio.

The method of treating neoplastic diseases such as cancer according to the invention may comprise (i) administration of the agent (a) in free or pharmaceutically acceptable salt form and (ii) administration of agent (b) in free or pharmaceutically acceptable salt form simultaneously or sequentially in any order, in jointly therapeutically effective amounts, e.g. in synergistically effective amounts, e.g. in continuous or intermittent dosing schedule corresponding to the amounts described herein. The individual combination partners of the combination of the invention may be administered separately at different times during the course of therapy or concurrently. The invention is therefore to be understood as embracing all such regimens of simultaneous or alternating treatment and the term "administering" is to be interpreted accordingly.

Effective dosages of each of the combination partners employed in the combinations of the invention may vary depending on the particular compound or pharmaceutical composition employed, the mode of administration, the condition being treated, and the severity of the condition being treated. Thus, the dosage regimen of the combination of the invention is selected in accordance with a variety of factors including the route of administration and the renal and hepatic function of the patient.

The optimum ratios, individual and combined dosages, and concentrations of the combination partners of the pharmaceutical combination of the invention that yield efficacy without toxicity are based on the kinetics of the therapeutic agents' availability to target sites. They may be established using routine clinical testing and procedures that are well known in the art and will depend upon a variety of factors, such as the mode of administration, the condition being treated and the severity of the condition being treated, as well as the age, body weight, general health, gender and diet of the individual and other medications the individual is taking.

Likewise, frequency of dosage may vary depending on the compound used and the particular condition to be treated. Patients may generally be monitored for therapeutic effectiveness using assays suitable for the condition being treated, which will be familiar to those of ordinary skill in the art.

When the combination partners, which are employed in the combination of the invention, are applied in the form as marketed as single drugs, their dosage and mode of administration may, in some embodiments, be in accordance with the information provided on the package insert of the respective marketed drugs. In some embodiments the unit dosage forms containing the combination of agents as described herein will contain the amounts of each agent of the combination that are typically administered when the agents are administered alone.

Generally the compound of formula I (e.g. the compound of formula I-A), or derivative thereof (e.g. the compound of formula I-B or pharmaceutically acceptable salt thereof, e.g. the dihydrochloride salt) may be administered orally or intravenously and will be administered at dosages which do not exceed the maximum tolerated dose (MTD) for a particular mode of administration and indication, as determined in a clinical dose escalation study.

When administered orally the dosage of the compound of formula I-B as the dihydrochloride salt per day on days when administered may be e.g. in the range of about 1 mg to about 50 mg (e.g. 1 mg to 50 mg), e.g. in the range of about 2 mg to about 30 mg (e.g. 2 mg to 30 mg), e.g. in the range of about 2 mg to about 20 mg (e.g. 2 mg to 20 mg), e.g. in the range of about 4 mg to about 20 mg (e.g. 4 mg to 20 mg), e.g. in the range of about 8 mg to about 20 mg (e.g. 8 mg to 20 mg), or in any single amount within these ranges (e.g. 4 mg, 8 mg, 12 mg or 16 mg)). For example the dosage per day on days when administered may be at least about 1 mg, e g at least about 2 mg, e.g. at least about 4 mg, e.g. at least about 8 mg, e.g. up to about 50 mg, e g up to about 30 mg, e g up to about 20 mg. When a different compound of formula I is administered, e.g. the compound of formula I-A in free form or the compound of formula I-B as a pharmaceutically acceptable salt other than the dihydrochloride salt, then the corresponding dosages amounts to give the same number of moles are administered based on the respective molecular weights.

When administered orally the compound of formula I (e.g. the compound of formula I-A), or derivative thereof (e.g. the compound of formula I-B or pharmaceutically acceptable salt thereof, e.g. the dihydrochloride salt) may be administered according to a continuous treatment schedule or a cyclic treatment schedule. Administration may be more than once per day (e.g. twice per day) if needed or desired and the dosage per administration is reduced accordingly so that the dosage on a given day remains within the specified limits. In one embodiment administration is according to a continuous treatment schedule with one dose per day for as long as needed. In one embodiment administration is according to a continuous treatment schedule with two doses per day for as long as needed.

When administered intravenously the dose of the compound of formula I-B as the dihydrochloride salt per week during weeks when administered may be e.g. in the range of about 1 mg/m$^2$ to about 250 mg/m$^2$ (e.g. 1 mg/m$^2$ to 250 mg/m$^2$), e.g. in the range of about 10 mg/m$^2$ to about 250 mg/m$^2$ (e.g. 10 mg/m$^2$ to 250 mg/m$^2$), e.g. in the range of about 15 mg/m$^2$ to about 160 mg/m$^2$ (e.g. 15 mg/m$^2$ to 160 mg/m$^2$), e.g. in the range of about 15 mg/m$^2$ to about 100 mg/m$^2$ (e.g. 15 mg/m$^2$ to 100 mg/m$^2$), e.g. in the range of about 30 mg/m$^2$ to about 100 mg/m$^2$ (e.g. 30 mg/m$^2$ to 100 mg/m$^2$), e.g. in the range of about 30 mg/m$^2$ to about 70 mg/m$^2$ (e.g. 30 mg/m$^2$ to 70 mg/m$^2$), or in any single amount within these ranges (e.g. 30 mg/m$^2$, 45 mg/m$^2$, 70 mg/m$^2$ or 90 mg/m$^2$)). For example the dose per week during weeks when administered may be e.g. at least 1 mg/m$^2$, e.g. at least about 10 mg/m$^2$, e.g. at least about 15 mg/m$^2$, e.g. at least about 30 mg/m$^2$, e.g. up to about 250 mg/m$^2$ e.g. up to about 160 mg/m$^2$, e.g. up to about 100 mg/m$^2$, e.g. up to about 70 mg/m$^2$. Likewise as above, when a different compound of formula I is administered, e.g. the compound of formula I-A in free form or the compound of formula I-B as a pharmaceutically acceptable salt other than the dihydrochloride salt, then the corresponding dosages amounts to give the same number of moles is administered based on the respective molecular weights.

When administered intravenously the compound of formula I (e.g. the compound of formula I-A), or derivative thereof (e.g. the compound of formula I-B or pharmaceutically acceptable salt thereof, e.g. the dihydrochloride salt) may be administered once per week or more than once per week, e.g. twice or three times per week. The intravenous dose may be over a period as long as needed, e.g. over a period of about 1 to about 96 hours, e.g. about 40 to about 80 hours, e.g. about 72 hours, e.g. about 40 hours to about 60 hours. In one embodiment the dose may be over a period of about 48 hours. In another embodiment the dose may be over a period of about 60 hours. In another embodiment the dose may be over a period of about 72 hours. Such intravenous administration may utilise a continuous infusion pump or other intravenous administration device.

In another embodiment the duration of administration may be e.g. a period of about 1 to about 4 hours, e.g. about 2 hours.

In one embodiment the compound of formula I or pharmaceutically acceptable derivative thereof is administered according to a 21-day treatment cycle with two days of dosing, e.g. initiated on days 1 and 8. In another embodiment the compound of formula I or pharmaceutically acceptable derivative thereof is administered according to a 28-day treatment cycle with three days of dosing, e.g. initiated on days 1, 8 and 15. In another embodiment the compound of formula I or pharmaceutically acceptable derivative thereof is administered according to a 28-day treatment cycle with two days of dosing, e.g. initiated on days 1 and 15.

The dose of the compound of formula II as eribulin mesylate per week during weeks when administered may be e.g. in the range of about 0.01 mg/m$^2$ to about 10 mg/m$^2$, (e.g. 0.01 mg/m$^2$ to 10 mg/m$^2$), e.g. in the range of about 0.1 mg/m$^2$ to about 2 mg/m$^2$, (e.g. 0.1 mg/m$^2$ to 2 mg/m$^2$), or in the range of about 0.3 mg/m$^2$ to about 1.5 mg/m$^2$, (e.g. 0.3 mg/m$^2$ to 1.5 mg/m$^2$), or in any single amount within these ranges (e.g. 1.4 mg/m$^2$ or 1.1 mg/m$^2$). For example the dose per week during weeks when administered may be e.g. at least about 0.01 mg/m$^2$, e.g. at least about 0.1 mg/m$^2$, e.g. at least about 0.3 mg/m$^2$, e.g. up to about 10 mg/m$^2$, e.g. up to about 2 mg/m$^2$, e.g. up to about 1.5 mg/m$^2$. When a salt of the compound of formula II other than the mesylate salt is administered, then the corresponding dosage amounts to give the same number of moles is administered based on the molecular weight of eribulin mesylate (given above).

The compound of formula II or pharmaceutically acceptable salt thereof can be administered as a single dose e.g. once per day, once per week, once every two weeks or once per month, or more than one dose can be administered per day, per week, per two weeks, or per month. The intravenous dose may be over a period for as long as needed, e.g. over a period of about 1 minute to about 20 minutes, e.g. over a period of about 2 minutes to about 5 minutes. In one embodiment the compound of formula II or pharmaceutically acceptable salt thereof is administered according to a 21-day treatment cycle with 2 days of dosing, e.g. initiated on days 1 and 8. In another embodiment the compound of formula I or pharmaceutically acceptable derivative thereof is administered according to a 28-day treatment cycle with two days of dosing, e.g. initiated on days 1 and 15.

More specifically, a possible dose of the compound of formula II or pharmaceutically acceptable salt (e.g. eribulin mesylate) is 1.4 mg/m$^2$ administered intravenously over 2 to 5 minutes on days 1 and 8 of a 21-day treatment cycle. A possible dose of the compound of formula II or pharmaceutically acceptable salt in patients with mild hepatic impairment (Child-Pugh A) is 1.1 mg/m$^2$ administered intravenously over 2 to 5 minutes on days 1 and 8 of a 21-day treatment cycle, while a possible dose of the compound of formula II or pharmaceutically acceptable salt (e.g. eribulin mesylate) in patients with moderate hepatic impairment (Child-Pugh B) is 0.7 mg/m² administered intravenously over 2 to 5 minutes on days 1 and 8 of a 21-day treatment cycle. Further, a possible dose of the compound of formula II or pharmaceutically acceptable salt (e.g. eribulin mesylate) in patients with moderate renal impairment (creatinine clearance of 30-50 mL/min) is 1.1 mg/m² administered intravenously over 2 to 5 minutes on days 1 and 8 of a 21-day treatment cycle. In another example, the compound of formula II or pharmaceutically acceptable salt (e.g. eribulin mesylate) can be administered on a bi-weekly schedule, e.g. once on each of days 1 and 15 of a 28-day treatment cycle e.g. wherein the dose is 1.4 mg/m² administered intravenously over 2 to 5 minutes on each of days 1 and 15 of a 28-day treatment cycle.

The dosage reductions noted above, 1.1 mg/m² in the case of patients with mild hepatic impairment or moderate renal impairment, and 0.7 mg/m² in the case of patients with moderate hepatic impairment, can also be used in bi-weekly regimens. These or other lower doses of the compound of formula II or pharmaceutically acceptable salt (e.g. eribulin mesylate) can optionally be used in the context of patients having adverse reactions (e.g. hematologic or other adverse reactions) or in combination treatment, according to the methods of the present invention.

The above-given doses of eribulin mesylate may be converted into corresponding doses of eribulin freebase. For example, a dose of 1.4 mg/m² of eribulin mesylate may correspond to a dose of 1.23 mg/m² of the eribulin free base, 1.1 mg/m² of eribulin mesylate may correspond to a dose of 0.97 mg/m² of the free base, and 0.7 mg/m² of eribulin mesylate may correspond to a dose of 0.62 mg/m² of the free base.

The compound of formula I (e.g. the compound of formula I-A or pharmaceutically acceptable salt thereof) or derivative thereof (e.g. the compound of formula I-B or pharmaceutically acceptable salt thereof) and compound of formula II or pharmaceutically acceptable salt thereof (e.g. eribulin mesylate) compositions can be administered to a patient substantially simultaneously or sequentially and in either order (e.g. administration of the compound of formula I or derivative thereof prior to the compound of formula II or pharmaceutically acceptable salt thereof, or vice versa).

In one embodiment the compound of formula I-B as the dihydrochloride salt is administered to a patient orally, e.g. wherein the compound is administered every day and the dose per day is about 2 mg to about mg, e.g. about 2 mg to about 20 mg, e g about 4 mg to about 20 mg, e.g. about 8 mg to about 20 mg), while eribulin mesylate is administered to a patient by intravenous infusion wherein the dose per week during weeks when administered is e.g. about 0.1 mg/m² to about 2 mg/m², e.g. about 0.3 to about 1.5 mg/m², e.g. 1.1 mg/m² or 1.4 mg/m², e.g. over about 1 minute to about 20 minutes, e.g. over about 2 minutes to about 5 minutes, e.g. with 2 days of dosing in a 21-day treatment cycle, e.g. initiated on days 1 and 8, or e.g. two days of dosing in a 28-day treatment cycle, e.g. initiated on days 1 and 15. This course of treatment can be repeated (e.g. 1 to 8 times or may be open-ended), as determined to be tolerable and effective by those of skill in the art.

In another embodiment the compound of formula I-B as the dihydrochloride salt) is administered to a patient by intravenous infusion, e.g. wherein the dose per week during weeks when administered is about 15 mg/m² to about 160 mg/m², e.g. about 15 mg/m² to about 100 mg/m², e.g. about 30 mg/m² to about 100 mg/m², e.g. about 30 mg/m² to about 70 mg/m², e.g. over a period of about 24 to about 72 hours, with e.g. two days of dosing in a 21-day treatment cycle, e.g. initiated on days 1 and 8, or e.g. two days of dosing in a 28-day treatment cycle, e.g. initiated on days 1 and 15, or e.g. three days of dosing in a 28-day treatment cycle, e.g. on day 1, 8 and 15, while eribulin mesylate is administered to a patient by intravenous infusion e.g. wherein the dose per week during weeks when administered is about 0.1 mg/m² to about 2 mg/m², e.g. about 0.3 to about 1.5 mg/m², e.g. 1.1 mg/m² or 1.4 mg/m², e.g. over about 1 minute to about 20 minutes, e.g. over about 2 minutes to about 5 minutes, e.g. with two days of dosing in a 21-day treatment cycle, e.g. initiated on days 1 and 8, or e.g. two days of dosing in a 28-day treatment cycle, e.g. initiated on days 1 and 15. This course of treatment can be repeated (e.g. 1 to 8 or may be open-ended), as determined to be tolerable and effective by those of skill in the art.

Additional embodiments of the invention are shown in Table D below.

TABLE D

| Embodiment | Combination partner I (CPI) | Combination partner II (CPII) | Dosage CPI (depicted above) Dosage CPII (depicted below) |
|---|---|---|---|
| 1D* | I-A or pharmaceutically acceptable salt thereof or I-B or pharmaceutically acceptable salt thereof | Eribulin or pharmaceutically acceptable salt thereof | oral, 2 to 30 mg (dose per day on days when administered) IV, 0.1 to 2 mg/m² (dose per week in weeks when administered) |
| 2D* | I-A or pharmaceutically acceptable salt thereof or I-B or pharmaceutically acceptable salt thereof | Eribulin or pharmaceutically acceptable salt thereof | oral, 4 to 20 mg (dose per day), dose every day IV, 0.3 to 1.5 mg/m² (dose per week in weeks when administered), 2 doses per 21-day treatment cycle e.g. initiated on days 1 and 8 |
| 3D* | I-A or pharmaceutically acceptable salt thereof or I-B or pharmaceutically acceptable salt thereof | Eribulin or pharmaceutically acceptable salt thereof | oral, 4 to 20 mg (dose per day), dose every day IV, 0.3 to 1.5 mg/m² (dose per week dose in weeks when administered), 2 doses per 28-day treatment cycle e.g. initiated on days 1 and 15 |

TABLE D-continued

| Embodiment | Combination partner I (CPI) | Combination partner II (CPII) | Dosage CPI (depicted above) Dosage CPII (depicted below) |
|---|---|---|---|
| 4D* | I-A or pharmaceutically acceptable salt thereof or I-B or pharmaceutically acceptable salt thereof | Eribulin or pharmaceutically acceptable salt thereof | oral, 8 to 20 mg (dose per day), dose every day IV, 0.3 to 1.5 mg/m$^2$ (dose per week in weeks when administered), 2 doses per 21-day treatment cycle e.g. initiated on days 1 and 8 |
| 5D* | I-A or pharmaceutically acceptable salt thereof or I-B or pharmaceutically acceptable salt thereof | Eribulin or pharmaceutically acceptable salt thereof | oral, 8 to 20 mg (dose per day), dose every day IV, 0.3 to 1.5 mg/m$^2$ (dose per week dose in weeks when administered), 2 doses per 28-day treatment cycle e.g. initiated on days 1 and 15 |
| 6D* | I-B or pharmaceutically acceptable salt thereof | Eribulin or pharmaceutically acceptable salt thereof | oral, 2 to 30 mg (dose per day on days when administered) IV, 0.1 to 2 mg/m$^2$ (dose per week in weeks when administered) |
| 7D* | I-B or pharmaceutically acceptable salt thereof | Eribulin or pharmaceutically acceptable salt thereof | oral, 4 to 20 mg (dose per day), dose every day IV, 0.3 to 1.5 mg/m$^2$ (dose per week in weeks when administered), 2 doses per 21-day treatment cycle e.g. initiated on days 1 and 8 |
| 8D* | I-B or pharmaceutically acceptable salt thereof | Eribulin or pharmaceutically acceptable salt thereof | oral, 4 to 20 mg (dose per day), dose every day IV, 0.3 to 1.5 mg/m$^2$ (dose per week dose in weeks when administered), 2 doses per 28-day treatment cycle e.g. initiated on days 1 and 15 |
| 9D* | I-B or pharmaceutically acceptable salt thereof | Eribulin or pharmaceutically acceptable salt thereof | oral, 8 to 20 mg (dose per day), dose every day IV, 0.3 to 1.5 mg/m$^2$ (dose per week in weeks when administered), 2 doses per 21-day treatment cycle e.g. initiated on days 1 and 8 |
| 10D* | I-B or pharmaceutically acceptable salt thereof | Eribulin or pharmaceutically acceptable salt thereof | oral, 8 to 20 mg (dose per day), dose every day IV, 0.3 to 1.5 mg/m$^2$ (dose per week dose in weeks when administered), 2 doses per 28-day treatment cycle e.g. initiated on days 1 and 15 |
| 11D | I-B as dihydrochloride salt | Eribulin mesylate | oral, 2 to 30 mg (dose per day on days when administered) IV, 0.1 to 2 mg/m$^2$ (dose per week in weeks when administered) |
| 12D | I-B as dihydrochloride salt | Eribulin mesylate | oral, 4 to 20 mg (dose per day), dose every day IV, 0.3 to 1.5 mg/m$^2$ (dose per week in weeks when administered), 2 doses per 21-day treatment cycle e.g. initiated on days 1 and 8 |
| 13D | I-B as dihydrochloride salt | Eribulin mesylate | oral, 4 to 20 mg (dose per day), dose every day IV, 0.3 to 1.5 mg/m$^2$ (dose per week dose in weeks when administered), 2 doses per 28-day treatment cycle e.g. initiated on days 1 and 15 |
| 14D | I-B as dihydrochloride salt | Eribulin mesylate | oral, 8 to 20 mg (dose per day), dose every day IV, 0.3 to 1.5 mg/m$^2$ (dose per week in weeks when administered), 2 doses per 21-day treatment cycle e.g. initiated on days 1 and 8 |
| 15D | I-B as dihydrochloride salt | Eribulin mesylate | oral, 8 to 20 mg (dose per day), dose every day IV, 0.3 to 1.5 mg/m$^2$ (dose per week dose in weeks when administered), 2 doses per 28-day treatment cycle e.g. initiated on days 1 and 15 |
| 16D* | I-A or pharmaceutically acceptable salt thereof or I-B or pharmaceutically acceptable salt thereof | Eribulin or pharmaceutically acceptable salt thereof | IV, 15 to 160 mg/m$^2$ (dose per week in weeks when administered) IV, 0.1 to 2 mg/m$^2$ (dose per week in weeks when administered) |

TABLE D-continued

| Embodiment | Combination partner I (CPI) | Combination partner II (CPII) | Dosage CPI (depicted above) Dosage CPII (depicted below) |
|---|---|---|---|
| 17D* | I-A or pharmaceutically acceptable salt thereof or I-B or pharmaceutically acceptable salt thereof | Eribulin or pharmaceutically acceptable salt thereof | IV, 15 to 160 mg/m$^2$ (dose per week in weeks when administered), 2 doses per 21-day treatment cycle, e.g. initiated on days 1 and 8 IV, 0.1 to 2 mg/m$^2$ (dose per week in weeks when administered), 2 doses per 21-day treatment cycle, e.g. initiated on days 1 and 8 |
| 18D* | I-A or pharmaceutically acceptable salt thereof or I-B or pharmaceutically acceptable salt thereof | Eribulin or pharmaceutically acceptable salt thereof | IV, 15 to 160 mg/m$^2$ (dose per week in weeks when administered), 3 doses per 28-day treatment cycle, e.g. initiated on days 1, 8 and 15 IV, 0.1 to 2 mg/m$^2$ (dose per week in weeks when administered), 2 doses per 21-day treatment cycle e.g. initiated on days 1 and 8 |
| 19D* | I-A or pharmaceutically acceptable salt thereof or I-B or pharmaceutically acceptable salt thereof | Eribulin or pharmaceutically acceptable salt thereof | IV, 15 to 160 mg/m$^2$ (dose per week in weeks when administered), 2 doses per 21-day treatment cycle, e.g. initiated on days 1 and 8 IV, 0.1 to 2 mg/m$^2$ (dose per week in weeks when administered), 2 doses per 28-day treatment cycle e.g. initiated on days 1 and 15 |
| 20D* | I-A or pharmaceutically acceptable salt thereof or I-B or pharmaceutically acceptable salt thereof | Eribulin or pharmaceutically acceptable salt thereof | IV, 15 to 160 mg/m$^2$ (dose per week in weeks when administered) 3 doses per 28-day treatment cycle, e.g. initiated on days 1, 8 and 15 IV, 0.1 to 2 mg/m$^2$ (dose per week in weeks when administered), 2 doses per 28-day treatment cycle e.g. initiated on days 1 and 15 |
| 21D* | I-A or pharmaceutically acceptable salt thereof or I-B or pharmaceutically acceptable salt thereof | Eribulin or pharmaceutically acceptable salt thereof | IV, 30 to 100 mg/m$^2$ (dose per week in weeks when administered), 2 doses per 21-day treatment cycle, e.g. initiated on days 1 and 8 IV, 0.3 to 1.5 mg/m$^2$ (accumulated dose per week in weeks when administered), 2 doses per 21-day treatment cycle, e.g. initiated on days 1 and 8 |
| 22D* | I-A or pharmaceutically acceptable salt thereof or I-B or pharmaceutically acceptable salt thereof | Eribulin or pharmaceutically acceptable salt thereof | IV, 30 to 100 mg/m$^2$ (dose per week in weeks when administered), 3 doses per 28-day treatment cycle, e.g. initiated on days 1, 8 and 15 IV, 0.3 to 1.5 mg/m$^2$ (dose per week in weeks when administered), 2 doses per 21-day treatment cycle e.g. initiated on days 1 and 8 |
| 23D* | I-A or pharmaceutically acceptable salt thereof or I-B or pharmaceutically acceptable salt thereof | Eribulin or pharmaceutically acceptable salt thereof | IV, 30 to 100 mg/m$^2$ (dose per week in weeks when administered), 2 doses per 21-day treatment cycle, e.g. initiated on days 1 and 8 IV, 0.3 to 1.5 mg/m$^2$ (dose per week in weeks when administered), 2 doses per 28-day treatment cycle e.g. initiated on days 1 and 15 |
| 24D* | I-A or pharmaceutically acceptable salt thereof or I-B or pharmaceutically acceptable salt thereof | Eribulin or pharmaceutically acceptable salt thereof | IV, 30 to 100 mg/m$^2$ (dose per week in weeks when administered), 3 doses per 28-day treatment cycle, e.g. initiated on days 1, 8 and 15 IV, 0.3 to 1.5 mg/m$^2$ (dose per week in weeks when administered), 2 doses per 28-day treatment cycle e.g. initiated on days 1 and 15 |
| 25D* | I-A or pharmaceutically acceptable salt thereof or I-B or pharmaceutically acceptable salt thereof | Eribulin or pharmaceutically acceptable salt thereof | IV, 30 to 70 mg/m$^2$ (dose per week in weeks when administered), 2 doses per 21-day treatment cycle, e.g. initiated on days 1 and 8 IV, 0.3 to 1.5 mg/m$^2$ (accumulated dose per week in weeks when administered), 2 doses per 21-day treatment cycle, e.g. initiated on days 1 and 8 |

TABLE D-continued

| Embodiment | Combination partner I (CPI) | Combination partner II (CPII) | Dosage CPI (depicted above) Dosage CPII (depicted below) |
|---|---|---|---|
| 26D* | I-A or pharmaceutically acceptable salt thereof or I-B or pharmaceutically acceptable salt thereof | Eribulin or pharmaceutically acceptable salt thereof | IV, 30 to 70 mg/m$^2$ (dose per week in weeks when administered), 3 doses per 28-day treatment cycle, e.g. initiated on days 1, 8 and 15 IV, 0.3 to 1.5 mg/m$^2$ (dose per week in weeks when administered), 2 doses per 21-day treatment cycle e.g. initiated on days 1 and 8 |
| 27D* | I-A or pharmaceutically acceptable salt thereof or I-B or pharmaceutically acceptable salt thereof | Eribulin or pharmaceutically acceptable salt thereof | IV, 30 to 70 mg/m$^2$ (dose per week in weeks when administered), 2 doses per 21-day treatment cycle, e.g. initiated on days 1 and 8 IV, 0.3 to 1.5 mg/m$^2$ (dose per week in weeks when administered), 2 doses per 28-day treatment cycle e.g. initiated on days 1 and 15 |
| 28D* | I-A or pharmaceutically acceptable salt thereof or I-B or pharmaceutically acceptable salt thereof | Eribulin or pharmaceutically acceptable salt thereof | IV, 30 to 70 mg/m$^2$ (dose per week in weeks when administered), 3 doses per 28-day treatment cycle, e.g. initiated on days 1, 8 and 15 IV, 0.3 to 1.5 mg/m$^2$ (dose per week in weeks when administered), 2 doses per 28-day treatment cycle e.g. initiated on days 1 and 15 |
| 29D* | I-B or pharmaceutically acceptable salt thereof | Eribulin or pharmaceutically acceptable salt thereof | IV, 15 to 160 mg/m$^2$ (dose per week in weeks when administered) IV, 0.1 to 2 mg/m$^2$ (dose per week in weeks when administered) |
| 30D* | I-B or pharmaceutically acceptable salt thereof | Eribulin or pharmaceutically acceptable salt thereof | IV, 15 to 160 mg/m$^2$ (dose per week in weeks when administered), 2 doses per 21-day treatment cycle, e.g. initiated on days 1 and 8 IV, 0.1 to 2 mg/m$^2$ (dose per week in weeks when administered), 2 doses per 21-day treatment cycle, e.g. initiated on days 1 and 8 |
| 31D* | I-B or pharmaceutically acceptable salt thereof | Eribulin or pharmaceutically acceptable salt thereof | IV, 15 to 160 mg/m$^2$ (dose per week in weeks when administered), 3 doses per 28-day treatment cycle, e.g. initiated on days 1, 8 and 15 IV, 0.1 to 2 mg/m$^2$ (dose per week in weeks when administered), 2 doses per 21-day treatment cycle e.g. initiated on days 1 and 8 |
| 32D* | I-B or pharmaceutically acceptable salt thereof | Eribulin or pharmaceutically acceptable salt thereof | IV, 15 to 160 mg/m$^2$ (dose per week in weeks when administered), 2 doses per 21-day treatment cycle, e.g. initiated on days 1 and 8 IV, 0.1 to 2 mg/m$^2$ (dose per week in weeks when administered), 2 doses per 28-day treatment cycle e.g. initiated on days 1 and 15 |
| 33D* | I-B or pharmaceutically acceptable salt thereof | Eribulin or pharmaceutically acceptable salt thereof | IV, 15 to 160 mg/m$^2$ (dose per week in weeks when administered) 3 doses per 28-day treatment cycle, e.g. initiated on days 1, 8 and 15 IV, 0.1 to 2 mg/m$^2$ (dose per week in weeks when administered), 2 doses per 28-day treatment cycle e.g. initiated on days 1 and 15 |
| 34D* | I-B or pharmaceutically acceptable salt thereof | Eribulin or pharmaceutically acceptable salt thereof | IV, 30 to 100 mg/m$^2$ (dose per week in weeks when administered), 2 doses per 21-day treatment cycle, e.g. initiated on days 1 and 8 IV, 0.3 to 1.5 mg/m$^2$ (accumulated dose per week in weeks when administered), 2 doses per 21-day treatment cycle, e.g. initiated on days 1 and 8 |
| 35D* | I-B or pharmaceutically acceptable salt thereof | Eribulin or pharmaceutically acceptable salt thereof | IV, 30 to 100 mg/m$^2$ (dose per week in weeks when administered), 3 doses per 28-day treatment cycle, e.g. initiated on days 1, 8 and 15 IV, 0.3 to 1.5 mg/m$^2$ (dose per week in weeks when administered), 2 doses per 21-day treatment cycle e.g. initiated on days 1 and 8 |

TABLE D-continued

| Embodiment | Combination partner I (CPI) | Combination partner II (CPII) | Dosage CPI (depicted above) Dosage CPII (depicted below) |
|---|---|---|---|
| 36D* | I-B or pharmaceutically acceptable salt thereof | Eribulin or pharmaceutically acceptable salt thereof | IV, 30 to 100 mg/m$^2$ (dose per week in weeks when administered), 2 doses per 21-day treatment cycle, e.g. initiated on days 1 and 8 IV, 0.3 to 1.5 mg/m$^2$ (dose per week in weeks when administered), 2 doses per 28-day treatment cycle e.g. initiated on days 1 and 15 |
| 37D* | I-B or pharmaceutically acceptable salt thereof | Eribulin or pharmaceutically acceptable salt thereof | IV, 30 to 100 mg/m$^2$ (dose per week in weeks when administered), 3 doses per 28-day treatment cycle, e.g. initiated on days 1, 8 and 15 IV, 0.3 to 1.5 mg/m$^2$ (dose per week in weeks when administered), 2 doses per 28-day treatment cycle e.g. initiated on days 1 and 15 |
| 38D* | I-B or pharmaceutically acceptable salt thereof | Eribulin or pharmaceutically acceptable salt thereof | IV, 30 to 70 mg/m$^2$ (dose per week in weeks when administered), 2 doses per 21-day treatment cycle, e.g. initiated on days 1 and 8 IV, 0.3 to 1.5 mg/m$^2$ (accumulated dose per week in weeks when administered), 2 doses per 21-day treatment cycle, e.g. initiated on days 1 and 8 |
| 39D* | I-B or pharmaceutically acceptable salt thereof | Eribulin or pharmaceutically acceptable salt thereof | IV, 30 to 70 mg/m$^2$ (dose per week in weeks when administered), 3 doses per 28-day treatment cycle, e.g. initiated on days 1, 8 and 15 IV, 0.3 to 1.5 mg/m$^2$ (dose per week in weeks when administered), 2 doses per 21-day treatment cycle e.g. initiated on days 1 and 8 |
| 40D* | I-B or pharmaceutically acceptable salt thereof | Eribulin or pharmaceutically acceptable salt thereof | IV, 30 to 70 mg/m$^2$ (dose per week in weeks when administered), 2 doses per 21-day treatment cycle, e.g. initiated on days 1 and 8 IV, 0.3 to 1.5 mg/m$^2$ (dose per week in weeks when administered), 2 doses per 28-day treatment cycle e.g. initiated on days 1 and 15 |
| 41D* | I-B or pharmaceutically acceptable salt thereof | Eribulin or pharmaceutically acceptable salt thereof | IV, 30 to 70 mg/m$^2$ (dose per week in weeks when administered), 3 doses per 28-day treatment cycle, e.g. initiated on days 1, 8 and 15 IV, 0.3 to 1.5 mg/m$^2$ (dose per week in weeks when administered), 2 doses per 28-day treatment cycle e.g. initiated on days 1 and 15 |
| 42D | I-B as dihydrochloride salt | Eribulin mesylate | IV, 15 to 160 mg/m$^2$ (dose per week in weeks when administered) IV, 0.1 to 2 mg/m$^2$ (dose per week in weeks when administered) |
| 43D | I-B as dihydrochloride salt | Eribulin mesylate | IV, 15 to 160 mg/m$^2$ (dose per week in weeks when administered), 2 doses per 21-day treatment cycle, e.g. initiated on days 1 and 8 IV, 0.1 to 2 mg/m$^2$ (dose per week in weeks when administered), 2 doses per 21-day treatment cycle, e.g. initiated on days 1 and 8 |
| 44D | I-B as dihydrochloride salt | Eribulin mesylate | IV, 15 to 160 mg/m$^2$ (dose per week in weeks when administered), 3 doses per 28-day treatment cycle, e.g. initiated on days 1, 8 and 15 IV, 0.1 to 2 mg/m$^2$ (dose per week in weeks when administered), 2 doses per 21-day treatment cycle e.g. initiated on days 1 and 8 |
| 45D | I-B as dihydrochloride salt | Eribulin mesylate | IV, 15 to 160 mg/m$^2$ (dose per week in weeks when administered), 2 doses per 21-day treatment cycle, e.g. initiated on days 1 and 8 IV, 0.1 to 2 mg/m$^2$ (dose per week in weeks when administered), 2 doses dosing per 28-day treatment cycle e.g. initiated on days 1 and 15 |

TABLE D-continued

| Embodiment | Combination partner I (CPI) | Combination partner II (CPII) | Dosage CPI (depicted above) Dosage CPII (depicted below) |
|---|---|---|---|
| 46D | I-B as dihydrochloride salt | Eribulin mesylate | IV, 15 to 160 mg/m$^2$ (dose per week in weeks when administered) 3 doses per 28-day treatment cycle, e.g. initiated on days 1, 8 and 15<br>IV, 0.1 to 2 mg/m$^2$ (dose per week in weeks when administered), 2 doses per 28-day treatment cycle e.g. initiated on days 1 and 15 |
| 47D | I-B as dihydrochloride salt | Eribulin mesylate | IV, 30 to 100 mg/m$^2$ (dose per week in weeks when administered), 2 doses per 21-day treatment cycle, e.g. initiated on days 1 and 8<br>IV, 0.3 to 1.5 mg/m$^2$ (accumulated dose per week in weeks when administered), 2 doses per 21-day treatment cycle, e.g. initiated on days 1 and 8 |
| 48D | I-B as dihydrochloride salt | Eribulin mesylate | IV, 30 to 100 mg/m$^2$ (dose per week in weeks when administered), 3 doses ng per 28-day treatment cycle, e.g. initiated on days 1, 8 and 15<br>IV, 0.3 to 1.5 mg/m$^2$ (dose per week in weeks when administered), 2 doses per 21-day treatment cycle e.g. initiated on days 1 and 8 |
| 49D | I-B as dihydrochloride salt | Eribulin mesylate | IV, 30 to 100 mg/m$^2$ (dose per week in weeks when administered), 2 doses per 21-day treatment cycle, e.g. initiated on days 1 and 8<br>IV, 0.3 to 1.5 mg/m$^2$ (dose per week in weeks when administered), 2 doses per 28-day treatment cycle e.g. initiated on days 1 and 15 |
| 50D | I-B as dihydrochloride salt | Eribulin mesylate | IV, 30 to 100 mg/m$^2$ (dose per week in weeks when administered), 3 doses per 28-day treatment cycle, e.g. initiated on days 1, 8 and 15<br>IV, 0.3 to 1.5 mg/m$^2$ (dose per week in weeks when administered), 2 doses per 28-day treatment cycle e.g. initiated on days 1 and 15 |
| 51D | I-B as dihydrochloride salt | Eribulin mesylate | IV, 30 to 70 mg/m$^2$ (dose per week in weeks when administered), 2 doses per 21-day treatment cycle, e.g. initiated on days 1 and 8<br>IV, 0.3 to 1.5 mg/m$^2$ (accumulated dose per week in weeks when administered), 2 doses per 21-day treatment cycle, e.g. initiated on days 1 and 8 |
| 52D | I-B as dihydrochloride salt | Eribulin mesylate | IV, 30 to 70 mg/m$^2$ (dose per week in weeks when administered), 3 doses ng per 28-day treatment cycle, e.g. initiated on days 1, 8 and 15<br>IV, 0.3 to 1.5 mg/m$^2$ (dose per week in weeks when administered), 2 doses per 21-day treatment cycle e.g. initiated on days 1 and 8 |
| 53D | I-B as dihydrochloride salt | Eribulin mesylate | IV, 30 to 70 mg/m$^2$ (dose per week in weeks when administered), 2 doses per 21-day treatment cycle, e.g. initiated on days 1 and 8<br>IV, 0.3 to 1.5 mg/m$^2$ (dose per week in weeks when administered), 2 doses per 28-day treatment cycle e.g. initiated on days 1 and 15 |
| 54D | I-B as dihydrochloride salt | Eribulin mesylate | IV, 30 to 70 mg/m$^2$ (dose per week in weeks when administered), 3 doses per 28-day treatment cycle, e.g. initiated on days 1, 8 and 15<br>IV, 0.3 to 1.5 mg/m$^2$ (dose per week in weeks when administered), 2 doses per 28-day treatment cycle e.g. initiated on days 1 and 15 |

*The applicable weight range for each embodiment is the mole equivalent weight range of the indicated weight range, which is based on combination partner I as the dihydrochloride salt of the compound of formula I-B and combination partner II as eribulin mesylate.

Formulations

The combination of the invention may be formulated as pharmaceutical compositions for non-parenteral administration, such as nasal, buccal, rectal, pulmonary, vaginal, sublingual, topical, transdermal, ophthalmic, otic or, especially, for oral administration, e.g. in the form of oral solid dosage forms, e.g. granules, pellets, powders, tablets, film or sugar coated tablets, effervescent tablets, hard and soft gelatin or HPMC capsules, coated as applicable, orally disintegrating tablets, oral solutions, lipid emulsions or suspensions, or for parenteral administration, such as intravenous, intramuscular, or subcutaneous, intrathecal, intradermal or epidural administration, to mammals, especially humans, e.g. in the form of solutions, lipid emulsions or suspensions containing microparticles or nanoparticles. The compositions may comprise the active ingredient(s) alone or, preferably, together with a pharmaceutically acceptable carrier.

The pharmaceutical compositions can be processed with pharmaceutically inert, inorganic or organic excipients for the production of oral solid dosage forms, e.g. granules, pellets, powders, tablets, film or sugar coated tablets, effervescent tablets, hard gelatin or HPMC capsules or orally disintegrating tablets. Fillers e.g. lactose, cellulose, mannitol, sorbitol, calcium phosphate, starch or derivatives thereof, binders e.g. cellulose, starch, polyvinylpyrrolidone, or derivatives thereof, glidants e.g. talcum, stearic acid or its salts, flowing agents e.g. fumed silica, can be used as such excipients for formulating and manufacturing of oral solid dosage forms, such as granules, pellets, powders, tablets, film or sugar coated tablets, effervescent tablets, hard gelatin or HPMC capsules, or orally disintegrating tablets. Suitable excipients for soft gelatin capsules are e.g. vegetable oils, waxes, fats, semisolid and liquid polyols etc. Suitable excipients for the manufacture of oral solutions, lipid emulsions or suspensions are e.g. water, alcohols, polyols, saccharose, invert sugar, glucose etc. Suitable excipients for parenteral formulations are e.g. water, alcohols, polyols, glycerol, vegetable oils, lecithin, surfactants etc. Moreover, the pharmaceutical preparations can contain preservatives, solubilizers, stabilizers, wetting agents, emulsifiers, sweeteners, colorants, flavourants, salts for varying the osmotic pressure, buffers, masking agents or antioxidants. They can also contain other therapeutically valuable substances.

In addition pharmaceutical compositions used in the invention optionally include buffers such as phosphate, citrate, or other organic acids; antioxidants including butylated hydroxytoluene (BHT), butylated hydroxyanisole (BHA), ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, or other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, the pharmaceutical compositions contain a pharmaceutically acceptable preservative. In some embodiments the preservative concentration ranges from 0.1 to 2.0 percent, typically v/v. Suitable preservatives include those known in the pharmaceutical arts, such as benzyl alcohol, phenol, m-cresol, methylparaben, and propylparaben.

An example of an oral composition of the compound of formula I, e.g. the compound formula I-B in the form of its dihydrochloride salt, includes but is not limited to HPMC capsules containing 1 mg active ingredient, 98 mg of mannitol and 1 mg magnesium stearate, or 5 mg active ingredient, 94 mg mannitol and 1 mg magnesium stearate.

For intravenous administration of the compound of formula I-B, e.g. the compound of formula I-B in the form of its dihydrochloride salt, the compound of formula I or derivative thereof may be provided in powder (e.g. lyophilized) form and reconstituted with a suitable diluent, e.g. saline solution or Ringer lactate solution, immediately prior to administration. The active ingredient may be initially reconstituted with saline solution or Ringer lactate solution and then diluted to the required concentration with Ringer lactate solution.

Eribulin is typically provided in liquid form for parenteral administration, particularly intravenous administration. In one example, eribulin (e.g. eribulin mesylate) is formulated in 0.9 weight percent sodium chloride in water for injection (0.9% Sodium Chloride Injection USP).

The pharmaceutical composition may contain, from about 0.1 percent to about 99.9 percent, preferably from about 1 percent to about 60 percent, of the therapeutic agent(s)

Kits

The invention also provides pharmaceutical products such as kits which may include a container with the compound of formula I or derivative thereof (e.g. the compound of formula I-A or pharmaceutically acceptable salt thereof or the compound of formula I-B or pharmaceutically acceptable salt thereof) and/or a container with the compound of formula II or pharmaceutically acceptable salt thereof (e.g. eribulin mesylate). The active ingredients in such kits can be provided in amounts sufficient to treat a neoplastic disease such as cancer in a patient in need thereof (e.g. amounts sufficient for a single administration or for multiple administrations). The kits can thus include multiple containers which each include pharmaceutically effective amounts of the active ingredients. Optionally, instruments and/or devices necessary for administering the pharmaceutical composition(s) can also be included in the kits. Furthermore, the kits can include additional components, such as instructions or administration schedules, for treating a patient with cancer with the combinations of the invention.

Accordingly, in a further aspect the invention provides a pharmaceutical product such as a kit e.g. for use in treating a neoplastic disease such as cancer, the pharmaceutical product comprising the pharmaceutical combination of the invention, wherein component (a) and component (b) are provided as separate dosage units. In one embodiment the kit further comprises instructions for simultaneous, separate or sequential administration thereof for use in the treatment of a neoplastic disease, in particular a cancer.

Additional Therapeutics

The combination of the invention may used alone in the treatment of the medical conditions described herein. It is also contemplated that the combination is used together with a surgical procedure (for example to remove or reduce the size of a tumour), radiation therapy, ablation therapy and/or one or more therapeutic agents other than a compound of the formula I or formula II. Examples of anti-cancer agents that can be used together with the combination of the invention include but are not limited to chemotherapy (cytotoxic therapy), kinase inhibitors, endocrine therapy, biologics, immunotherapy, or a combination of these.

All aspects and embodiments of the invention described herein may be combined in any combination where possible.

For the avoidance of doubt, where ranges are mentioned (e.g. "in the range of . . . ") the end points of the range are also included in the range.

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Particular embodiments of the invention are described in the following Examples, which serve to illustrate the invention in more detail and should not be construed as limiting the invention in any way.

EXAMPLES

Cell Cultures and Cell Lines for In Vitro Experiments

The following human cell line was used: MDA-MB-231 (ATCC: HTB-26). In addition the following enhanced green fluorescent protein (EGFP)-transfected human cell lines were used: NCI-H460 (ATCC: HTB-177) (H460GFP) and Jurkat (ATCC: TIB-152) (JurkatGFP). NCI-H460 and Jurkat cell lines were cultured in RPMI-1640 tissue culture medium containing 10% (v/v) fetal calf serum, 2 mM glutamine, non-essential amino acids and 50 µg/ml penicillin/streptomycin (Complete medium) (Sigma, Buchs, Switzerland). The MDA-MB-231 cell line was cultured in Dulbecco's Modified Eagle Medium (DMEM) (high glucose) tissue culture medium containing 10% (v/v) fetal calf serum, 1 mM sodium pyruvate and 50 µg/ml penicillin/streptomycin (i.e. Complete Medium) (Sigma, Buchs, Switzerland).

General growth conditions were 37° C. and 7.5% $CO_2$. For the microtubule destabilization assay cell lines were cultured in 5% $CO_2$.

Apoptosis Assay

The assays were performed in commercially available sterile 96-well U-bottom or 24-well flat-bottom tissue culture plates (Falcon). A defined number of test cells expressing enhanced green fluorescent protein (EGFP) (H460 cells: 600 µl of 30'000 cells/ml in 24-well flat-bottom plates, Jurkat cells: 600 µl of 400'000 cells/ml in 96 well U-bottom plates) were plated either 24 hours before treatment in case of the adherent H460 cell line, or one hour prior to the start of the treatment for Jurkat cells. Between seeding and addition of compounds, the cells were incubated at 37° C. under 7.5% $CO_2$. Subsequently, BAL27862 and eribulin (Halaven®, Ch.-B. 60363CRN1, Eisai) which were dissolved in Complete Medium were both added from stock solutions at 5× the final concentration in 200 µl to the wells, resulting in a final well-volume of 1 ml. The test plates were then incubated for the indicated time. For time course experiments with Jurkat cells, the 96-well plates were removed shortly at the indicated time from the incubator, shaken in order to suspend the cells and an aliquot of 200 µl cell suspension was then transferred to a 96-well U-bottom plate and measured immediately on a fluorescence-activated cell sorting (FACS)-Canto II with a high through-put sampler (HTS)-module. The 96-well plate was then further incubated as required. In the case of the adherent cell lines, the culture supernatant and the detached cells harvested by trypsinization were pooled in FACS-tubes (BD-Biosciences) and centrifuged at 150 g for 5 minutes at room temperature. Subsequently, the cells were taken up in 200 µl complete medium and transferred to 96-well U-bottom plates for immediate measurement on a FACS-Canto II as described above.

Quantification of Apoptosis

The quantification of the relative amount of apoptotic cells within a cell population was determined according to the Reference of Strebel et al., Cytometry 2001, 43(2), Green Fluorescent Protein as Novel Tool to Measure Apoptosis and Necrosis). By monitoring the EGFP fluorescence activity excited at 488 nM and measured at 520 nM on a FACS-Cantoll™, it is possible to distinguish between proliferating cells, apoptotic cells and necrotic cells within the same cell population. The proliferating cells show a high GFP fluorescence activity, the apoptotic population shows an intermediate fluorescence activity whereas the necrotic cells demonstrate a residual fluorescence activity comparable to mock-transfected cells. Within the CellQuest™ Software (BD Biosciences) three regions are defined in the histogram: M1 comprising the proliferating cells, M2 comprising the apoptotic cell population and M3 comprising the necrotic cell population. As a readout the relative abundance of the cells belonging to M2 (apoptotic population) were expressed.

Cellular Microtubule Destabilization Assay and Immunoblotting for Tubulin

Trypsinized MDA-MB-231 cells (500'000 cells per treatment) were treated in 1 mL medium containing BAL27862 and/or eribulin (Halaven®, Ch.-B. 60363CRN1, Eisai) or appropriate vehicle control (dimethylsulfoxide (DMSO)) for 2 hours in a water bath at 37° C. After centrifugation (1'200 rpm, 3 minutes in Heraeus Labofuge 400R) cells were lyzed in 500 µL of pre-warmed hypotonic lysis buffer (20 mM Tris-HCl pH 7-8, 1 mM $MgCl_2$, 2 mM egtazic acid (EGTA), 0.5% (v/v) NP40, protease and phosphatase inhibitor cocktail (Thermo Scientific)) containing 80 nM Taxol (Enzo, #BML-T104) and incubated for 5 minutes at 37° C. The lysates were then centrifuged at room temperature for 15 minutes at 16'200×g (13'000 rpm, Eppendorf 5417R tabletop centrifuge). 180 µL of the supernatant was transferred to a fresh tube containing 60 µL 4× reducing Laemmli sample buffer (Bio-Rad), referred to here as the soluble tubulin fraction. The pellet was resuspended in 80 µL of 1× reducing Laemmli sample buffer, referred to here as the particulate fraction. Samples were boiled for 5 minutes at 95° C. Immunoblotting was performed using 15 µL sample. Proteins were separated on a 4-20% (w/v) Mini-PROTEAN® TGX gel (Bio-Rad) and transferred to a polyvinylidene difluoride (PVDF) membrane (Trans-Blot® Turbo Transfer Pack) using Semidry Blotting (Trans-Blot® Turbo from Bio-Rad, 7 min, 1.3 A/gel, 25 V). For detection, a mouse monoclonal alpha-tubulin antibody (Sigma, #T5168) at a dilution of 1:10'000 in 5% (w/v) fat-free milk powder in Tris-Buffered Saline (TBS) containing 0.1% (v/v) Tween (hereafter TBST) was used as primary antibody. As loading controls, a monoclonal mouse anti-LaminA/C (Cell Signaling, #4777, 1:1,000 dilution), a monoclonal rabbit anti-Histone H3 (Cell Signaling, #9717S, 1:1,000 dilution) and a monoclonal rabbit anti-GAPDH (Cell Signaling, #2118, 1:3,000 dilution) each in 5% (w/v) fat-free milk powder in TBST were used. The secondary antibodies used were a horseradish peroxidase-conjugated goat anti-mouse-IgG (Jackson ImmunoResearch Laboratories, #115-035-146) and a horseradish peroxidase-conjugated goat anti-rabbit-IgG (Jackson ImmunoResearch, #111-035-144) each used at a dilution of 1:5'000 in 5% (w/v) fat-free milk powder in TBST. Decorated bands were revealed by using ECL™ Prime reagent (GE Healthcare) and a Fusion Solo S™ (Vilber Lourmat) detection system.

In vivo MDA-MB-231 Tumor Xenograft Mice

Female athymic nude mice (Crl:NU(NCr)-Foxn1nu, Charles River) were used when ten weeks old with a body weight (BW) range of 19.7-27.1 g on Day 1 of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-o'Cobs™ Laboratory Animal Bedding in static micro-isolators on a 12-hour light cycle at 20-22° C. (68-72° F.) and 40-60% humidity. Charles River Discovery Services North Carolina (CR Discovery Services) specifically complies with the recommendations of the Guide for Care and Use of Laboratory Animals with respect to restraint, husbandry, surgical procedures, feed and fluid regulation, and veterinary care. The animal care and use program at CR Discovery Services is accredited by the Association for Assessment and Accreditation of Laboratory Animal Care International (AAALAC), which assures compliance with accepted standards for the care and use of laboratory animals. These considerations were taken into account in the way that the dosage regimes were designed and implemented.

Tumor Cell Culture, Implantation and Tumor Growth Measurement

The human MDA-MB-231 breast adenocarcinoma cells were grown to mid-log phase in RPMI-1640 medium containing 10% fetal bovine serum, 2 mM glutamine, 100 units/mL sodium penicillin G, 25 µg/mL gentamicin, and 100 µg/mL streptomycin sulfate. The tumor cells were cultured in tissue culture flasks in a humidified incubator at 37° C./5% $CO_2$ and 95% air, harvested during exponential growth and resuspended in cold Phosphate-buffered saline (PBS). Each test animal received a subcutaneous (s.c.) injection of $5 \times 10^6$ MDA-MB-231 cells (0.1 mL cell suspension) into the right flank, and tumor growth was monitored as the average tumor size approached the target range of 100-150 mm$^3$. Tumors were measured (mm) in two dimensions using calipers, and volume was calculated using the formula: Tumor Volume (TV) (mm$^3$)=(width$^2$×length)/2. Eighteen days after tumor cell implantation, on Day 1 of the study, mice with individual tumor volumes ranging from 75 to 172 mm$^3$ were randomized into groups of 8-10 animals, with group mean tumor volumes of 114-124 mm$^3$.

Preparation of BAL101553 and Eribulin Dosing Solutions

BAL0101553 was dissolved in 0.9% NaCl in water buffered to pH 5 with 1% sodium acetate to yield 2, 2.5 and 3 mg/mL dosing solutions, providing 20, 25 and 30 mg/kg dosages, respectively, in 10 mL/kg dosing volumes. Eribulin (purchased from Eisai Co., Lot. No. 6217, 6288, 6289 and 6309) at 0.5 mg/mL concentration was diluted in saline to yield a 0.01, 0.025 and 0.05 mg/mL dosing solutions, providing 0.1, 0.25 and 0.5 mg/kg dosages, respectively, in a dosing volume of 10 mL/kg.

Treatment

Groups of mice (n=8-10) bearing MDA-MB-231 tumors were dosed as outlined in the Tables 1 and 3. All doses were adjusted to 10 mL/kg. The control groups received oral doses of vehicle (pH 5 buffered 0.9% NaCl solution). Eribulin was administered i.v. and BAL101553 orally. When eribulin and BAL0101553 were dosed in combination, Eribulin was administered to all groups first followed by BAL0101553 dosing within 30 minutes of the first regimen.

Analysis of Antitumor Activity, Tumor Regression and Tumor Free Survival Rates (Cures)

Body weights were recorded daily for days 1-5 and then twice weekly until the end of the study and tumor volumes were recorded twice weekly until the end of the experiment. These parameters were analyzed and graphically represented by using GraphPad-Prism™ 5 for Windows according to standard procedure. Tumor growth regression was defined as TV (at day X)-TV (day 1)<0, where X was the day when the vehicle control animals had to be sacrificed according to appropriate guidelines. Tumor free animals at the end of the study time were assessed for residual MDA-MB-231 tumor cells by pathological methods. Skin and subcutaneous tissue including the tumor cell inoculation site from the flank region were resected, preserved in formalin and embedded in paraffin. Sections of approximately 5 µm were mounted on glass slides and stained with hematoxylin/eosin and were evaluated by a trained pathologist, to identify residual tumor cells at the site of injection, and were being reported as positive for the existence of residual tumor cells or as negative for a complete lack of any evidence of residual tumor cells.

Colony Outgrowth Assay

Cells were plated in soft agar in 24-well plates according to the assay introduced by Hamburger & Salmon (Primary bioassay of human tumor stem cells, Science, 1977, 197: 461-463). Each test well contained three layers of equal volume: 2 layers of semi-solid medium (bottom and top layer), and one layer of medium supernatant, with or without test compound (drug overlay on top of the semi-solid medium layer).

The bottom agar layer consisted of 0.2 mL/well IMDM supplemented with 20% (v/v) fetal calf serum, penicillin/streptomycin 50 µg/mL and 0.75% (w/v) bacto agar (BD Biosciences, #214050). For the top agar layer, 10'000-20'000 cells were added to 0.2 mL of the same IMDM medium supplemented with 0.35% (w/v) bacto agar and plated onto the bottom layer. For the drug overlay, the test compounds were applied by continuous exposure in 0.2 mL IMDM medium on top of the two agar layers. The drug overlay was added directly after seeding the cells as 3-fold concentrated solution and changed carefully every 3-4 days. Every 24-well plate contained untreated controls and samples in duplicates. Cultures were incubated at 37° C. and 5% $CO_2$ for 6-14 days. 24 hours prior to evaluation, vital colonies were stained with a sterile aqueous solution of 2-(4-iodophenyl)-3-(4-nitrophenyl)-5-phenyltetrazolium chloride (Sigma, #I-8377, 1 mg/mL, 100 µL/well) (Alley M C et al., Life Sci. 1982, 31:3071-3078) and were counted with an automatic image analysis system (GelCount, Oxford Optronix). IC50-values were determined by plotting compound concentrations versus relative colony counts. Relative drug effects were expressed by the maximum effect of the mean number of colonies in the treated wells in comparison to the control wells.

BAL101553 was used as the dihydrochloride salt and BAL27862 was used as the free base.

Example 1: Antitumor Activity and Induction of Complete Pathological Tumor Regression in the Triple Negative Breast Cancer (TNBC) Xenograft Model MDA-MB-231 after Combined Treatment Modalities with BAL101553 and Eribulin The antitumor effect of the combination treatment with BAL101553 (prodrug of BAL27862) and eribulin was evaluated in the established in vivo subcutaneous mouse xenograft model MDA-MB-231 derived from human triple negative breast cancer (TNBC). In two independent experiments (Example 1A and Example 1B) using various dosing regimens, the anticancer effect of the combination and single agent treatments were determined and compared. In each case, animals which presented no measurable tumor burden after the observation period, and therefore were potentially tumor free, were pathologically assessed for residual tumor cells by a histological approach analyzing the tumor implantation site including surrounding tissue, and if found negative, were declared as cured.

A) BAL101553 Combined with 0.1 mg/kg or 0.5 mg/kg Eribulin

FIGS. 1A to 1E show the antitumor efficacy (-i=mean tumor volume, upper panel) and the body weight changes (-ii=mean %, lower panel) of single agent and combination treatments from day 1 to day 85. Dosing schemes are outlined in Table 1 and schematically depicted in FIG. 7. FIG. 1A shows the vehicle control and all single agent groups whereas FIGS. 1B to 1E show the antitumor activity of the combination treatments as compared to the relevant single agent groups and the vehicle control. Single agent treatments not leading to tumor regressions are depicted until day 25 when the control tumors reached the maximum allowed size, otherwise if regression was observed, the antitumor activity of the treatment groups is shown for the duration of the whole experiment.

Table 2 summarizes the results and shows that 100% of the animals treated with the highest dose combinations (BAL101553/Eribulin: 20/0.5 or 30; 25/0.5) were cured. When the eribulin dose was reduced to 0.1 mg/kg and combined with both BAL101553 regimens (20 or 30; 25 mg/kg) 63% and 37.5% of the animals were cured, respectively. The combinations with low-dose eribulin (0.1 mg/kg) were well tolerated causing no overall changes in body-weight compared to vehicle-control (Table 3), while the higher-dose eribulin combinations (0.5 mg/kg) did impact on body-weight gain. This was most marked with the highest concentration of BAL101553 where overall body-weight loss was observed (Table 3) and one mouse was culled because of a sustained body-weight loss of more than 15%.

These results show that BAL101553 combines with eribulin in a synergistic manner leading to substantially more cures (i.e. complete eradication of the tumor burden) compared to single agent treatment.

TABLE 1

Dosing Scheme Example 1A (E1A)

| Treatment groups | Number of animals per group | Schedule BAL101553 | Eribulin | vehicle |
|---|---|---|---|---|
| Vehicle control (oral) | 8 | — | — | qd x 5, from day 12 qd x 23 |
| BAL101553 20 mg/kg (oral) | 8 | qd x 5, from day 12 qd x 23 | — | — |
| BAL101553 30; 25 mg/kg (oral) | 8 | qd x 5, from day 12 qd x 23 | — | — |
| Eribulin 0.1 mg/kg (i.v.) | 8 | — | q2d x 5, from day 12 q2d x 12 | — |
| Eribulin 0.5 mg/kg (i.v.) | 8 | — | q2d x 5, from day 12 q2d x 12 | — |
| Combi 20/0.1 | 8 | qd x 5, from day 12 qd x 23 | q2d x 5, from day 12 q2d x 12 | — |
| Combi 20/0.5 | 8 | qd x 5, from day 12 qd x 23 | q2d x 5, from day 12 q2d x 12 | — |
| Combi 30; 25/0.1 | 8 | 30 mg/kg qd x 5, 25 mg/kg from day 12 qd x 23 | q2d x 5, from day 12 q2d x 12 | — |
| Combi 30; 25/0.5 | 8 | 30 mg/kg qd x 5, 25 mg/kg from day 12 qd x 20 | q2d x 5, from day 12 q2d x 12 | — |

TABLE 2

Antitumor Efficacy and Induction of Cures in the MDA-MB-231 Xenograft model (E1A)*

| | | | Day 25 | | | Day 85 (endpoint) | |
|---|---|---|---|---|---|---|---|
| Treatment and administration route | Dose and Schedule: D 1-D 9; D 12-D 34 | Treatment until day | T/C | # of regressed tumors (total) | # of tumors with TV ≤ 4 mm³ (total) | # of confirmed cures (total) | % cures |
| BAL101553, p.o. | 20 mg/kg, qd x5/qw; 20 mg/kg, qd. | 34 | 0.21 | 0 (8) | 0 (8) | 0 (8) | 0 |
| BAL101553, p.o. | 30 mg/kg, qd x5/qw; 25 mg/kg, qd. | 34 | 0.07 | 4 (8) | 0 (8) | 0 (8) | 0 |
| Eribulin, i.v. | 0-1 mg/kg, q2d; 0.1 mg/kg, q2d | 34 | 0.13 | 1 (8) | 0 (8) | 0 (8) | 0 |
| Eribulin, i.v. | 0.5 mg/kg, q2d; 0.5 mg/kg, q2d | 34 | −0.09 | 8 (8) | 3 (8) | 1 (8) | 12.5 |

TABLE 2-continued

Antitumor Efficacy and Induction of Cures in the MDA-MB-231 Xenograft model (E1A)*

| Treatment and administration route | Dose and Schedule: D 1-D 9; D 12-D 34 | Treatment until day | T/C | Day 25 # of regressed tumors (total) | # of tumors with TV ≤ 4 mm$^3$ (total) | Day 85 (endpoint) # of confirmed cures (total) | % cures |
|---|---|---|---|---|---|---|---|
| BAL1553, p.o. Eribulin, i.v. | 20 mg/kg; 0.1 mg/kg | 34 | −0.10 | 8 (8) | 6 (8) | 3 (8) | 37.5 |
| BAL1553, p.o. Eribulin, i.v. | 20 mg/kg; 0.5 mg/kg | 34 | −0.11 | 8 (8) | 7 (8) | 8 (8) | 100 |
| BAL1553, p.o. Eribulin, i.v. | 30 mg/kg; 25 mg/kg, 0.1 mg/kg | 34 | −0.11 | 8 (8) | 8 (8) | 5 (8) | 63 |
| BAL1553, p.o. Eribulin, i.v. | 30 mg/kg; 25 mg/kg, 0.5 mg/kg | 31 | −0.11 | 7 (7) | 7 (7) | 6 (6) | 100 |

*The vehicle group was dosed orally (p.o.), daily (qd) on days 1-5 (D 1-D 5) and D 12-D 34. BAL101553 was always administered orally (p.o.) and eribulin always i.v. at the doses shown. The schedules were changed from day-12 in accordance with animal health, and the combinations used the same schedules as those used for the monotherapies.

TABLE 3

Tolerability in the MDA-MB-231 Xenograft model (E1A)*

| Treatment and administration route | Dose and Schedule: D 1-D 9; D 12-D 34 | Treatment until day | Day 25 T/C | Final body-weight (g) | Body-weight change (g) | Mortalities |
|---|---|---|---|---|---|---|
| BAL101553, p.o. | 20 mg/kg, qd x5/qw; 20 mg/kg, qd. | 34 | 1.02 | 26.6 ± 1.6 | 2.8 ± 0.7 | 0/8 |
| BAL101553, p.o. | 30 mg/kg, qd x5/qw; 25 mg/kg, qd. | 34 | 1.00 | 25 ± 1.9 | 2.0 ± 0.8 | 0/8 |
| Eribulin, i.v. | 0.1 mg/kg, q2d; 0.1 mg/kg, q2d | 34 | 1.00 | 25.8 ± 3.0 | 2.1 ± 1.0 | 0/8 |
| Eribulin, i.v. | 0.5 mg/kg, q2d; 0.5 mg/kg, q2d | 34 | 0.96 | 24.4 ± 1.9 | 1.0 ± 1.7 | 0/8 |
| BAL1553, p.o. Eribulin, i.v. | 20 mg/kg; 0.1 mg/kg | 34 | 1.00 | 25.4 ± 2.2 | 2.1 ± 1.1 | 0/8 |
| BAL1553, p.o. Eribulin, i.v. | 20 mg/kg; 0.5 mg/kg | 34 | 0.95 | 24.5 ± 2.5 | 0.8 ± 1.3 | 0/8 |
| BAL1553, p.o. Eribulin, i.v. | 30 mg/kg; 25 mg/kg, 0.1 mg/kg | 34 | 1.00 | 25.0 ± 2.9 | 2.2 ± 1.0 | 0/8 |
| BAL1553, p.o. Eribulin, i.v. | 30 mg/kg; 25 mg/kg, 0.5 mg/kg | 31 | 0.85 | 21.9 ± 1.5 | −1.8 ± 1.9 | 1/8** |

*Results show the mean ± SD for body-weight, BW (g) and the mean change in body-weight (g) from day-0 until day-25. The TC-BW is calculated from the mean fractional-change in the respective treatment-group divided by the mean fractional-change in the vehicle group. The vehicle group was dosed orally (p.o.), daily (qd) on days 1-5 (D 1-D 5) and D 12-D 34. BAL101553 was always administered orally (p.o.) and eribulin always i.v. at the doses shown. The schedules were changed from day-12 in accordance with animal health, and the combinations used the same schedules as those used for the monotherapies.
**animal sacrificed on day 25 and 32 due to body weight loss.

B) BAL101553 Combined with 0.1, 0.25 and 0.5 mg/kg Eribulin

Figure 8:
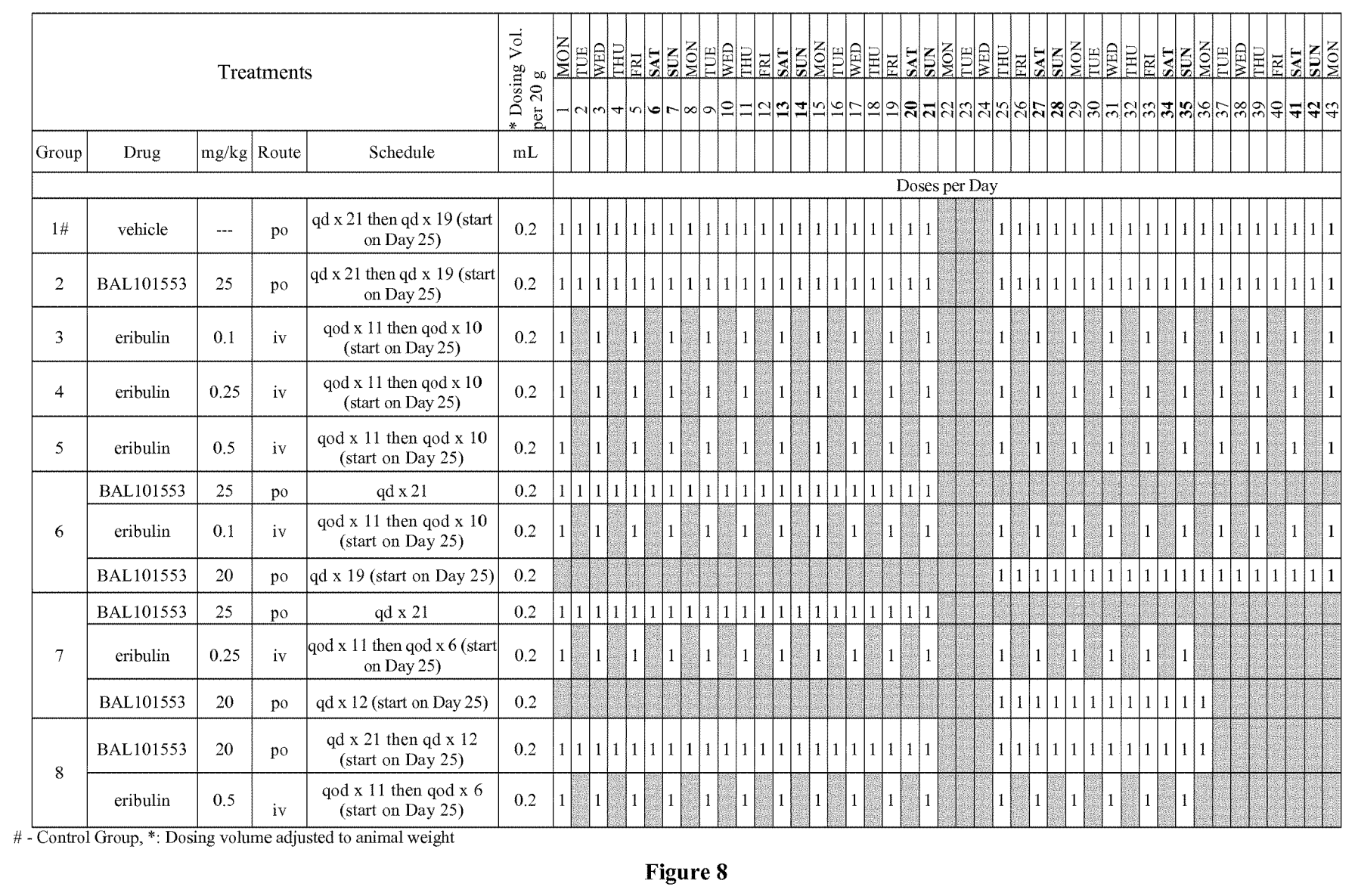

FIGS. 2A to 2D show the antitumor efficacy (-i=mean tumor volume, upper panel) and the body weight changes (-ii=mean %, lower panel) of single agent and combination treatments from day 1 to day 100. Dosing schemes are outlined in Table 4 and schematically depicted in FIG. 8. FIG. 2A shows the tumor growth of vehicle controls and of all the single agent groups whereas FIGS. 2B to 2D show the antitumor activity of the combination treatments as compared to the relevant single agent groups and the vehicle control. All treatments not leading to tumor regression are depicted until day 26 when the control tumors reached the maximum allowed size, otherwise, if regression was observed, the antitumor activity of the treatment groups are shown for the duration of the whole experiment.

Table 5 summarizes the results and shows that, by combining BAL101553 with increasing doses of eribulin, the percentage of cured animals increased substantially relative to the sum of the results of the respective single agent activities. For BAL101553 combinations with 0.1 mg/kg eribulin, the percentage of cured animal increased from 10% to 55%, with 0.25 mg/kg Eribulin from 21% to 88% and with 0.5 mg/kg eribulin, from 70% to 89%. As in the first experiment, the combinations were best tolerated (in terms of body-weight) when the eribulin dose was 0.1 mg/kg (Table 6). However, all 3 combinations resulted in 1/10 mice being culled early because of sustained body-weight loss, although the remainder of the mice (90%) showed on average body-weight gain (Table 6).

These results confirm the observations in Example 1A, namely that BAL101553 combines with eribulin in a synergistic manner leading to substantially more cures (i.e. complete eradication of the tumor burden) compared to single agent treatment.

TABLE 4

Dosing Scheme Example 1B (E1B)

| Treatment groups | Number of animals per group | Schedule BAL101553 | Eribulin | vehicle |
|---|---|---|---|---|
| Vehicle control (oral) | 10 | — | — | qd x 40 |
| BAL101553 25 mg/kg (oral) | 10 | qd x 21, from day 25 qd x 19 | — | — |
| Eribulin 0.1 mg/kg (i.v.) | 10 | — | q2d x 11, from day 25 q2d x 10 | — |
| Eribulin 0.25 mg/kg (i.v.) | 10 | — | q2d x 11, from day 25 q2d x 10 | — |
| Eribulin 0.5 mg/kg (i.v.) | 10 | — | q2d x 11, from day 25 q2d x 10 | — |
| Combi 25; 20/0.1 | 10 | 25 mg/kg qd x 21, 20 mg/kg from day 25 qd x 19 | q2d x 11, from day 25 q2d x 10 | — |
| Combi 25; 20/0.25 | 10 | 25 mg/kg qd x 21, 20 mg/kg from day 25 qd x 19 | q2d x 11, from day 25 q2d x 6 | — |
| Combi 20/0.5 | 10 | 30 mg/kg qd x 5, 25 mg/kg from day 12 qd x 23 | q2d x 11, from day 25 q2d x 6 | — |

TABLE 5

Antitumor Efficacy and Induction of Cures in the MDA-MB-231 Xenograft model (E1B)*

| Treatment and administration route | Dose and Schedule: D 1-D 21; D 25-D 43 | Treatment until day | T/C | Day 26 # of regressed tumors (total) | Day 26 # of tumors with TV ≤ 4 mm$^3$ (total) | Day 100 (endpoint) # of confirmed cures (total) | % cures |
|---|---|---|---|---|---|---|---|
| BAL101553, p.o. | 20 mg/kg, qd; 20 mg/kg, qd | 43 | 0.12 | 1 (10) | 0 (10) | 1 (10) | 10 |
| Eribulin, i.v. | 0.1 mg/kg, q2d; 0.1 mg/kg, q2d | 43 | 0.12 | 2 (10) | 0 (10) | 0 (10) | 0 |
| Eribulin, i.v. | 0.25 mg/kg, q2d; 0.25 mg/kg, q2d | 43 | −0.05 | 8 (10) | 1 (10) | 1 (9) | 11 |
| Eribulin, i.v. | 0.5 mg/kg, q2d; 0.5 mg/kg, q2d | 43 | −0.09 | 10 (10) | 2 (10) | 6 (10) | 60 |
| BAL1553, p.o. Eribulin, i.v. | 25 mg/kg; 20 mg/kg, 0.1 mg/kg | 43 | −0.10 | 9 (9) | 2 (9) | 5 (9) | 55 |
| BAL1553, p.o. Eribulin, i.v./ Eri | 25 mg/kg; 20 mg/kg, 0.25 mg/kg | 36 | −0.10 | 9 (9) | 4 (9) | 7 (8) | 88 |
| BAL1553, p.o. Eribulin, i.v. | 20 mg/kg, 0.5 mg/kg | 36 | −0.10 | 9 (9) | 5 (9) | 8 (9) | 89 |

*The vehicle group was dosed orally (p.o.), daily (qd) on days 1-21 (D 1-D 21) and D 25-D 43. BAL101553 was always administered orally (p.o.) and eribulin always i.v. at the doses shown. The schedules were changed from day −25 in accordance with animal health, and the combinations used the same schedules as those used for the monotherapies, except that in the combinations using higher eribulin doses (0.25 and 0.5 mg/kg) dosing ceased one week earlier.

TABLE 6

Tolerability in the MDA-MB-231 Xenograft model (E1B)*

| Treatment and administration route | Dose and Schedule: D 1-D 21; D 25-D 43 | Treatment until day | Day 26 T/C | Final body-weight (g) | Body-weight change (g) | Mortalities |
|---|---|---|---|---|---|---|
| BAL101553, p.o. | 20 mg/kg, qd; 20 mg/kg, qd | 43 | 1.04 | 25.9 ± 1.4 | 2.6 ± 0.7 | 0/10 |
| Eribulin, i.v. | 0.1 mg/kg, q2d; 0.1 mg/kg, q2d | 43 | 1.09 | 27.9 ± 2.7 | 3.9 ± 1.1 | 0/10 |
| Eribulin, i.v. | 0.25 mg/kg, q2d; 0.25 mg/kg, q2d | 43 | 1.02 | 26.6 ± 1.7 | 2.3 ± 1.0 | 0/10+ |
| Eribulin, i.v. | 0.5 mg/kg, q2d; 0.5 mg/kg, q2d | 43 | 1.03 | 25.5 ± 1.5 | 2.3 ± 0.9 | 0/10 |
| BAL1553, p.o. Eribulin, i.v. | 25 mg/kg; 20 mg/kg, 0.1 mg/kg | 43 | 1.00 | 24.8 ± 2.7 | 1.6 ± 2.2 | 1/10** |
| BAL1553, p.o. Eribulin, i.v./ Eri | 25 mg/kg; 20 mg/kg, 0.25 mg/kg | 36 | 0.97 | 25.3 ± 3.4 | 0.9 ± 2.6 | 1/10**+ |
| BAL1553, p.o. Eribulin, i.v. | 20 mg/kg, 0.5 mg/kg | 36 | 0.97 | 24.9 ± 2.7 | 0.8 ± 4 | 1/10** |

*Results show the mean ± SD for body-weight, BW (g) and the mean change in body-weight (g) from day-0 until day-26. The TC-BW is calculated from the mean fractional-change in the respective treatment-group divided by the mean fractional-change in the vehicle group. The vehicle group was dosed orally (p.o.), daily (qd) on days 1-21 (D 1-D 21) and D 25-D 43. BAL101553 was always administered orally (p.o.) and eribulin always i.v. at the doses shown. The schedules were changed from day-25 in accordance with animal health, and the combinations used the same schedules as those used for the monotherapies, except that in the combinations using higher eribulin doses (0.25 and 0.5 mg/kg) dosing ceased one week earlier.
+non-treatment related death at day 96 and 43,
**animal sacrificed on day 18 and 22 respectively, due to body weight loss.

Example 2: In Vitro Apoptosis Induction by BAL27862 and Eribulin, Alone and in Combination in Jurkat-GFP and NCI-H460-GFP Cells A) Time-Dependent Induction of Apoptosis in Jurkat-GFP Cells BAL27862 potently induces apoptosis in Jurkat-GFP cells (EC50 of 15 nM) and has a typical sigmoidal dose-response curve reaching a maximum at 70-80%, while eribulin possesses a stronger potency (EC50 0.8 nM) with a maximal apoptosis induction of about 70% (data not shown). The combination of BAL27862 and eribulin was found not to increase the maximum extent of apoptosis (data not shown). Thus, when BAL27862 and eribulin are dosed at high concentrations, interactions between the two compounds are likely to be underestimated due to the inability of the compounds to produce activity in combination which exceeds the maximum possible apoptosis. Therefore the concentrations tested for the combinations of BAL27862 and eribulin were below their EC50 value. FIG. 3 demonstrates that the time-dependent induction of apoptosis in Jurkat-GFP cells when BAL27862 and eribulin were combined was much stronger and faster than when BAL27862 or eribulin were used alone. This shows that the combination of BAL27862 and eribulin more than additively (i.e. synergistically) induces apoptosis in Jurkat-GFP cells.

B) Induction of Apoptosis in NCI-H460-GFP Cells

BAL27862 and eribulin also potently induce apoptosis in NCI-H460-GFP cells (EC50: 24 nM and 1 nM, respectively) reaching a maximum between 80-90% (data not shown). When BAL27862 and eribulin were combined at concentrations below their respective EC50 values (see reason described above for Jurkat-GFP cells) they demonstrated highly synergistic interactions exceeding the expected additive activity. This is shown in FIG. 4 where three different concentrations of BAL27862 were combined with two concentrations of eribulin. Six combinations were tested and, in each case, a more than additive (i.e. synergistic) interaction regarding induction of apoptosis was demonstrated.

Example 3: Cellular Microtubule Destabilization Assay in MDA-MB-231 Cells

BAL27862 (parent drug of BAL101553) and eribulin are both microtubule interacting agents and show microtubule-destabilizing activity in vitro. Since both agents bind to distinct binding pockets on tubulin, interactions upon binding of both agents might have an influence on their destabilization property in a positive or negative way. The combination effect of BAL27862 and eribulin was tested on microtubule destabilization in the MDA-MB-231 TNBC cell line using physiologically relevant compound concentrations based on anti-proliferative IC50 potencies determined by soft agar clonogenic assay with this cell line (BAL27862: 12 nM, eribulin: 0.1 nM) (data not shown). For that purpose MDA-MB-231 cells were incubated with single agents or combinations thereof, extracted and subsequently separated into soluble tubulin (soluble fraction: S) and polymerized tubulin (particulate fractions: P) by fractionation. By Western blotting the soluble vs. particulate fractions were then compared to assess the destabilizing potential of the agent or combination of agents used on the cell line.

Figure 5A:
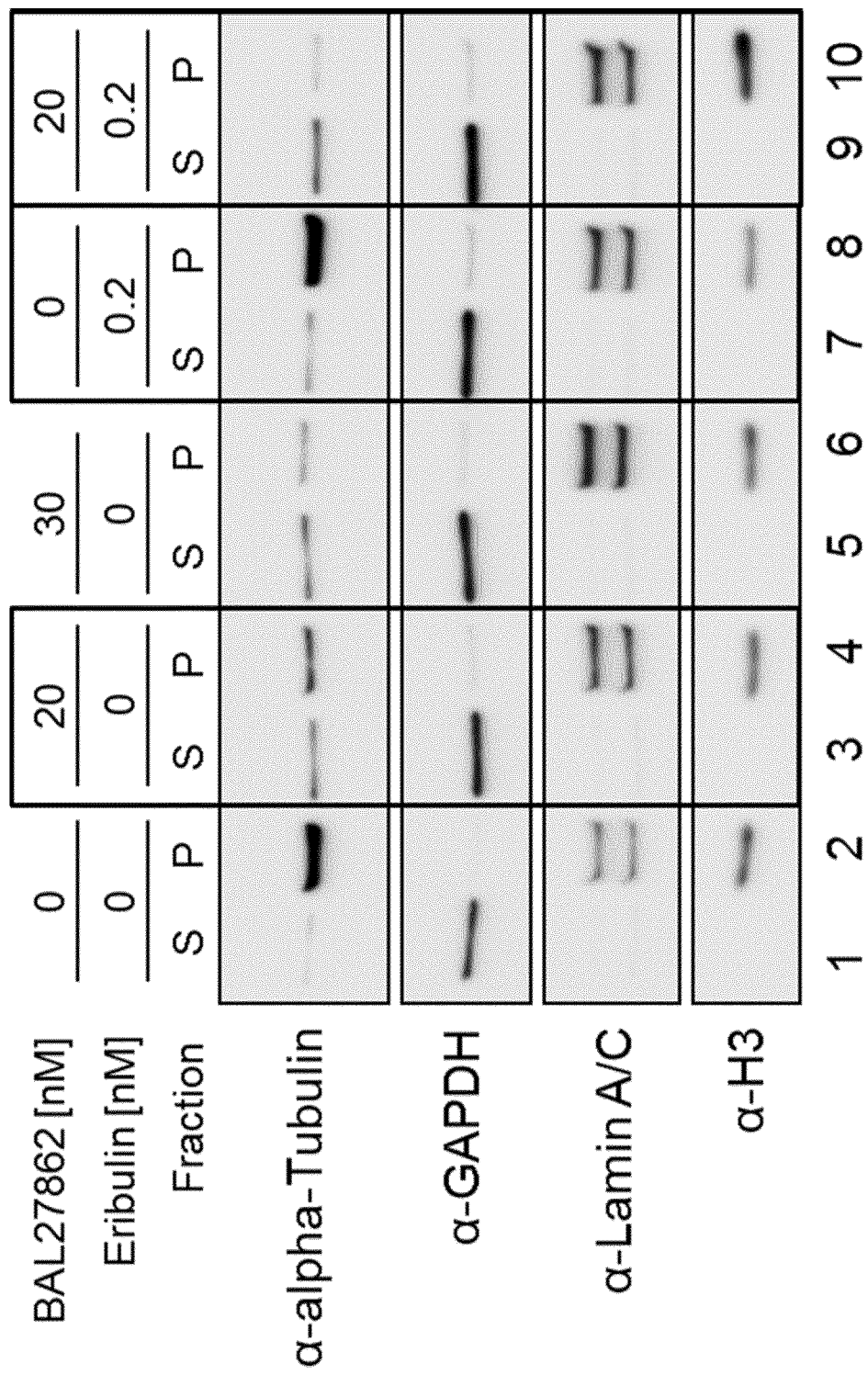
FIG. 5A and FIG. 5B illustrate that the cellular microtubule destabilizing effect is strongly enhanced by combining BAL27862 with eribulin. MDA-MB-231 cells were incubated either with BAL27862, eribulin or with both agents simultaneously at the indicated concentrations. Cells were then processed for separation of soluble tubulin (S) and microtubules (P) and analyzed by Western blotting. The signal ratio of S and P reflects the relative amount of soluble and polymerized tubulin. Equal loading and fractionation into soluble and particulate fraction as control is shown by the loading controls GAPDH (soluble) α-Lamin A/C (particulate) and α-histone 3 (particulate).
Figure 5B:
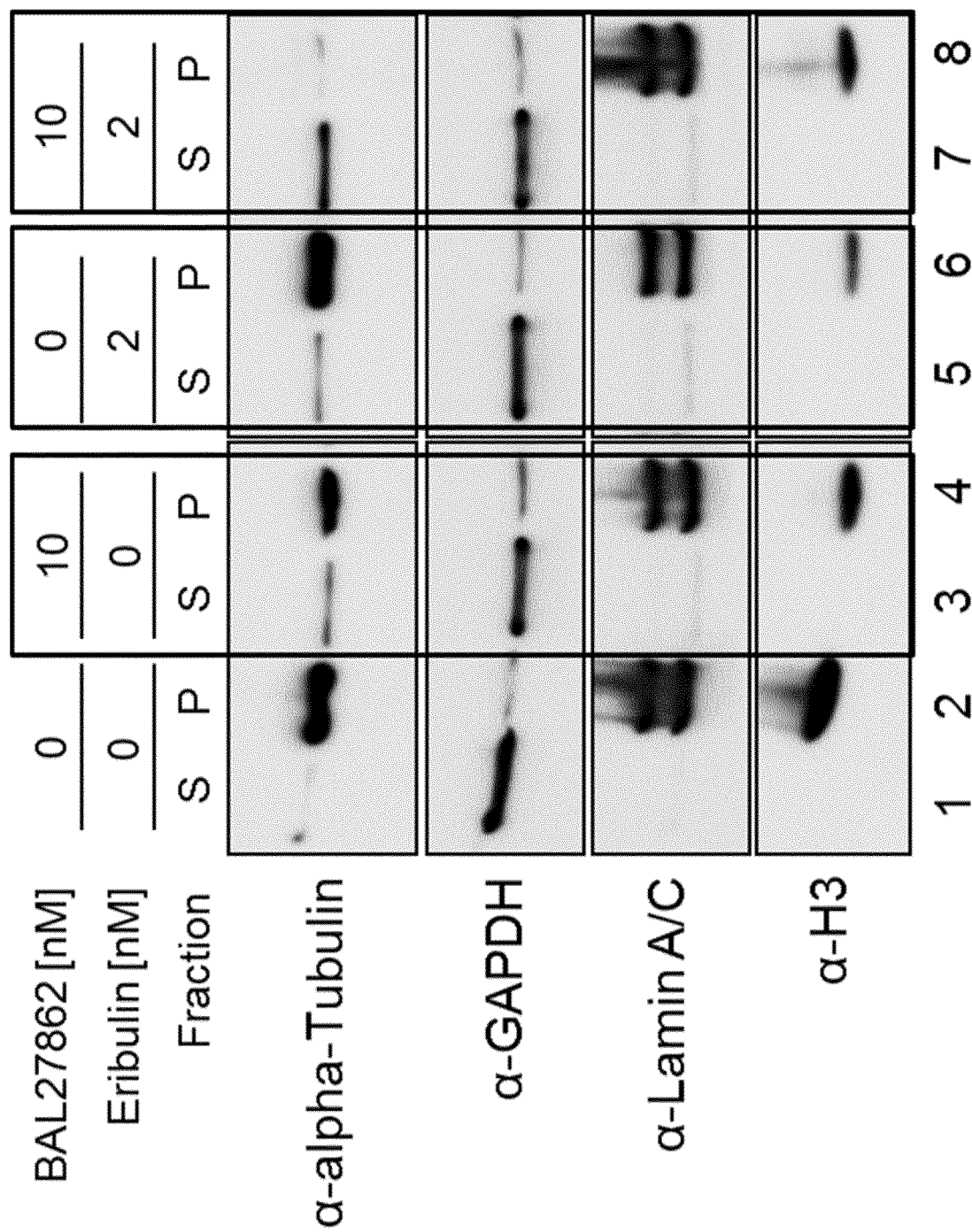

FIG. 5A presents the data in respect of the combination of 20 nM BAL27862 and 0.2 nM eribulin (lanes 9 & 10) in comparison to single agent activity (BAL27862: lanes 3 and 4, eribulin: lanes 7 and 8) and control (lanes 1 and 2). FIG. 5B presents the data for the combination of 10 nM BAL27862 and 2 nM eribulin (lanes 7 & 8) in comparison to single agent activity (BAL27862: lanes 3 & 4, eribulin: lanes 5 & 6) and control (lanes 1 & 2). It can be seen that the combined treatment at the indicated concentrations in both FIGS. 5A and 5B, shifted the tubulin almost completely into the soluble fraction (fraction S) indicating a strong microtubule destabilizing activity. This is in contrast to what was observed by single agent treatment. Eribulin single agent treatment at both concentrations tested (0.2 nM and 2 nM in FIG. 5A and FIG. 5B respectively) induced only a small increase in soluble tubulin compared to control lanes, whereas BAL27862 as single agent showed a concentration-dependent but incomplete destabilizing effect (compare lanes 3 & 4 with 5 & 6 for 20 and 30 nM in FIG. 5A, respectively). These results indicate strong mechanistic evidence for a synergistic interaction between BAL27862 and eribulin.

Figure 6:
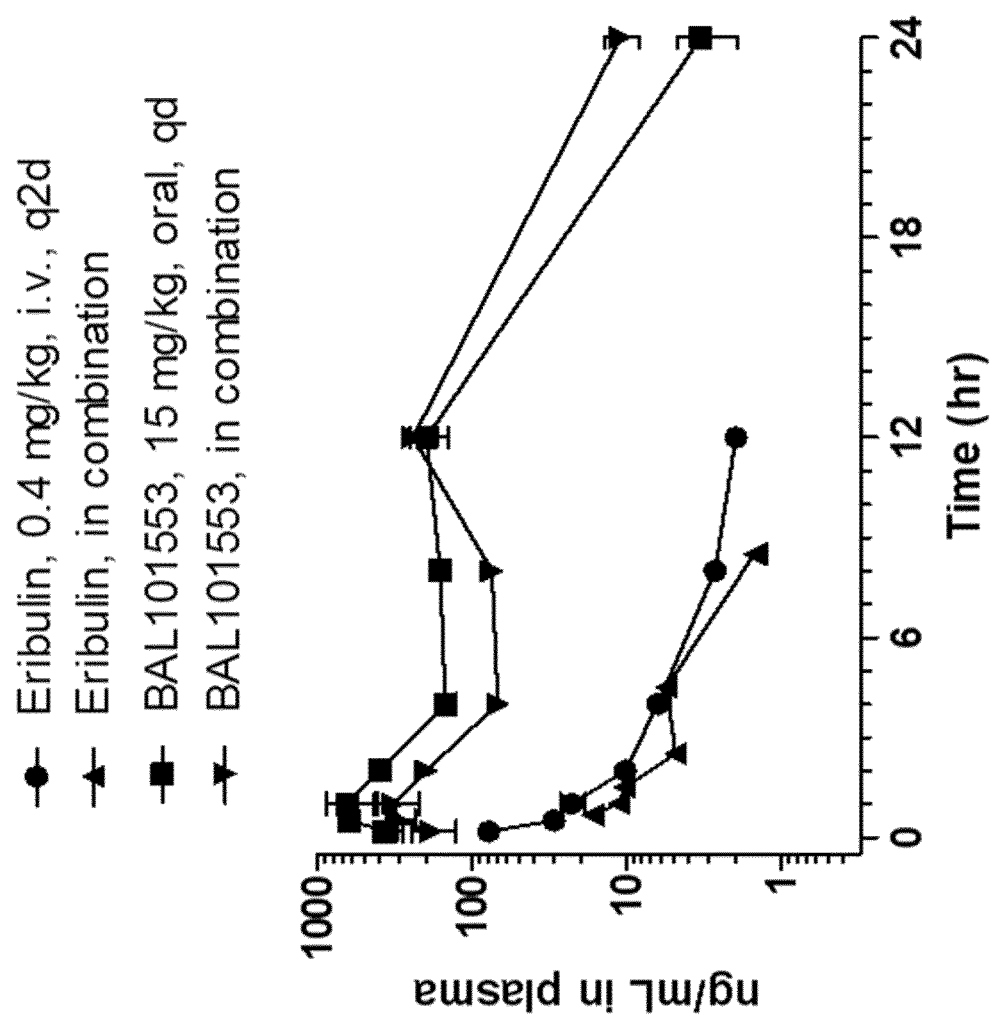
FIG. 6 shows the determination of the pharmacokinetic profile of BAL27862, eribulin and the combined treatment thereof in mouse plasma. Female NCI Ath/nu non-tumor bearing mice were treated either with BAL101553, eribulin or with a combination of BAL101553 and eribulin where eribulin was administered 30 minutes before BAL101553. Control animals received vehicle control. The mice were dosed until steady state was reached (BAL101553 was dosed daily and eribulin was dosed once every two days, the doses used for the combination-treatment matched those used in the monotherapy). Blood was taken from every animal according to a determined schedule covering a time window of 10 minutes to 24 hours, processed for plasma and subsequently analyzed by LC-MS/MS for the determination of BAL27862 (parent drug of BAL101553) and eribulin concentrations (ng/ml plasma). Data points represent mean values of ng/ml plasma concentration+/−SEM (n=3 animals).

Example 4: Determination of the Pharmacokinetic Profile of BAL27862, Eribulin and the Combined Treatment Thereof in Mouse Plasma The in vivo combination of BAL101553 with eribulin in the TNBC xenograft model MDA-MB-231 led to a higher proportion of cures or tumor free animals than observed in the single agent treatment groups. In order to rule out drug-drug interactions as an explanation for this observation (e.g. combined treatment may influence the exposure to BAL27862 or eribulin) pharmacokinetic studies in non-tumor bearing mice of the same strain were performed. The mice were either treated with BAL101553, eribulin or the combination thereof, and plasma concentrations of BAL27862 and eribulin at various time points were determined (FIG. 6). The analysis showed that the plasma concentrations of either compound did not change significantly if the compounds were administered as single agents or in combination.

This finding indicates that the observed antitumor activity of the combination treatments leading to an increased number of cured animals is not due to increased drug exposure as a consequence of any drug-drug interaction, but is rather a consequence of mechanistic interactions on a molecular level. This finding is supported by the in vitro data in Examples 2 and 3 which demonstrate a greater than additive induction of both microtubule destabilization and apoptosis in human tumor cell lines.

Example 5: Determination of Drug Interaction in Cell Lines by Soft Agar Assay The combination of BAL101553 with eribulin was tested in various cell lines by soft agar assay. Table 1 and Table 2 present the results according to coefficient of drug interaction based on colony number (Table 1) and total area of colonies (Table 2). In both cases the coefficient of drug interaction is calculated according to the formula described in Zhao et al., J Intercult Ethnopharmacol. 2014, 3(2): 68-72):

(combination/untreated)/[(compound1/untreated)×(compound2/untreated)]

A coefficient of drug interaction >1 indicates antagonism, a coefficient of drug interaction=1 indicates additive effects and a coefficient of drug interaction <1 indicates synergism (≤0.7 is statistically significant and labeled by *).

TABLE 7

Coefficient of drug interaction of indicated cell lines and combinations determined by soft agar assay (based on colony number)

| Cell line | | | IC50 of BAL27862* | |
|---|---|---|---|---|
| | | | 1/2x | 1x |
| MDA-MB-231 | IC50 of Eribulin* | 8/1000x | 0.90 | 0.81 |
| | | 1/10x | 0.82 | 0.60* |
| | | 1/20x | 0.73 | 0.53* |
| MDA-MB-231 | IC50 of Eribulin* | 8/1000x | 0.96 | 0.48* |
| | | 1/10x | 0.78 | 1.04 |
| | | 1/20x | 1.25 | 0.73 |

TABLE 7-continued

Coefficient of drug interaction of indicated cell lines and combinations determined by soft agar assay (based on colony number)

| Cell line | | | IC50 of BAL27862* | |
|---|---|---|---|---|
| | | | 1/2x | 1x |
| HCC1395 | IC50 of Eribulin* | 8/1000x | 0.92 | 0.49* |
| | | 1/10x | 0.70* | 1.07 |
| | | 1/20x | 1.00 | 0.62* |
| A549 | IC50 of Eribulin* | 8/1000x | 0.79 | 0.63* |
| | | 1/10x | 0.57* | 0.78 |
| | | 1/20x | 0.75 | 0.75 |
| HCT116 | IC50 of Eribulin* | 8/1000x | 0.83 | 0.76 |
| | | 1/10x | 0.82 | 1.19 |
| | | 1/20x | 0.94 | 0.32* |
| MiaPaCa2 | IC50 of Eribulin* | 8/1000x | 0.98 | 0.89 |
| | | 1/10x | 0.88 | 0.68* |
| | | 1/20x | 0.85 | 0.24* |

*IC50 values in soft agar assay of the individual cell lines used:
MDA-MB-231 (12 nM BAL27862; 111 pM Eribulin);
HCC1395 (10 nM BAL27862; 500 pM Eribulin);
A549 (25 nM BAL27862; 250 pM Eribulin);
HCT116 (18 nM BAL27862; 1000 pM Eribulin);
MiaPaCa2 (9 nM BAL27862; 500 pM Eribulin)

TABLE 8

Coefficient of drug interaction of indicated cell lines and combinations determined by soft agar assay (based on total area of colonies)

| Cell line | | | IC50 of BAL27862* | |
|---|---|---|---|---|
| | | | 1/2x | 1x |
| MDA-MB-231 | IC50 of Eribulin* | 8/1000x | 0.83 | 0.72 |
| | | 1/10x | 0.75 | 0.47* |
| | | 1/20x | 0.61* | 0.43* |
| MDA-MB-231 | IC50 of Eribulin* | 8/1000x | 0.94 | 0.44* |
| | | 1/10x | 0.67* | 1.00 |
| | | 1/20x | 1.23 | 0.78 |
| HCC1395 | IC50 of Eribulin* | 8/1000x | 1.04 | 0.55* |
| | | 1/10x | 0.58* | 0.99 |
| | | 1/20x | 0.82 | 0.60* |
| A549 | IC50 of Eribulin* | 8/1000x | 0.86 | 0.66* |
| | | 1/10x | 0.45* | 0.73 |
| | | 1/20x | 0.60* | 0.73 |
| HCT116 | IC50 of Eribulin* | 8/1000x | 0.94 | 0.90 |
| | | 1/10x | 0.74 | 1.32 |
| | | 1/20x | 0.88 | 0.27* |
| MiaPaCa2 | IC50 of Eribulin* | 8/1000x | 1.11 | 0.92 |
| | | 1/10x | 0.86 | 0.63* |
| | | 1/20x | 0.82 | 0.20* |

*IC50 values in soft agar assay of the individual cell lines used:
MDA-MB-231 (12 nM BAL27862; 111 pM Eribulin);
HCC1395 (10 nM BAL27862; 500 pM Eribulin);
A549 (25 nM BAL27862; 250 pM Eribulin);
HCT116 (18 nM BAL27862; 1000 pM Eribulin);
MiaPaCa2 (9 nM BAL27862; 500 pM Eribulin)

The following numbered paragraphs describe particular embodiments of the invention.

Paragraph 1. A pharmaceutical combination comprising (a) a compound of formula I

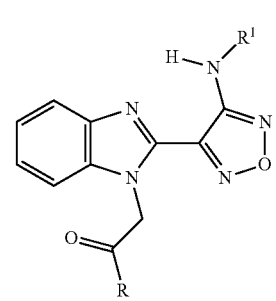

(I)

wherein

R represents phenyl or pyridinyl;

wherein phenyl is optionally substituted by one or two substituents independently selected from lower alkyl, lower alkoxy, hydroxyl, amino, lower alkylamino, lower dialkylamino, acetylamino, halogen and nitro;

and wherein pyridinyl is optionally substituted by amino or halogen;

R1 represents hydrogen or cyano-lower alkyl;

and wherein the prefix lower denotes a radical having up to and including a maximum of 4 carbon atoms;

or a pharmaceutically acceptable derivative thereof;

and (b) a compound of formula II (eribulin)

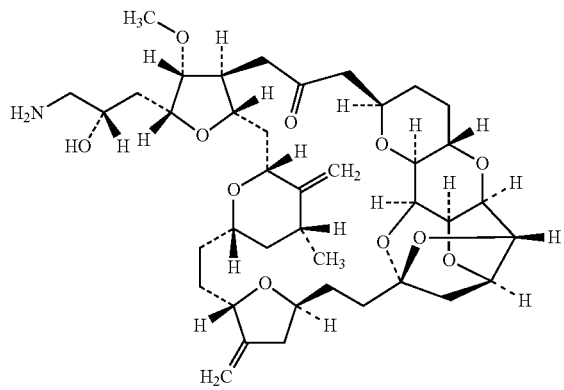

(II)

or a pharmaceutically acceptable salt thereof.

Paragraph 2. The pharmaceutical combination according to Paragraph 1, wherein the compound of formula I or pharmaceutically acceptable derivative thereof is a compound of formula I-A

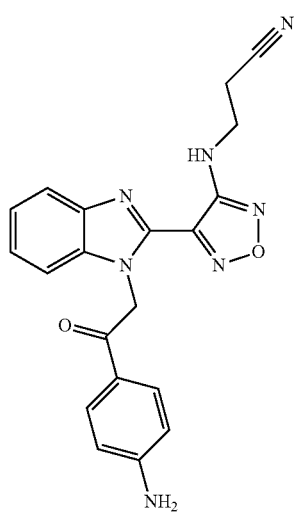

(I-A)

or a pharmaceutically acceptable derivative thereof.

Paragraph 3. The pharmaceutical combination according to Paragraph 2, wherein the compound of formula I or pharmaceutically acceptable derivative thereof is the compound of formula I-A or pharmaceutically acceptable salt thereof, or a compound of formula I-B

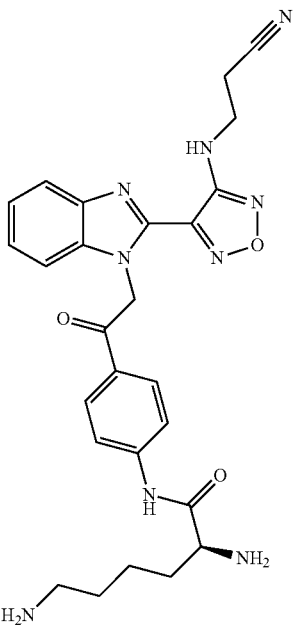

(I-B)

or a pharmaceutically acceptable salt thereof.

Paragraph 4. The pharmaceutical combination according to Paragraph 3, wherein the compound of formula I or pharmaceutically acceptable derivative thereof is the dihydrochloride salt of the compound of formula I-B.

Paragraph 5. The pharmaceutical combination according to any one of Paragraphs 1 to 4, wherein the compound of formula II or a pharmaceutically acceptable salt thereof is eribulin mesylate.

Paragraph 6. The pharmaceutical combination according to any one of Paragraphs 1 to 5, wherein the compound of formula I or pharmaceutically acceptable derivative thereof and the compound of formula II or pharmaceutically acceptable salt thereof are comprised in separate pharmaceutical compositions.

Paragraph 7. The pharmaceutical combination according to any one of Paragraphs 1 to 6, wherein the mole ratio of the mole amount of the compound of formula I or pharmaceutically acceptable derivative thereof to the mole amount of the compound of formula II or pharmaceutically acceptable salt thereof is 1:1 to 800:1.

Paragraph 8. The pharmaceutical combination according to Paragraph 7, wherein the mole ratio is 20:1 to 300:1.

Paragraph 9. The pharmaceutical combination according to Paragraph 7, wherein the mole ratio is 30:1 to 250:1.

Paragraph 10. A method for treating a neoplastic disease in a subject in need thereof, in particular a human, comprising administering to the subject a therapeutically effective amount of a pharmaceutical combination as defined in any one of Paragraphs 1 to 9.

Paragraph 11. The method according to Paragraph 10, wherein the compound of formula I or pharmaceutically acceptable derivative thereof and the compound of formula II or pharmaceutically acceptable salt thereof are administered simultaneously, sequentially or separately to the subject.

Paragraph 12. The method according to Paragraph 10 or Paragraph 11, wherein the compound of formula I or pharmaceutically acceptable derivative thereof and the compound of formula II or pharmaceutically acceptable salt thereof are administered to the subject according to cyclic treatment schedules;
wherein when the treatment cycles are of the same duration the mole ratio of the total mole amount of the doses of the compound of formula I or pharmaceutically acceptable derivative thereof to the total mole amount of the doses of the compound of formula II or pharmaceutically acceptable salt thereof administered to the subject over the respective treatment cycles is 1:1 to 800:1;
and wherein when the treatment cycles are of different duration the ratio of the total mole amount of the doses of the compound of formula I or pharmaceutically acceptable derivative thereof to the total mole amount of the doses of the compound of formula II or pharmaceutically acceptable salt thereof administered to the subject over a theoretical period of time corresponding to a common multiple of the duration of the respective treatment cycles is 1:1 to 800:1.

Paragraph 13. The method according to Paragraph 12, wherein the mole ratio is 20:1 to 300:1.

Paragraph 14. The method according to Paragraph 12, wherein the mole ratio is 30 to 250:1.

Paragraph 15. The method according to Paragraph 10 or Paragraph 11, wherein the compound of formula I or pharmaceutically acceptable derivative thereof is administered to the subject according to a continuous treatment schedule and the compound of formula II or pharmaceutically acceptable salt thereof is administered to the subject according to a cyclic treatment schedule and wherein the mole ratio of the total mole amount of the doses of the compound of formula I or pharmaceutically acceptable derivative thereof administered to the subject over a period of the same duration of the treatment cycle of the compound of formula II or pharmaceutically acceptable salt thereof to the total mole amount of the doses of the compound of formula II or pharmaceutically acceptable salt thereof administered to the subject over the treatment cycle is 1:1 to 800:1.

Paragraph 16. The method according to Paragraph 15, wherein the mole ratio is 20:1 to 300:1.

Paragraph 17. The method according to Paragraph 15, wherein the mole ratio is 30:1 to 250:1.

Paragraph 18. The method according to any one of Paragraphs 10 to 17, wherein the compound of formula I or pharmaceutically acceptable derivative thereof is administered orally at dose corresponding to the mole equivalent of about 2 mg to about 30 mg of the dihydrochloride salt of the compound of formula I-B per day on days when administered, and wherein the compound of formula II or pharmaceutically acceptable salt thereof is administered intravenously at a dose corresponding to the mole equivalent of eribulin mesylate of about 0.1 mg/m$^2$ to about 2 mg/m$^2$ per week during weeks when administered.

Paragraph 19. The method according to Paragraph 18, wherein the compound of formula I or pharmaceutically acceptable derivative thereof is administered at a dose corresponding to the mole equivalent of about 4 mg to about 20 mg of the dihydrochloride salt of the compound of formula I-B per day on days when administered.

Paragraph 20. The method according to Paragraph 18, wherein the compound of formula I or pharmaceutically acceptable derivative thereof is administered at a dose corresponding to the mole equivalent of about 8 mg to about 20 mg of the dihydrochloride salt of the compound of formula I-B per day on days when administered.

Paragraph 21. The method according to any one of Paragraph 18 to 20, wherein the compound of formula I or pharmaceutically acceptable derivative thereof is administered to the subject at least once per day.

Paragraph 22. The method according to any one of Paragraphs 18 to 21, wherein the compound of formula II or pharmaceutically acceptable salt thereof is administered at a dose corresponding to the mole equivalent of eribulin mesylate of about 0.3 mg/m$^2$ to about 1.5 mg/m$^2$ per week during weeks when administered.

Paragraph 23. The method according to any one of Paragraphs 18 to 22, wherein the compound of formula II or pharmaceutically acceptable salt thereof is administered to the subject according to a 21-day treatment cycle with administration initiated on days 1 and 8, or according to a 28-day treatment cycle with administration initiated on days 1 and 15.

Paragraph 24. The method according to any one of Paragraphs 10 to 17, wherein the compound of formula I or pharmaceutically acceptable derivative thereof is administered intravenously at a dose corresponding to the mole equivalent of about 15 mg/m$^2$ to about 160 mg/m$^2$ of the dihydrochloride salt of the compound of formula I-B per week during weeks when administered, and wherein the compound of formula II or pharmaceutically acceptable salt thereof is administered intravenously at a dose corresponding to the mole equivalent of eribulin mesylate of about 0.1 mg/m$^2$ to about 2 mg/m$^2$ per week during weeks when administered.

Paragraph 25. The method according to Paragraph 24, wherein the compound of formula I or pharmaceutically acceptable derivative thereof is administered at a dose corresponding to the mole equivalent of about 30 mg/m$^2$ to about 100 mg/m$^2$ of the dihydrochloride salt of the compound of formula I-B per week during weeks when administered.

Paragraph 26. The method according to Paragraph 24, wherein the compound of formula I or pharmaceutically acceptable derivative thereof is administered at a dose corresponding to the mole equivalent of about 30 mg/m$^2$ to about 70 mg/m$^2$ of the dihydrochloride salt of the compound of formula I-B per week during weeks when administered.

Paragraph 27. The method according to any one of Paragraphs 24 to 26, wherein the compound of formula I or pharmaceutically acceptable derivative thereof is administered according to a 21-day treatment cycle with administration initiated on days 1 and 8, or a 28-day treatment cycle with administration initiated on days 1, 8 and 15.

Paragraph 28. The method according to any one of Paragraphs 24 to 27, wherein the compound of formula II or pharmaceutically acceptable salt thereof is administered intravenously at a dose corresponding to the mole equivalent of eribulin mesylate of about 0.3 mg/m$^2$ to about 1.5 mg/m$^2$ per week during weeks when administered.

Paragraph 29. The method according to any one of Paragraphs 24 to 28, wherein the compound of formula II or pharmaceutically acceptable salt thereof is administered according to a 21-day treatment cycle with administration initiated on days 1 and 8, or according to a 28-day treatment cycle with administration initiated on days 1 and 15.

Paragraph 30. The method according to any one of Paragraphs 10 to 29, wherein the neoplastic disease is a solid tumour.

Paragraph 31. The method according to any one of Paragraphs 10 to 30, wherein the neoplastic disease is selected from the group consisting of epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, myeloproliferative disorders, lymphoproliferative disorders and myelodysplastic syndromes.

Paragraph 32. The method according to any one of Paragraphs 10 to 31, wherein the disease is a cancer.

Paragraph 33. The method according to Paragraph 32, wherein the cancer in terms of the organs and parts of the body affected is selected from the brain, breast (including triple negative breast cancer), cervix, ovaries, colon, rectum, (including colon and rectum i.e. colorectal cancer), lung, (including small cell lung cancer, non-small cell lung cancer, large cell lung cancer and mesothelioma), endocrine system, bone, adrenal gland, thymus, liver, stomach, intestine, (including gastric cancer), pancreas, bone marrow, haematological malignancies, (such as lymphoma, leukaemia, myeloma or lymphoid malignancies), bladder, urinary tract, kidneys, skin, thyroid, head, neck, prostate and testis.

Paragraph 34. The method according to Paragraph 32, wherein the cancer is selected from brain cancer (e.g. glioblastoma), breast cancer (including triple negative breast cancer), prostate cancer, cervical cancer, ovarian cancer, gastric cancer, colorectal cancer, pancreatic cancer, liver cancer, brain cancer, neuroendocrine cancer, lung cancer, kidney cancer, haematological malignancies, melanoma and sarcomas.

Paragraph 35. The method according to Paragraph 34, wherein the cancer is breast cancer.

Paragraph 36. A method for treating a neoplastic disease in a subject in need thereof, in particular a human, comprising administering to the subject a therapeutically effective amount of a compound of formula I or a pharmaceutically acceptable derivative thereof as defined in any one of Paragraphs 1 to 4, which subject is undergoing or will undergo treatment with a compound of formula II or pharmaceutically acceptable salt thereof as defined in Paragraph 1 or Paragraph 5.

Paragraph 37. The method according to Paragraph 36, wherein the compound of formula I or a pharmaceutically acceptable derivative thereof is administered to the subject as defined in any one of Paragraphs 11 to 29.

Paragraph 38. The method according to Paragraph 34 or Paragraph 35, wherein the neoplastic disease is as defined in any one of Paragraphs 30 to 35.

Paragraph 39. A method for treating a neoplastic disease in a subject in need thereof, in particular a human, comprising administering to the subject a therapeutically effective amount of a compound of formula II or a pharmaceutically acceptable salt thereof as defined in Paragraph 1 or Paragraph 5, which subject is undergoing or will undergo treatment with a compound of formula I or pharmaceutically acceptable derivative thereof as defined in any one of Paragraphs 1 to 4.

Paragraph 40. The method according to Paragraph 39, wherein the compound of formula II or a pharmaceutically acceptable salt thereof is administered to the subject as defined in any one of Paragraphs 11 to 29.

Paragraph 41. The method according to Paragraph 34 or Paragraph 35, wherein the neoplastic disease is as defined in any one of Paragraphs 30 to 35.

Paragraph 42. A pharmaceutical combination as defined in any one of Paragraphs 1 to 9, for use in the treatment of a neoplastic disease in a subject, in particular a human.

Paragraph 43. The pharmaceutical combination for use according to Paragraph 42, wherein the compound of formula I or pharmaceutically acceptable derivative thereof and the compound of formula II or pharmaceutically acceptable salt thereof are for simultaneous, sequential or separate administration to the subject.

Paragraph 44. The pharmaceutical combination for use according to Paragraph 42 or Paragraph 43, wherein the compound of formula I or pharmaceutically acceptable derivative thereof and the compound of formula II or pharmaceutically acceptable salt thereof are administered to the subject according to cyclic treatment schedules;
wherein when the treatment cycles are of the same duration the mole ratio of the total mole amount of the doses of the compound of formula I or pharmaceutically acceptable derivative thereof to the total mole amount of the doses of the compound of formula II or pharmaceutically acceptable salt thereof administered to the subject over the respective treatment cycles is 1:1 to 800:1;
and wherein when the treatment cycles are of different duration the ratio of the total mole amount of the doses of the compound of formula I or pharmaceutically acceptable derivative thereof to the total mole amount of the doses of the compound of formula II or pharmaceutically acceptable salt thereof administered to the subject over a theoretical period of time corresponding to a common multiple of the duration of the respective treatment cycles is 1:1 to 800:1.

Paragraph 45. The pharmaceutical combination for use according to Paragraph 44, wherein the mole ratio is 20:1 to 300:1.

Paragraph 46. The pharmaceutical combination for use according to Paragraph 44, wherein the mole ratio is 30:1 to 250:1.

Paragraph 47. The pharmaceutical combination for use according to Paragraph 42 or Paragraph 43, wherein the compound of formula I or pharmaceutically acceptable derivative thereof is administered to the subject according to a continuous treatment schedule and the compound of formula II or pharmaceutically acceptable salt thereof is administered to the subject according to a cyclic treatment schedule and wherein the mole ratio of the total mole amount of the doses of the compound of formula I or pharmaceutically acceptable derivative thereof administered to the subject over a period of the same duration of the treatment cycle of the compound of formula II or pharmaceutically acceptable salt thereof to the total mole amount of the doses of the compound of formula II or pharmaceutically acceptable salt thereof administered to the subject over the treatment cycle is 1:1 to 800:1.

Paragraph 48. The pharmaceutical combination for use according to Paragraph 47, wherein the mole ratio is 20:1 to 300:1.

Paragraph 49. The pharmaceutical combination for use according to Paragraph 47, wherein the mole ratio is 30:1 to 250:1.

Paragraph 50. The pharmaceutical combination for use according to any one of Paragraphs 42 to 49, wherein the compound of formula I or pharmaceutically acceptable derivative thereof is administered orally at dose corresponding to the mole equivalent of about 2 mg to about 30 mg of the dihydrochloride salt of the compound of formula I-B per day on days when administered, and wherein the compound of formula II or pharmaceutically acceptable salt thereof is administered intravenously at a dose corresponding to the mole equivalent of eribulin mesylate of about 0.1 mg/m² to about 2 mg/m² per week during weeks when administered.

Paragraph 51. The pharmaceutical combination for use according to Paragraph 50, wherein the compound of formula I or pharmaceutically acceptable derivative thereof is administered at a dose corresponding to the mole equivalent of about 4 mg to about 20 mg of the dihydrochloride salt of the compound of formula I-B per day on days when administered.

Paragraph 52. The pharmaceutical combination for use according to Paragraph 50, wherein the compound of formula I or pharmaceutically acceptable derivative thereof is administered at a dose corresponding to the mole equivalent of about 8 mg to about 20 mg of the dihydrochloride salt of the compound of formula I-B per day on days when administered.

Paragraph 53. The pharmaceutical combination for use according to any one of Paragraphs 50 to 52, wherein the compound of formula I or pharmaceutically acceptable derivative thereof is administered to the subject at least once per day.

Paragraph 54. The pharmaceutical combination for use according to any one of Paragraphs 50 to 53, wherein the compound of formula II or pharmaceutically acceptable salt thereof is administered at a dose corresponding to the mole equivalent of eribulin mesylate of about 0.3 mg/m² to about 1.5 mg/m² per week during weeks when administered.

Paragraph 55. The pharmaceutical combination for use according to any one of Paragraphs 50 to 54, wherein the compound of formula II or pharmaceutically acceptable salt thereof is administered to the subject according to a 21-day treatment cycle with administration initiated on days 1 and 8, or according to a 28-day treatment cycle with administration initiated on days 1 and 15.

Paragraph 56. The pharmaceutical combination for use according to any one of Paragraphs 42 to 49, wherein the compound of formula I or pharmaceutically acceptable derivative thereof is administered intravenously at a dose corresponding to the mole equivalent of about 15 mg/m² to about 160 mg/m² of the dihydrochloride salt of the compound of formula I-B per week during weeks when administered, and wherein the compound of formula II or pharmaceutically acceptable salt thereof is administered intravenously at a dose corresponding to the mole equivalent of eribulin mesylate of about 0.1 mg/m² to about 2 mg/m² per week during weeks when administered.

Paragraph 57. The pharmaceutical combination for use according to Paragraph 56, wherein the compound of formula I or pharmaceutically acceptable derivative thereof is administered at a dose corresponding to the mole equivalent of about 30 mg/m² to about 100 mg/m² of the dihydrochloride salt of the compound of formula I-B per week during weeks when administered.

Paragraph 58. The pharmaceutical combination for use according to Paragraph 56, wherein the compound of formula I or pharmaceutically acceptable derivative thereof is administered at a dose corresponding to the mole equivalent of about 30 mg/m² to about 70 mg/m² of the dihydrochloride salt of the compound of formula I-B per week during weeks when administered.

Paragraph 59. The pharmaceutical combination for use according to any one of Paragraphs 56 to 58, wherein the compound of formula I or pharmaceutically acceptable derivative thereof is administered according to a 21-day treatment cycle with administration initiated on days 1 and 8, or a 28-day treatment cycle with administration initiated on days 1, 8 and 15.

Paragraph 60. The pharmaceutical combination for use according to any one of Paragraphs 56 to 59, wherein the compound of formula II or pharmaceutically acceptable salt thereof is administered intravenously at a dose corresponding to the mole equivalent of eribulin mesylate of about 0.3 mg/m² to about 1.5 mg/m² per week during weeks when administered.

Paragraph 61. The pharmaceutical combination for use according to any one of Paragraphs 56 to 59, wherein the compound of formula II or pharmaceutically acceptable salt thereof is administered according to a 21-day treatment cycle with administration initiated on days 1 and 8, or according to a 28-day treatment cycle with administration initiated on days 1 and 15.

Paragraph 62. The pharmaceutical combination for use according to any one of Paragraphs 42 to 61, wherein the neoplastic disease is a solid tumour.

Paragraph 63. The pharmaceutical combination for use according to any one of Paragraphs 42 to 61, wherein the neoplastic disease is selected from the group consisting of epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, myeloproliferative disorders, lymphoproliferative disorders and myelodysplastic syndromes.

Paragraph 64. The pharmaceutical combination for use according to any one of Paragraphs 42 to 63, wherein the disease is a cancer.

Paragraph 65. The pharmaceutical combination for use according to Paragraph 64, wherein the cancer in terms of the organs and parts of the body affected is selected from the brain, breast (including triple negative breast cancer), cervix, ovaries, colon, rectum, (including colon and rectum i.e. colorectal cancer), lung, (including small cell lung cancer, non-small cell lung cancer, large cell lung cancer and mesothelioma), endocrine system, bone, adrenal gland, thymus, liver, stomach, intestine, (including gastric cancer), pancreas, bone marrow, haematological malignancies, (such as lymphoma, leukaemia, myeloma or lymphoid malignancies), bladder, urinary tract, kidneys, skin, thyroid, head, neck, prostate and testis.

Paragraph 66. The pharmaceutical combination for use according to Paragraph 64, wherein the cancer is selected from brain cancer (e.g. glioblastoma), breast cancer (including triple negative breast cancer), prostate cancer, cervical cancer, ovarian cancer, gastric cancer, colorectal cancer, pancreatic cancer, liver cancer, brain cancer, neuroendocrine cancer, lung cancer, kidney cancer, haematological malignancies, melanoma and sarcomas.

Paragraph 67. The pharmaceutical combination for use according to Paragraph 66, wherein the cancer is breast cancer.

Paragraph 68. A compound of formula I or a pharmaceutically acceptable derivative thereof as defined in any one of Paragraphs 1 to 4, for use in combination with a compound of formula II or pharmaceutically acceptable salt thereof as defined in Paragraph 1 or Paragraph 5, for the treatment of a neoplastic disease in a subject, in particular a human.

Paragraph 69. The compound of formula I or a pharmaceutically acceptable derivative thereof for use according to Paragraph 64, wherein the compound of formula I or a pharmaceutically acceptable derivative thereof is administered to the subject as defined in any one of Paragraphs 42 to 61.

Paragraph 70. The compound of formula I or a pharmaceutically acceptable derivative thereof for use according to Paragraph 68 or Paragraph 69, wherein the neoplastic disease is as defined in any one of Paragraphs 62 to 67.

Paragraph 71. A compound of formula II or pharmaceutically acceptable salt thereof as defined in Paragraph 1 or Paragraph 5, for use in combination with a compound of formula I or pharmaceutically acceptable derivative thereof as defined in any one of Paragraphs 1 to 4, for the treatment of a neoplastic disease.

Paragraph 72. The compound of formula II or pharmaceutically acceptable salt thereof for use according to Paragraph 71, wherein the compound of formula II or a pharmaceutically acceptable salt thereof is administered to the subject as defined in any one of Paragraphs 42 to 61.

Paragraph 73. The compound of formula II or pharmaceutically acceptable salt thereof for use according to Paragraph 71 or Paragraph 72, wherein the neoplastic disease is as defined in any one of Paragraphs 62 to 67.

Paragraph 74. Use of a pharmaceutical combination as defined in any one of Paragraphs 1 to 5 in the preparation of single-agent medicaments or as a combined medicament for the treatment of a neoplastic disease in a subject, in particular a human.

Paragraph 75. Use according to Paragraph 74, wherein the compound of formula I or pharmaceutically acceptable derivative thereof and the compound of formula II or pharmaceutically acceptable salt thereof are for simultaneous, sequential or separate administration to the subject.

Paragraph 76. Use according to Paragraph 74 or Paragraph 75, wherein the compound of formula I or pharmaceutically acceptable derivative thereof and the compound of formula II or a pharmaceutically acceptable salt thereof are administered to the subject as defined in any one of Paragraphs 42 to 61.

Paragraph 77. Use according to any one of Paragraphs 74 to 76, wherein the neoplastic disease is as defined in any one of Paragraphs 62 to 67.

Paragraph 78. Use of a compound of formula I or a pharmaceutically acceptable derivative thereof as defined in any one of Paragraphs 1 to 4 in the preparation of a single-agent medicament for use in combination with a compound of formula II or pharmaceutically acceptable salt thereof or in the preparation of a combined medicament with the compound of formula II or pharmaceutically acceptable salt thereof, for the treatment of a neoplastic disease in a subject, in particular a human.

Paragraph 79. Use according to Paragraph 78, wherein the compound of formula I or pharmaceutically acceptable derivative thereof is administered to the subject as defined in any one of Paragraphs 42 to 61.

Paragraph 80. Use according to Paragraph 74 or Paragraph 75, wherein the neoplastic disease is as defined in any one of Paragraphs 62 to 67.

Paragraph 81. Use of a compound of formula II or a pharmaceutically acceptable salt thereof as defined in Paragraph 1 or Paragraph 5 in the preparation of a single-agent medicament for use in combination with a compound of formula I or pharmaceutically acceptable derivative thereof or in the preparation of a combined medicament with the compound of formula I or pharmaceutically acceptable derivative thereof, for the treatment of a neoplastic disease in a subject, in particular a human.

Paragraph 82. Use according to Paragraph 81, wherein the compound of formula II or pharmaceutically acceptable salt thereof is administered to the subject as defined in any one of Paragraphs 42 to 61.

Paragraph 83. Use according to Paragraph 81 or Paragraph 82, wherein the neoplastic disease is as defined in any one of Paragraphs 62 to 67.

Paragraph 84. A kit comprising a pharmaceutical combination as defined in any one of Paragraphs 1 to 9, wherein component (a) and component (b) are provided as separate dosage units.

Paragraph 85. The kit according to Paragraph 84, wherein the kit is for use in treating a neoplastic disease.

Paragraph 86. The kit according to paragraph 85, further comprising instructions for simultaneous, separate or sequential administration thereof for use in the treatment of a neoplastic disease, in particular a cancer, in a subject, in particular a human.

The invention claimed is:

1. A pharmaceutical combination comprising (a) a compound of formula I:

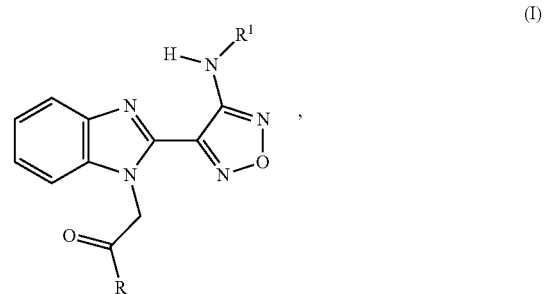

(I)

wherein:

R represents phenyl or pyridinyl;

wherein phenyl is optionally substituted by one or two substituents independently selected from lower alkyl, lower alkoxy, hydroxyl, amino, lower alkylamino, lower dialkylamino, acetylamino, halogen and nitro;

and wherein pyridinyl is optionally substituted by amino or halogen;

R1 represents hydrogen or cyano-lower alkyl;

and wherein the prefix lower with respect to the substituents lower alkyl, lower alkoxy, lower alkylamino and lower dialkylamino denotes a radical having up to and including a maximum of 4 carbon atoms; or a pharmaceutically acceptable salt thereof or a prodrug or pharmaceutically acceptable salt of a prodrug thereof, wherein the prodrug is an in vivo hydrolysable ester or amide of a compound of the formula I;

and (b) a compound of formula II (eribulin):

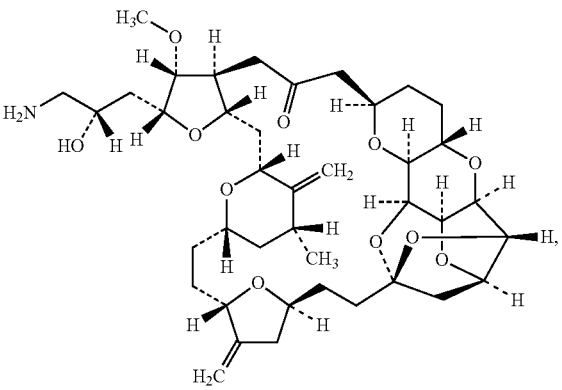

(II)

or a pharmaceutically acceptable salt thereof.

2. The pharmaceutical combination according to claim 1, wherein the compound of formula I or pharmaceutically acceptable salt thereof or a prodrug or pharmaceutically acceptable salt of a prodrug thereof is a compound of formula I-A

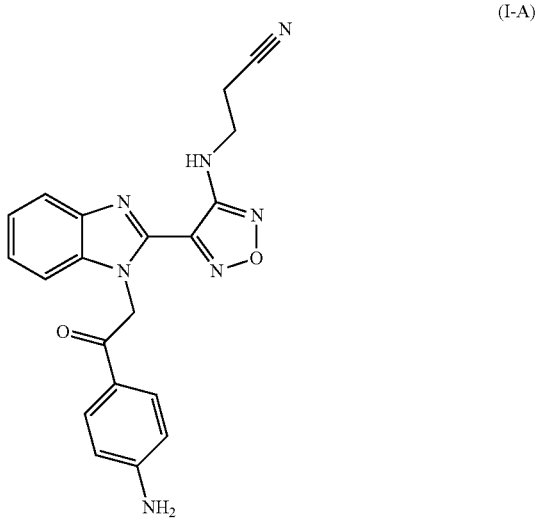 [SMILES: N#CCCNc1nonc1-c1nc2ccccc2n1CC(=O)c1ccc(N)cc1]

(I-A)

or a pharmaceutically acceptable salt thereof, or a compound of formula I-B

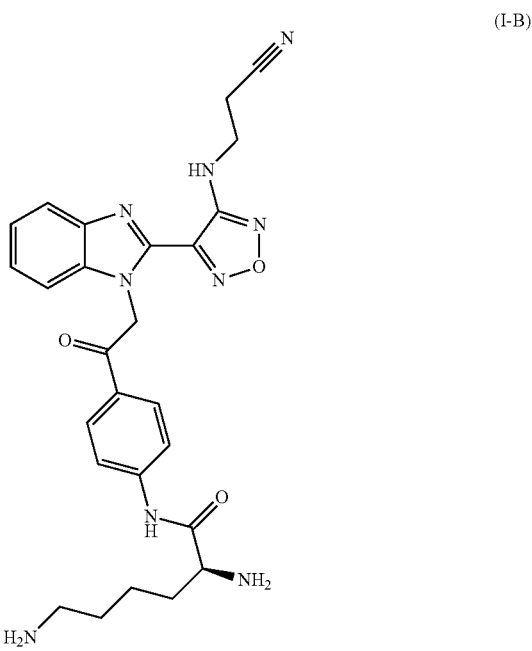 [SMILES: N#CCCNc1nonc1-c1nc2ccccc2n1CC(=O)c1ccc(NC(=O)[C@@H](N)CCCCN)cc1]

(I-B)

or a pharmaceutically acceptable salt thereof.

3. The pharmaceutical combination according to claim 2, wherein the compound of formula I or pharmaceutically acceptable salt thereof or a prodrug or pharmaceutically acceptable salt of a prodrug thereof is the dihydrochloride salt of the compound of formula I-B and wherein the compound of formula II or a pharmaceutically acceptable salt thereof is eribulin mesylate.

4. The pharmaceutical combination according to claim 1, wherein the mole ratio of the mole amount of the compound of formula I or pharmaceutically acceptable salt thereof or a prodrug or pharmaceutically acceptable salt of a prodrug thereof to the mole amount of the compound of formula II or pharmaceutically acceptable salt thereof is 1:1 to 800:1.

5. A method for treating a neoplastic disease in a subject, comprising the step of administering a pharmaceutical combination according to claim 1 to said subject in need thereof, wherein the neoplastic disease is selected from the group consisting of epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, myeloproliferative disorders, lymphoproliferative disorders and myelodysplastic syndromes.

6. The method according to claim 5, wherein the compound of formula I or pharmaceutically acceptable salt thereof or a prodrug or pharmaceutically acceptable salt of a prodrug thereof and the compound of formula II or pharmaceutically acceptable salt thereof are administered to the subject according to cyclic treatment schedules;
wherein when the treatment cycles are of the same duration the mole ratio of the total mole amount of the doses of the compound of formula I or pharmaceutically acceptable salt thereof or a prodrug or pharmaceutically acceptable salt of a prodrug thereof to the total mole amount of the doses of the compound of formula II or pharmaceutically acceptable salt thereof administered to the subject over the respective treatment cycles is 1:1 to 800:1;
and wherein when the treatment cycles are of different duration the ratio of the total mole amount of the doses of the compound of formula I or pharmaceutically acceptable salt thereof or a prodrug or pharmaceutically acceptable salt of a prodrug thereof to the total mole amount of the doses of the compound of formula II or pharmaceutically acceptable salt thereof administered to the subject over a theoretical period of time corresponding to a common multiple of the duration of the respective treatment cycles is 1:1 to 800:1.

7. The method according to claim 5, wherein the compound of formula I or pharmaceutically acceptable salt thereof or a prodrug or pharmaceutically acceptable salt of a prodrug thereof is administered to the subject according to a continuous treatment schedule and the compound of formula II or pharmaceutically acceptable salt thereof is administered to the subject according to a cyclic treatment schedule and wherein the mole ratio of the total mole amount of the doses of the compound of formula I or pharmaceutically acceptable salt thereof or a prodrug or pharmaceutically acceptable salt of a prodrug thereof administered to the subject over a period of the same duration of the treatment cycle of the compound of formula II or pharmaceutically acceptable salt thereof to the total mole amount of the doses of the compound of formula II or pharmaceutically acceptable salt thereof administered to the subject over the treatment cycle is 1:1 to 800:1.

8. The method according to claim 5, wherein the compound of formula I or pharmaceutically acceptable salt thereof or a prodrug or pharmaceutically acceptable salt of a prodrug thereof is administered orally at dose corresponding to the mole equivalent of about 2 mg to about 30 mg of the dihydrochloride salt of the compound of formula I-B per day on days when administered, and wherein the compound of formula II or pharmaceutically acceptable salt thereof is administered intravenously at a dose corresponding to the mole equivalent of eribulin mesylate of about 0.1 mg/m$^2$ to about 2 mg/m$^2$ per week during weeks when administered.

9. The method according to claim 8, wherein the compound of formula I or pharmaceutically acceptable salt thereof or a prodrug or pharmaceutically acceptable salt of a prodrug thereof is administered to the subject at least once per day, and wherein the compound of formula II or pharmaceutically acceptable salt thereof is administered to the subject according to a 21-day treatment cycle with administration initiated on days 1 and 8, or according to a 28-day treatment cycle with administration initiated on days 1 and 15.

10. The method according to claim 5, wherein the compound of formula I or pharmaceutically acceptable salt thereof or a prodrug or pharmaceutically acceptable salt of a prodrug thereof is administered intravenously at a dose corresponding to the mole equivalent of about 15 mg/m$^2$ to about 160 mg/m$^2$ of the dihydrochloride salt of the compound of formula I-B:

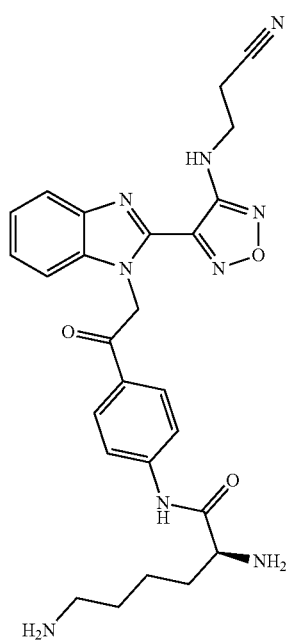

(I-B)

per week during weeks when administered, and wherein the compound of formula II or pharmaceutically acceptable salt thereof is administered intravenously at a dose corresponding to the mole equivalent of eribulin mesylate of about 0.1 mg/m$^2$ to about 2 mg/m$^2$ per week during weeks when administered.

11. The method according to claim 10, wherein the compound of formula I or pharmaceutically acceptable salt thereof or a prodrug or pharmaceutically acceptable salt of a prodrug thereof is administered according to a 21-day treatment cycle with administration initiated on days 1 and 8, or a 28-day treatment cycle with administration initiated on days 1, 8 and 15, and wherein the compound of formula II or pharmaceutically acceptable salt thereof is administered according to a 21-day treatment cycle with administration initiated on days 1 and 8, or according to a 28-day treatment cycle with administration initiated on days 1 and 15.

12. The method according to claim 5, wherein the neoplastic disease is a cancer.

13. The method according to claim 5, wherein the subject is human.

14. The method according to claim 12, wherein the cancer is breast cancer.

15. The method according to claim 12, wherein the cancer is selected from the group consisting of brain cancer, breast cancer, prostate cancer, cervical cancer, ovarian cancer, gastric cancer, colorectal cancer, pancreatic cancer, liver cancer, neuroendocrine cancer, lung cancer, kidney cancer, haematological malignancies, melanoma and sarcomas.

16. The method according to claim 12, wherein the cancer is selected from the group consisting of breast cancer, colorectal cancer, lung cancer, pancreatic cancer and haematological malignancies.

17. The method according to claim 14, wherein the breast cancer is triple negative breast cancer.

18. The pharmaceutical combination according to claim 2, wherein the mole ratio of the mole amount of the compound of formula I-A or pharmaceutically acceptable salt thereof or a compound of formula I—B or pharmaceutically acceptable salt thereof to the mole amount of the compound of formula II or pharmaceutically acceptable salt thereof is 1:1 to 800:1.

19. The method according to claim 5, wherein the compound of formula I or pharmaceutically acceptable salt thereof or a prodrug or pharmaceutically acceptable salt of a prodrug thereof is a compound of formula I-A

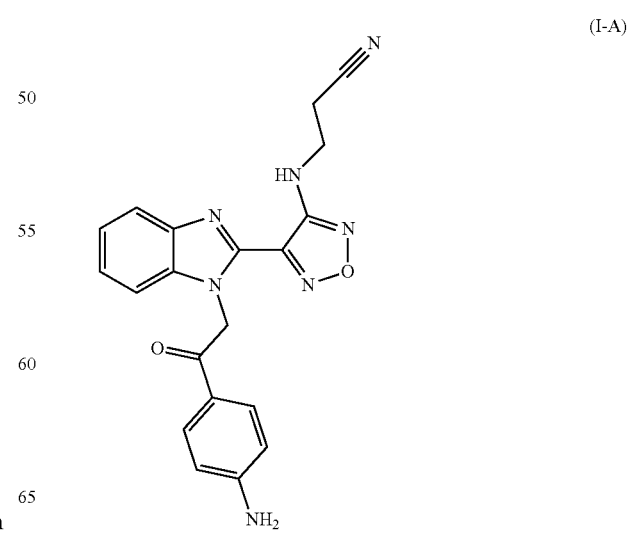

(I-A)

or a pharmaceutically acceptable salt thereof, or a compound of formula I-B

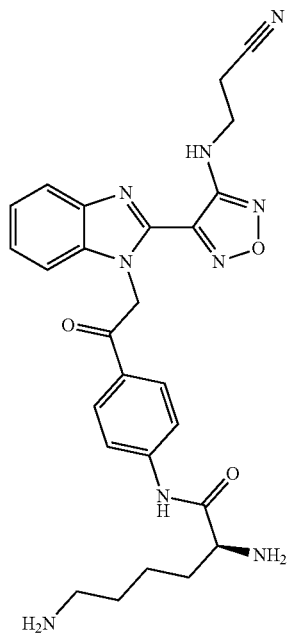

(I-B)

or a pharmaceutically acceptable salt thereof.

20. The method according to claim 19, wherein the compound of formula I-A or pharmaceutically acceptable salt thereof or a compound of formula I-B or pharmaceutically acceptable salt thereof and the compound of formula II or pharmaceutically acceptable salt thereof are administered to the subject according to cyclic treatment schedules;
wherein when the treatment cycles are of the same duration the mole ratio of the total mole amount of the doses of the compound of formula I-A or pharmaceutically acceptable salt thereof or a compound of formula I-B or pharmaceutically acceptable salt thereof to the total mole amount of the doses of the compound of formula II or pharmaceutically acceptable salt thereof administered to the subject over the respective treatment cycles is 1:1 to 800:1;
and wherein when the treatment cycles are of different duration the ratio of the total mole amount of the doses of the compound of formula I-A or pharmaceutically acceptable salt thereof or a compound of formula I-B or pharmaceutically acceptable salt thereof to the total mole amount of the doses of the compound of formula II or pharmaceutically acceptable salt thereof administered to the subject over a theoretical period of time corresponding to a common multiple of the duration of the respective treatment cycles is 1:1 to 800:1.

21. The method according to claim 19, wherein the compound of formula I-A or pharmaceutically acceptable salt thereof or a compound of formula I-B or pharmaceutically acceptable salt thereof is administered to the subject according to a continuous treatment schedule and the compound of formula II or pharmaceutically acceptable salt thereof is administered to the subject according to a cyclic treatment schedule and wherein the mole ratio of the total mole amount of the doses of the compound of formula I-A or pharmaceutically acceptable salt thereof or a compound of formula I-B or pharmaceutically acceptable salt thereof administered to the subject over a period of the same duration of the treatment cycle of the compound of formula II or pharmaceutically acceptable salt thereof to the total mole amount of the doses of the compound of formula II or pharmaceutically acceptable salt thereof administered to the subject over the treatment cycle is 1:1 to 800:1.

22. The method according to claim 19, wherein the compound of formula I-A or pharmaceutically acceptable salt thereof or a compound of formula I-B or pharmaceutically acceptable salt thereof is administered orally at dose corresponding to the mole equivalent of about 2 mg to about 30 mg of the dihydrochloride salt of the compound of formula I-B per day on days when administered, and wherein the compound of formula II or pharmaceutically acceptable salt thereof is administered intravenously at a dose corresponding to the mole equivalent of eribulin mesylate of about 0.1 mg/m$^2$ to about 2 mg/m$^2$ per week during weeks when administered.

23. The method according to claim 22, wherein the compound of formula I-A or pharmaceutically acceptable salt thereof or a compound of formula I-B or pharmaceutically acceptable salt thereof is administered to the subject at least once per day, and wherein the compound of formula II or pharmaceutically acceptable salt thereof is administered to the subject according to a 21-day treatment cycle with administration initiated on days 1 and 8, or according to a 28-day treatment cycle with administration initiated on days 1 and 15.

24. The method according to claim 19, wherein the compound of formula I-A or pharmaceutically acceptable salt thereof or a compound of formula I-B or pharmaceutically acceptable salt thereof is administered intravenously at a dose corresponding to the mole equivalent of about 15 mg/m$^2$ to about 160 mg/m$^2$ of the dihydrochloride salt of the compound of formula I-B per week during weeks when administered, and wherein the compound of formula II or pharmaceutically acceptable salt thereof is administered intravenously at a dose corresponding to the mole equivalent of eribulin mesylate of about 0.1 mg/m$^2$ to about 2 mg/m$^2$ per week during weeks when administered.

25. The method according to claim 24, wherein the compound of formula I-A or pharmaceutically acceptable salt thereof or a compound of formula I-B or pharmaceutically acceptable salt thereof is administered according to a 21-day treatment cycle with administration initiated on days 1 and 8, or a 28-day treatment cycle with administration initiated on days 1, 8 and 15, and wherein the compound of formula II or pharmaceutically acceptable salt thereof is administered according to a 21-day treatment cycle with administration initiated on days 1 and 8, or according to a 28-day treatment cycle with administration initiated on days 1 and 15.

26. The method according to claim 19, wherein the neoplastic disease is a cancer.

27. The method according to claim 19, wherein the subject is human.

28. The method according to claim 26, wherein the cancer is selected from the group consisting of brain cancer, breast cancer, prostate cancer, cervical cancer, ovarian cancer, gastric cancer, colorectal cancer, pancreatic cancer, liver cancer, neuroendocrine cancer, lung cancer, kidney cancer, haematological malignancies, melanoma and sarcomas.

29. The method according to claim 26, wherein the cancer is selected from the group consisting of breast cancer, colorectal cancer, lung cancer, pancreatic cancer and haematological malignancies.

30. The method according to claim 26, wherein the cancer is breast cancer.

31. The method according to claim 30, wherein the breast cancer is triple negative breast cancer.

32. The method according to claim 5, wherein the compound of formula I or pharmaceutically acceptable salt thereof or a prodrug or pharmaceutically acceptable salt of a prodrug thereof is the dihydrochloride salt of the compound of formula I-B:

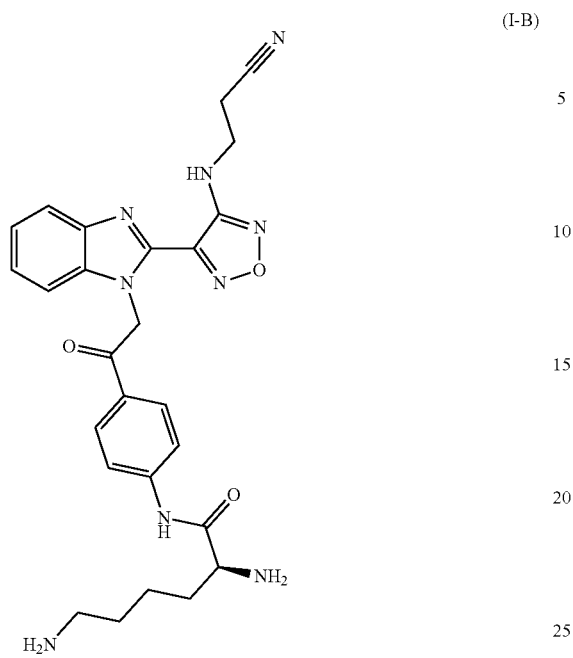
(I-B)
and wherein the compound of formula II or a pharmaceutically acceptable salt thereof is eribulin mesylate.
* * * * *